(12) United States Patent
Trauner et al.

(10) Patent No.: US 9,334,231 B2
(45) Date of Patent: *May 10, 2016

(54) PHOTOREACTIVE SYNTHETIC REGULATOR OF PROTEIN FUNCTION AND METHODS OF USE THEREOF

(71) Applicant: The Regents of the University of California, Oakland, CA (US)

(72) Inventors: Dirk Trauner, Munich (DE); Ehud Y. Isacoff, Berkeley, CA (US); Richard H. Kramer, Oakland, CA (US); Matthew R. Banghart, Oakland, CA (US); Doris L. Fortin, Ottawa (CA); Alexandre Mourot, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/626,124

(22) Filed: Feb. 19, 2015

(65) Prior Publication Data

US 2015/0158811 A1    Jun. 11, 2015

Related U.S. Application Data

(63) Continuation of application No. 13/059,052, filed as application No. PCT/US2009/062491 on Oct. 29, 2009, now Pat. No. 8,993,736.

(60) Provisional application No. 61/122,608, filed on Dec. 15, 2008, provisional application No. 61/110,369, filed on Oct. 31, 2008.

(51) Int. Cl.
| | |
|---|---|
| *C07C 245/08* | (2006.01) |
| *C09B 44/04* | (2006.01) |
| *C12Q 1/02* | (2006.01) |
| *G01N 33/50* | (2006.01) |
| *G01N 33/566* | (2006.01) |

(52) U.S. Cl.
CPC ............... *C07C 245/08* (2013.01); *C09B 44/04* (2013.01); *C12Q 1/025* (2013.01); *G01N 33/5008* (2013.01); *G01N 33/566* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 8,178,496 B2 | 5/2012 | Trauner et al. | |
| 8,993,736 B2 * | 3/2015 | Trauner et al. | 534/573 |
| 2007/0128662 A1 | 6/2007 | Isacoff et al. | |

FOREIGN PATENT DOCUMENTS

| | | |
|---|---|---|
| DE | 1151623 B | 7/1963 |
| DE | 19802940 A1 * | 8/1999 |
| WO | WO 2007/024290 A2 | 3/2007 |

OTHER PUBLICATIONS

Banghart, et al.; "Light-activated ion channels for remote control of neuronal firing"; Nature Neuroscience; 7:1381-1386 (2004).
Bartels, et al.; "Photochromic activators of the acetylcholine receptor"; Proceedings of the National Academy of Sciences of the U.S.A.; vol. 68, pp. 1820-1823 (1971).
Caamano, et al.; "A Light-Modulated Sequence-Specific DNA-Binding Peptide"; Angewandte Chemie (International ed. in English) 39:3104-3107 (2000).
Chemical compound (CAS RN 807298-08-4), entered the CAS STN database on Jan. 2, 2005.
Chemical compound (CAS RN 856566-17-1), entered the CAS STN database on Jul. 22, 2005.
French, et al.; "Blockage of Squid Axon Potassium Conductance by Internal Tetra-N-Alkylammonium Ions of Various Sizes"; Biophysical Journal; vol. 34, pp. 271-291 (May 1981).
Fujita, et al.; "Light control of mitochondrial complex I activity by a photoresponsive inhibitor"; Biochemistry; 45:6581-6586 (2006).
Givens, et al.; "New photoprotecting groups: desyl and p-hydroxyphenacyl phosphate and carboxylate esters"; Methods in Enzymology, Marriott, G., Ed. Academic Press, New York; 291:1-29 (1998).
Gorostiza, et al.; "Optical switches for remote and noninvasive control of cell signaling"; Science; 322:395 (2008).
Guo, et al.; "Kinetics of Inward-Rectifier K+ Channel Block by Quaternary Alkylammonium Ions: Dimension and Properties of the Inner Pore"; J. Gen. Physiol.; vol. 117, pp. 395-405 (May 2001).
Kaufman, et al.; "Photoregulation of an enzymic process by means of a light-sensitive ligand"; Science; 162: 1487-1489 (1968).
Lester, et al.; "A covalently bound photoisomerizable agonist: comparison with reversibly bound agonists at Electrophorus electroplaques"; The Journal of General Physiology; 75:207-232 (1980).
Mayer, et al.; Biologically active molecules with a "light switch"; Angewandte Chemie (International ed. in English); 45:4900-4921 (2006).
Volgraf, et al.; "Allosteric control of an ionotropic glutamate receptor with an optical switch"; Nature Chemical Biology; 2:47-52 (2006).

* cited by examiner

*Primary Examiner* — Yong Chu
(74) *Attorney, Agent, or Firm* — Bozicevic, Field & Francis LLP; Paula A. Borden; Rudy J. Ng

(57) ABSTRACT

The present disclosure provides a photoreactive synthetic regulator of protein function. The present disclosure further provides a light-regulated polypeptide that includes a subject synthetic regulator. Also provided are cells and membranes comprising a subject light-regulated polypeptide. The present disclosure further provides methods of modulating protein function, involving use of light.

28 Claims, 12 Drawing Sheets

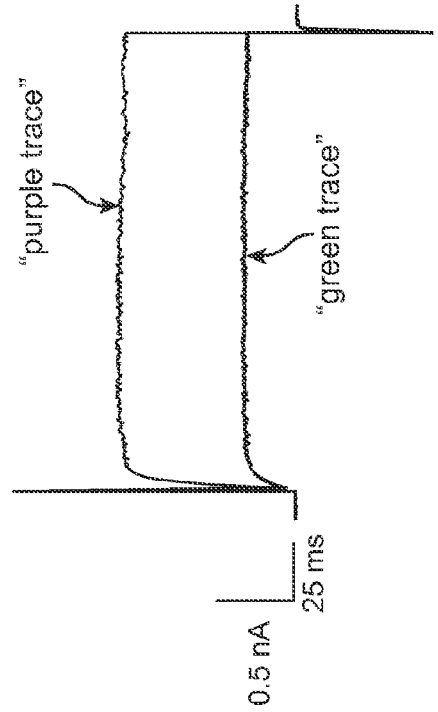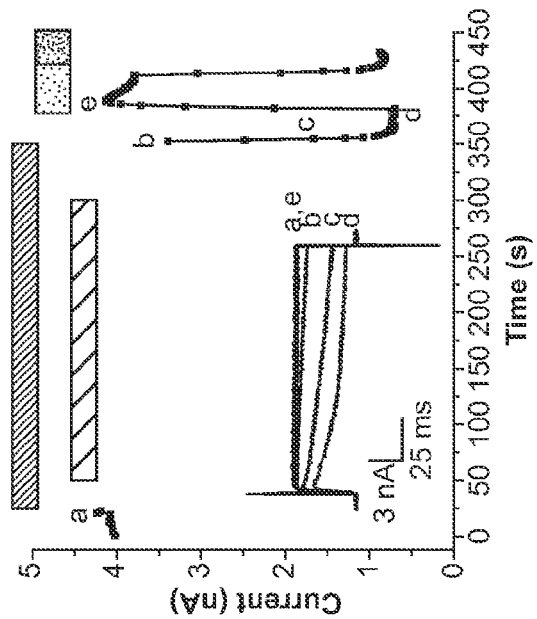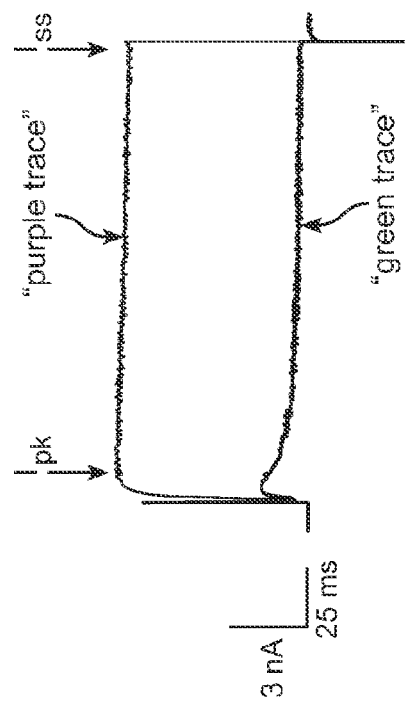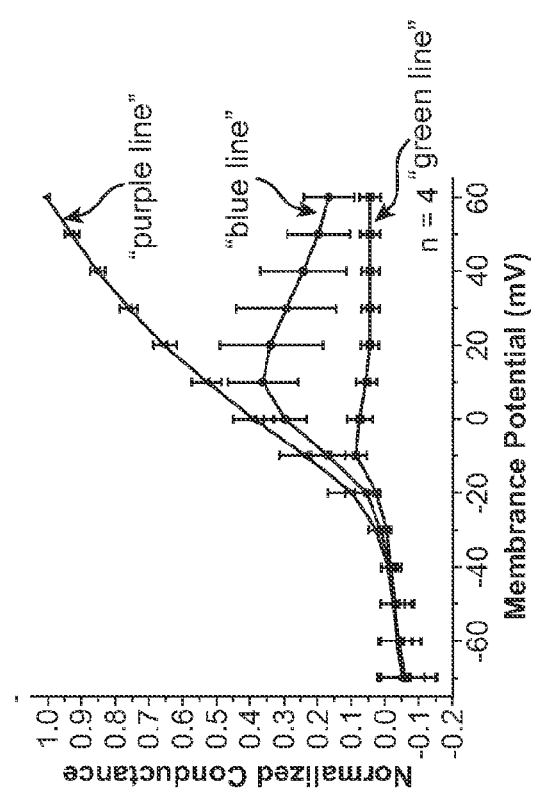
FIG. 3A
FIG. 3B
FIG. 3C
FIG. 3D

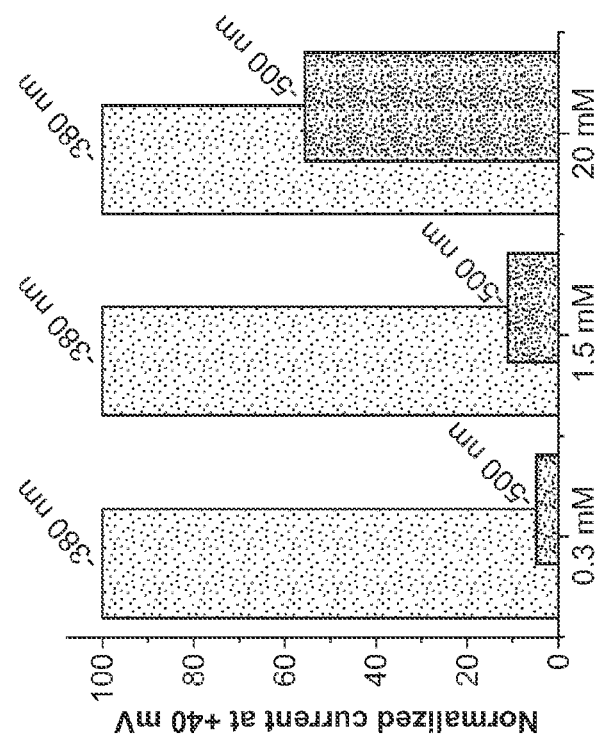
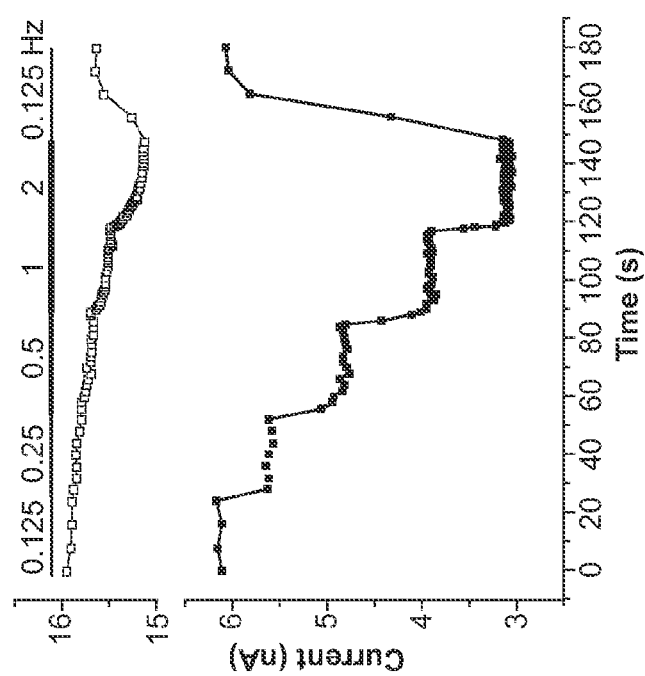
FIG. 3F
FIG. 3E

| R | Compound | μM | % Block | active isomer |
|---|---|---|---|---|
| ![acetamide] | 4 | 1000 | >95 | trans |
| ![propanamide] | 5 | 800 | >95 | trans |
| ![butanamide] | 6 | 300 | >95 | trans |
| ![pentenamide] | 7 | 200 | >95 | trans |
| ![benzamide] | 8 | 25 | >95 | trans |
| ![triethylammonium acetamide] | 9 | 2000 | 0 | trans |
| H | 10 | 1000 | ND* | trans = cis |
| ![isopropyl] | 11 | 40 | ~50 | cis |

PHOTOREACTIVE SYNTHETIC REGULATOR OF PROTEIN FUNCTION AND METHODS OF USE THEREOF

CROSS-REFERENCE

This application is a continuation of U.S. patent application Ser. No. 13/059,052, filed Feb. 11, 2011, now U.S. Pat. No. 8,993,736, which is a national stage filing under 35 U.S.C. §371 of PCT/US2009/062491, filed Oct. 29, 2009, which claims the benefit of U.S. Provisional Patent Application No. 61/110,369, filed Oct. 31, 2008, and U.S. Provisional Patent Application No. 61/122,608, filed Dec. 15, 2008, which applications are incorporated herein by reference in their entirety.

STATEMENT REGARDING FEDERALLY SPONSORED RESEARCH

This invention was made with government support under Grant No. 1PN2-EY018241 awarded by the National Institutes of Health, and Grant No. CHE 0724212 awarded by the National Science Foundation. The government has certain rights in the invention.

BACKGROUND

The precise regulation of protein activity is fundamental to life. A mechanism of regulation, found across protein classes, from enzymes, to motors, to signaling proteins, is allosteric control of an active site by a remote regulatory binding site.

Many proteins function like molecular machines that undergo mechanical movements in response to input signals. These signals can consist of changes in voltage, membrane tension, temperature or, most commonly, ligand concentration. Ligands provide information about events in the external world, or about the energetic or biosynthetic state of the cell, and can be as small as a proton or as large as a whole protein. In allostery, ligand binding induces a structural change of a sensor domain, which propagates to a functional domain of the protein and alters its behavior. Such conformational control can operate over long distances, crossing a membrane or passing from one protein to another in a complex.

Photochromic molecules have emerged as powerful optical tools to control protein and cellular function in neuroscience. Photoswitchable tethered ligands are covalently anchored to protein surfaces through photoisomerizable tethers. Photoswitching changes the length and geometry of the tether to alter the effective concentration of ligand at its binding site, thereby modulating protein function.

There is a need in the art for methods of regulating protein function.
Literature Gorostiza and Isacoff (2008) *Science* 322:395; Kaufman et al. (1968) *Science* 162:1487-1489; Bartels et al. (1971) *Proc. Natl. Acad. Sci. U.S.A.* 68:1820-1823; Fujita et al. (2006) *Biochemistry* 45:6581-6586; Caamano et al. (2000) *Angew. Chem., Int. Ed. Engl.* 39:3104-3107; Mayer and Heckel (2006) *Angew. Chem., Int. Ed. Engl.* 45:4900-4921; Givens et al. (1998) *In Methods in Enzymology*, Marriott, G., Ed. Academic Press, New York, 291:1-29; Volgraf et al. (2006) *Nature Chem. Biol.* 2:47-52; U.S. Patent Publication No. 2007/0128662; Lester et al. *J. Gen. Physiol.* 75:207-232 (1980); Banghart et al. *Nature Neurosci.* 7:1381-1386 (2004); WO 2007/024290.

SUMMARY OF THE INVENTION

The present disclosure provides a photoreactive synthetic regulator of protein function. The present disclosure further provides a light-regulated polypeptide that includes a subject synthetic regulator. Also provided are cells and membranes comprising a subject light-regulated polypeptide. The present disclosure further provides methods of modulating protein function, involving use of light.

BRIEF DESCRIPTION OF THE DRAWINGS

FIGS. 3A-F depict the effect of AAQ on the Sh-IR internal TEA-binding site.

DEFINITIONS

Figure 1A:
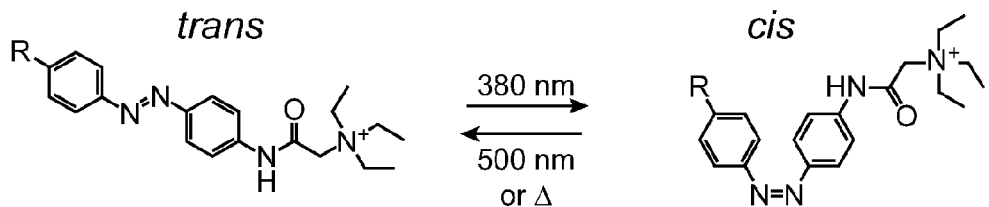
FIGS. 1A-C depict of modes of photoregulating potassium channels.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The following terms have the following meanings unless otherwise indicated. Any undefined terms have their art recognized meanings.

The term "alkyl" refers to a monoradical branched or unbranched saturated hydrocarbon chain, e.g., having from 1 to 40 carbon atoms, from 1 to 10 carbon atoms, or from 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined above wherein one or more carbon atoms in the alkyl chain have been optionally replaced with a heteroatom such as —O—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$Rb, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkylaminoalkyl", "alkylaminoalkenyl" and "alkylaminoalkynyl" refers to the groups R$^a$NHR$^b$— where R$^a$ is alkyl group as defined above and R$^b$ is alkylene, alkenylene or alkynylene group as defined above.

The term "alkaryl" or "aralkyl" refers to the groups -alkylene-aryl and -substituted alkylene-aryl where alkylene, substituted alkylene and aryl are defined herein.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

The term "alkenyl" refers to a monoradical of a branched or unbranched unsaturated hydrocarbon group having from 2 to 40 carbon atoms, from 2 to 10 carbon atoms, or from 2 to 6 carbon atoms and having at least 1 site (e.g., from 1-6 sites) of vinyl unsaturation.

The term "substituted alkenyl" refers to an alkenyl group as defined above having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, alkyl, —SO$_2$-substituted alkyl, —SO$_2$-aryl and —SO$_2$-heteroaryl.

The term "alkynyl" refers to a monoradical of an unsaturated hydrocarbon having from 2 to 40 carbon atoms, from 2 to 20 carbon atoms, or from 2 to 6 carbon atoms and having at least 1 site (e.g., from 1-6 sites) of acetylene (triple bond) unsaturation.

The term "substituted alkynyl" refers to an alkynyl group as defined above having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, alkyl, —SO$_2$-substituted alkyl, —SO$_2$-aryl, and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl, and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl, and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl, and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl, and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Exemplary aryls include phenyl, naphthyl and the like. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

The term "aryloxy" refers to the group aryl-O— wherein the aryl group is as defined above including optionally substituted aryl groups as also defined herein.

The term "amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclic provided that both R's are not hydrogen.

The term "carboxyalkyl" or "alkoxycarbonyl" refers to the groups "—C(O)O-alkyl", "—C(O)O— substituted alkyl", "—C(O)O-cycloalkyl", "—C(O)O-substituted cycloalkyl", "—C(O)O-alkenyl", "—C(O)O— substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl, and the like.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring). Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. Such heteroaralkyl groups are exemplified by pyridylmethyl, pyridylethyl, indolylmethyl, and the like.

The term "heteroaryloxy" refers to the group heteroaryl-O—.

The term "heterocycle" or "heterocyclic" refers to a monoradical saturated or unsaturated group having a single ring or multiple condensed rings, from 1 to 40 carbon atoms and from 1 to 10 hetero atoms, e.g., from 1 to 4 heteroatoms, selected from nitrogen, sulfur, phosphorus, and/or oxygen within the ring. Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-substituted alkyl, —SO$_2$-aryl and —SO$_2$-heteroaryl.

Examples of nitrogen heteroaryls and heterocycles include, but are not limited to, pyrrole, thiophene, furan, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, pyrrolidine, piperidine, piperazine, indoline, morpholine, tetrahydrofuranyl, tetrahydrothiophene, and the like as well as N-alkoxy-nitrogen containing heterocycles.

The term "heterocyclooxy" refers to the group heterocyclic-O—.

The term "heterocyclothio" refers to the group heterocyclic-S—.

The term "heterocyclene" refers to the diradical group formed from a heterocycle, as defined herein, and is exemplified by the groups 2,6-morpholino, 2,5-morpholino and the like.

The term "heteroarylamino" refers to a 5 membered aromatic ring wherein one or two ring atoms are N, the remaining ring atoms being C. The heteroarylamino ring may be fused to a cycloalkyl, aryl or heteroaryl ring, and it may be optionally substituted with one or more substituents, e.g., one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —S(O)$_n$R where n is an integer from 0 to 2 and R is hydrogen (provided that n is 0), alkyl, alkenyl, cycloalkyl, amino, heterocyclo, aryl, heteroaryl, aralkyl, or heteroaralkyl.

The term "heterocycloamino" refers to a saturated monovalent cyclic group of 4 to 8 ring atoms, wherein at least one ring atom is N and optionally contains one or two additional ring heteroatoms selected from the group consisting of N, O, or S(O)n (where n is an integer from 0 to 2), the remaining ring atoms being C, where one or two C atoms may optionally be replaced by a carbonyl group. The heterocycloamino ring may be fused to a cycloalkyl, aryl or heteroaryl ring, and it may be optionally substituted with one or more substituents, e.g., one or two substituents, selected from alkyl, substituted alkyl, cycloalkyl, aryl, aralkyl, heteroaryl, heteroaralkyl, halo, cyano, acyl, amino, substituted amino, acylamino, —OR (where R is hydrogen, alkyl, alkenyl, cycloalkyl, acyl, aryl, heteroaryl, aralkyl, or heteroaralkyl), or —S(O)$_n$R [where n is an integer from 0 to 2 and R is hydrogen (provided that n is 0), alkyl, alkenyl, cycloalkyl, amino, heterocyclo, aryl, heteroaryl, aralkyl, or heteroaralkyl].

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" or "alkylthio" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of the embodiments include all stereochemical isomers arising from the substitution of these compounds.

The term "pharmaceutically-acceptable salt" refers to salts which retain biological effectiveness and are not biologically or otherwise undesirable. In many cases, the compounds of the embodiments are capable of forming acid and/or base salts by virtue of the presence of amino and/or carboxyl groups or groups similar thereto.

Pharmaceutically-acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

It must be noted that as used herein and in the appended claims, the singular forms "a," "an," and "the" include plural referents unless the context clearly dictates otherwise. Thus, for example, reference to "a synthetic regulator of protein function" includes a plurality of such regulators and reference to "the ligand" includes reference to one or more ligands and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a photoreactive synthetic regulator of protein function. The present disclosure further provides a light-regulated polypeptide that includes a subject synthetic regulator. Also provided are cells and membranes comprising a subject light-regulated polypeptide. The present disclosure further provides methods of modulating protein function, involving use of light.

Synthetic Regulator of Protein Function

The present disclosure provides a synthetic regulator of protein function. A subject synthetic regulator of protein function is useful for regulating protein function by use of light. A subject synthetic protein regulator comprises: a) a polypeptide association moiety, which can provide for interaction with the polypeptide or occlusion to a pore; b) a photoisomerizable group; and c) a ligand that binds to a ligand binding site (e.g., an active site, an allosteric site, a pore of an ion channel, etc.) of a protein. A subject synthetic protein regulator (also referred to herein as a "synthetic regulator," or "a photoswitch") is suitable for attachment to a variety of polypeptides, including naturally-occurring (native, or endogenous) polypeptides, recombinant polypeptides, synthetic polypeptides, etc.

A subject synthetic regulator can be provided in any number of configurations, including linear and branched. In some embodiments, a subject synthetic regulator has the structure: $(A)_n$-$X_1$—$(B)_m$—$X_2$—$(C)_p$, where A is a polypeptide association moiety, B is a photoisomerizable group, and C is a ligand, and where each of n, m, and p is independently 1 to 10, e.g., where each of n, m, and p is independently one, two, three, four, five, six, seven, eight, nine, or ten, and where $X_1$, when present, is a spacer; and $X_2$, when present, is a spacer. In some embodiments, $X_1$ and $X_2$ are not present. In some embodiments, $X_1$ and $X_2$ are both present. In some embodiments, only one of $X_1$ and $X_2$ is present. In some embodiments, $X_1$ and $X_2$ are independently selected from alkyl, substituted alkyl, alkenyl, substituted alkenyl, alkynyl, substituted alkynyl, acyl, acylamino, and aminoacyl. In some embodiments, each of n, m, and p is 1. In other embodiments, a subject synthetic regulator comprises two or more (e.g., 2 to 10, e.g., two, three, four, five, six, seven, eight, nine, or ten) photoisomerizable groups. In some embodiments, where the synthetic regulator comprises two or more photoisomerizable groups, the two or more photoisomerizable groups are arranged in tandem, either directly or separated by a spacer.

A subject synthetic regulator can be provided in any number of configurations, including linear and branched. In some embodiments, a subject synthetic regulator has the structure: $(A)_n$-$(B)_m$—$(C)_p$, where A is a polypeptide association moiety, B is a photoisomerizable group, and C is a ligand, and where each of n, m, and p is independently 1 to 10, e.g., where each of n, m, and p is independently one, two, three, four, five, six, seven, eight, nine, or ten. In some embodiments, each of n, m, and p is 1, e.g., a subject synthetic regulator has the structure A-B-C.

In other embodiments, a subject synthetic regulator has the structure: C—$X_1$(A)-B—$X_2$(A)-C, where A is a polypeptide association moiety, B is a photoisomerizable group, and C is a ligand, where $X_1$, when present, is a spacer, where $X_2$, when present, is a spacer, and where X(A) indicates that A branches off of X. Suitable spacers include peptide spacers (e.g., spacers of from about 1 to about 20 amino acids in length); non-peptide spacers, e.g., non-peptide polymers of various numbers of monomeric units, e.g., from one to about 20 units. In these embodiments, B can be present in multiple copies, either directly or in tandem.

Protein Association Moiety

The protein association moiety can be any of a variety of functional groups that provide for association of the synthetic regulator with a polypeptide or occlusion to an opening of a pore. In some embodiments, the protein association moiety can provide for association with an amino acid side chain in a polypeptide. In some embodiments, the protein association moiety can provide for association with a ligand-binding polypeptide, and with a membrane component. In other embodiments, the protein association moiety can provide for association of the synthetic regulator with a sugar residue in the polypeptide. In other embodiments, the protein association moiety can provide for association of the synthetic regulator with a moiety other than a sugar residue or an amino acid side chain. In some embodiments, the protein association moiety can comprise a reactive electrophile that can provide for association with an amino acid in the ligand-binding polypeptide. In some embodiments, the protein association moiety can comprise a reactive electrophile that can provide for association with an amino acid at or near a ligand-binding site in a ligand-binding protein. In some embodiments, the protein association moiety can provide for occlusion to an opening of a pore, such as an ion channel.

Association of the synthetic regulator with a polypeptide includes non-covalent associations such as ionic interactions, van der Waals interactions, hydrogen bonding, and the like. The association is a high-affinity association, e.g., the association between the synthetic regulator and the polypeptide has an affinity of from about $10^{-3}$ M to about $10^{-12}$ M, or greater than $10^{-12}$ M, e.g, the association between the synthetic regulator and the polypeptide has an affinity of from about $10^{-3}$ M to about $5\times10^{-3}$ M, from about $5\times10^{-3}$ M to about $10^{-4}$ M, from about $10^{-4}$ M to about $5\times10^{-4}$ M, from about $5\times10^{-4}$ M to about $10^{-5}$ M, from about $10^{-5}$ M to about $5\times10^{-5}$ M, from about $5\times10^{-5}$ M to about $10^{-6}$ M, from about $10^{-6}$ M to about $5\times10^{-6}$ M to about $10^{-7}$ M, from about $10^{-7}$ M to about $5\times10^{-7}$ M, from about $5\times10^{-7}$ M to about $10^{-8}$ M, from about $10^{-8}$ M to about $5\times10^{-4}$ M, from about $5\times10^{-8}$ M to about $10^{-9}$ M, from about $10^{-9}$ M to about $5\times10^{-9}$ M, from about $5\times10^{-9}$ M to about $10^{-10}$ M, from about $10^{-10}$ M to about $5\times10^{-10}$ M, from about $5\times10^{-10}$ M to about $10^{-11}$ M, from about $5\times10^{-11}$ M to about $10^{-12}$ M, or greater. In some embodiments, e.g., where a subject synthetic regulator comprises two or more polypeptide association moieties, each of the moieties can provide for attachment to a polypeptide with an affinity of less than about $10^{-9}$ M, but together the two or more polypeptide association moieties provide for a binding affinity that is $10^{-9}$ M or greater. In some embodiments, e.g., where a subject synthetic regulator comprises two or more polypeptide association moieties, each of the moieties can provide for attachment to a polypeptide with an affinity of less than about $10^{-4}$ M, but together the two or more polypeptide association moieties provide for a binding affinity that is $10^{-4}$ M or greater.

Occlusion of a pore by a protein association moiety can involve physically hindering access to a pore from the inside of the pore or from the outside of the pore. In some embodiments, the protein association moiety is a blocker (e.g., a pore blocker of an ion channel, or an interaction domain that binds to other biological macromolecules such as polypeptides or nucleic acids). In some embodiments, the protein association moiety can provide occlusion to pores of diameters of about 1 angstrom, 2 angstroms, 3 angstroms, or 4 angstroms. In some embodiments, the protein association moiety can provide occlusion to pores of diameters of about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 angstroms.

In certain embodiments, the polypeptide association moiety comprises a group selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —OR$^{10}$, —C(O)OR$^{10}$, —SR$^{10}$, —S(O)R$^{10}$, —S(O)$_2$R$^{10}$; wherein R$^{10}$ and R$^{11}$ are independently selected from hydrogen and C$_{1-10}$ alkyl;

R$^{12}$ is hydrogen or C$_{1-10}$ alkyl;

R$^{13}$ is selected from hydrogen, C$_{1-10}$ alkyl, C$_{1-8}$ alkenyl, C$_{6-10}$ aryl, and substituted C$_{1-10}$ alkyl.

In certain embodiments, the polypeptide association moiety comprises a group selected from hydrogen, alkyl, amino, substituted amino, and aminoacyl.

In certain embodiments, the polypeptide association moiety comprises a group selected from hydrogen, C$_{1-10}$ alkyl, substituted C$_{1-10}$ alkyl, —NR$^{10}$R$^{11}$, —NR$^{12}$C(O)R$^{13}$, C$_{2-10}$ alkenyl, substituted C$_{2-10}$ alkenyl, C$_{2-10}$ alkynyl, substituted C$_{2-10}$ alkynyl, C$_{6-20}$ aryl, substituted C$_{6-20}$ aryl, heteroaryl, heterocyclic, heterocyclooxy, heterocyclothio, heteroarylamino, heterocycloamino, C$_{4-10}$ cycloalkyl, substituted C$_{4-10}$ cycloalkyl, C$_{4-10}$ cycloalkenyl, substituted C$_{4-10}$ cycloalkenyl, cyano, halo, —OR$^{10}$, —C(O)OR$^{10}$, —SR$^{10}$, —S(O)R$^{10}$, —S(O)$_2$R$^{10}$; wherein R$^{10}$ and R$^{11}$ are independently selected from hydrogen, C$_1$-C$_{10}$ alkyl, substituted C$_1$-C$_{10}$ alkyl, C$_{2-10}$ alkenyl, substituted C$_{2-10}$ alkenyl, C$_{2-10}$ alkynyl, substituted C$_{2-10}$ alkynyl, C$_{6-20}$ aryl, substituted C$_6$-20 aryl, C$_{4-10}$ cycloalkyl, substituted C$_{4-10}$ cycloalkyl, C$_{4-10}$ cycloalkenyl, and substituted C$_{4-10}$ cycloalkenyl;

R$^{12}$ is selected from hydrogen, C$_{1-10}$ alkyl, substituted C$_{1-10}$ alkyl, C$_{2-10}$ alkenyl, substituted C$_{2-10}$ alkenyl, C$_{2-10}$ alkynyl, substituted C$_{2-10}$ alkynyl, C$_{6-20}$ aryl, substituted C$_{6-20}$ aryl, C$_{4-10}$ cycloalkyl, substituted C$_{4-10}$ cycloalkyl, C$_{4-10}$ cycloalkenyl, and substituted C$_{4-10}$ cycloalkenyl; and R$^{13}$ is selected from hydrogen, C$_{1-10}$ alkyl, substituted C$_{1-10}$ alkyl, C$_{2-10}$ alkenyl, substituted C$_{2-10}$ alkenyl, C$_{2-10}$ alkynyl, substituted C$_{2-10}$ alkynyl, C$_6$-C$_{10}$ aryl, substituted C$_{6-20}$ aryl, C$_{4-10}$ cycloalkyl, substituted C$_{4-10}$ cycloalkyl, C$_{4-10}$ cycloalkenyl, substituted C$_{4-10}$ cycloalkenyl, CH$_2$—N(CH$_2$CH$_3$)$_3{}^+$, and —CH$_2$—SO$_3{}^-$.

Figure 4:
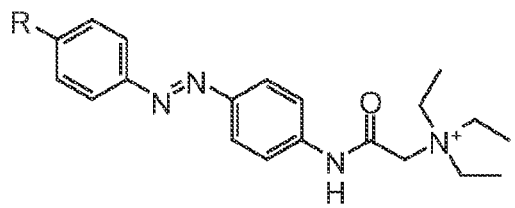
FIG. 4 provides a table of structure, potency and photoeffect of photochromic Azo-QAs on Shaker IR.

Exemplary suitable polypeptide association moieties are depicted in FIG. 4. In FIG. 4, polypeptide association moieties are designated "R."

Photoisomerizable Group

The photoisomerizable group is one that changes from a first isomeric form to a second isomeric form upon exposure to light of different wavelengths, or upon a change in exposure from dark to light, or from light to dark. For example, in some embodiments, the photoisomerizable group is in a first isomeric form when exposed to light of a first wavelength, and is in a second isomeric form when exposed to light of a second wavelength. Suitable photoisomerizable groups include stereoisomers and constitutional isomers.

The first wavelength and the second wavelength can differ from one another by from about 1 nm to about 2000 nm or more, e.g., from about 1 nm to about 10 nm, from about 10 nm to about 20 nm, from about 20 nm to about 50 nm, from about 50 nm to about 75 nm, from about 75 nm to about 100 nm, from about 100 nm to about 125 nm, from about 125 nm to about 150 nm, or from about 150 nm to about 200 nm, from about 200 nm to about 500 nm, from about 500 nm to about 800 nm, from about 800 nm to about 1000 nm, from about 1000 nm to about 1500 nm, from about 1500 nm to about 2000 nm, or more than 2000 nm.

In other embodiments, the photoisomerizable group is in a first isomeric form when exposed to light of a wavelength $\lambda_1$, and is in a second isomeric form in the absence of light (e.g., in the absence of light, the photoisomerizable group undergoes spontaneous relaxation into the second isomeric form). In these embodiments, the first isomeric form is induced by exposure to light of wavelength $\lambda_1$, and the second isomeric form is induced by not exposing the photoisomerizable group to light, e.g., keeping the photoisomerizable group in darkness. In other embodiments, the photoisomerizable group is in a first isomeric form in the absence of light, e.g., when the photoisomerizable group is in the dark; and the photoisomerizable group is in a second isomeric form when exposed to light of a wavelength $\lambda_1$. In other embodiments, the photoisomerizable group is in a first isomeric form when exposed to light of a first wavelength $\lambda_1$, and the photoisomerizable group is in a second isomeric form when exposed to light of second wavelength $\lambda_2$.

For example, in some embodiments, the photoisomerizable group is in a trans configuration in the absence of light, or when exposed to light of a first wavelength; and the photoisomerizable group is in a cis configuration when exposed to light, or when exposed to light of a second wavelength that is different from the first wavelength. As another example, in some embodiments, the photoisomerizable group is in a cis configuration in the absence of light, or when exposed to light of a first wavelength; and the photoisomerizable group is in a trans configuration when exposed to light, or when exposed to light of a second wavelength that is different from the first wavelength.

The wavelength of light that effects a change from a first isomeric form to a second isomeric form ranges from $10^{-8}$ m to about 1 m, e.g., from about $10^{-8}$ m to about $10^{-7}$ m, from about $10^{-7}$ m to about $10^{-6}$ in, from about $10^{-6}$ m to about $10^{-4}$ m, from about $10^{-4}$ in to about $10^{-2}$ m, or from about $10^{-2}$ m to about 1 m. "Light," as used herein, refers to electromagnetic radiation, including, but not limited to, ultraviolet light, visible light, infrared, and microwave.

The wavelength of light that effects a change from a first isomeric form to a second isomeric form ranges in some embodiments from about 200 nm to about 800 nm, e.g., from about 200 nm to about 250 nm, from about 250 nm to about 300 nm, from about 300 nm to about 350 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, or from about 750 nm to about 800 nm, or greater than 800 nm.

In other embodiments, the wavelength of light that effects a change from a first isomeric form to a second isomeric form ranges from about 800 nm to about 2500 nm, e.g., from about 800 nm to about 900 nm, from about 900 nm to about 1000 nm, from about 1000 nm to about 1200 nm, from about 1200 nm to about 1400 nm, from about 1400 nm to about 1600 nm, from about 1600 nm to about 1800 nm, from about 1800 nm to about 2000 nm, from about 2000 nm to about 2250 nm, or from about 2250 nm to about 2500 nm. In other embodiments, the wavelength of light that effects a change from a first isomeric form to a second isomeric form ranges from about 2 nm to about 200 nm, e.g., from about 2 nm to about 5 nm, from about 5 nm to about 10 nm, from about 10 nm to about 25 nm, from about 25 nm to about 50 nm, from about 50 nm to about 75 nm, from about 75 nm to about 100 nm, from about 100 nm to about 150 nm, or from about 150 nm to about 200 nm.

The difference between the first wavelength and the second wavelength can range from about 1 nm to about 2000 nm or more, as described above. Of course, where the synthetic light regulator is switched from darkness to light, the difference in wavelength is from essentially zero to a second wavelength.

The intensity of the light can vary from about 1 W/m$^2$ to about 50 W/m$^2$, e.g., from about 1 W/m$^2$ to about 5 W/m$^2$, from about 5 W/m$^2$ to about 10 W/m$^2$, from about 10 W/m$^2$, from about 10 W/m² to about 15 W/m², from about 15 W/m² to about 20 W/m², from about 20 W/m² to about 30 W/m², from about 30 W/m² to about 40 W/m², or from about 40 W/m² to about 50 W/m². The intensity of the light can vary from about 1 μW/cm² to about 100 μW/cm², e.g., from about 1 μW/cm² to about 5 μW/cm², from about 5 μW/cm² to about 10 μW/cm², from about 10 μW/cm² to about 20 μW/cm², from about 20 μW/cm² to about 25 μW/cm², from about 25 μW/cm² to about 50 μW/cm², from about 50 μW/cm² to about 75 μW/cm², or from about 75 μW/cm² to about 100 μW/cm². In some embodiments, the intensity of light varies from about 1 μW/mm² to about 1 W/mm², e.g., from about 1 μW/mm² to about 50 μW/mm², from about 50 μW/mm² to about 100 μW/mm², from about 100 μW/mm² to about 500 μW/mm², from about 500 μW/mm² to about 1 mW/mm², from about 1 mW/mm² to about 250 mW/mm², from about 250 mW/mm² to about 500 mW/mm², or from about 500 mW/mm² to about 1 W/mm².

In some embodiments, the change from a first isomeric form to a second isomeric form of the photoisomerizable group is effected using sound, instead of electromagnetic (EM) radiation (light). For example, in some embodiments, the change from a first isomeric form to a second isomeric form of the photoisomerizable group is effected using ultrasound.

Photoisomerizable groups are known in the art, and any known photoisomerizable group can be included in a subject synthetic regulator of protein function. Suitable photoisomerizable groups include, but are not limited to, azobenzene and derivatives thereof; spiropyran and derivatives thereof; triphenyl methane and derivatives thereof; 4,5-epoxy-2-cyclopentene and derivatives thereof; fulgide and derivatives thereof; thioindigo and derivatives thereof; diarylethene and derivatives thereof; diallylethene and derivatives thereof; overcrowded alkenes and derivatives thereof; and anthracene and derivatives thereof. In some embodiments, a suitable photoisomerizable group is a photoisomerizable group as shown in the examples herein.

Suitable spiropyran derivatives include, but are not limited to, 1,3,3-trimethylindolinobenzopyrylospiran; 1,3,3-trimethylindolino-6'-nitrobenzopyrylospiran; 1,3,3-trimethylinclolino-6'-bromobenzopyrylospiran; 1-n-decyl-3,3,3-dimethylindolino-6'-nitrobenzopyrylospiran; 1-n-octadecy-1-3,3-dimethylindolino-6'-nitrobenzopyrylospiran; 3',3'-dimethyl-6-nitro-1'-[2-(phenylcarbamoyl)ethyl]spiro; [2H-1-benzopyran-2,2'-indoline]; 1,3,3-trimethylindolino-8'-methoxybenzopyrylospiran; and 1,3,3-trimethylindolino-β-naphthopyrylospiran. Also suitable for use is a merocyanine form corresponding to spiropyran or a spiropyran derivative.

Suitable triphenylmethane derivatives include, but are not limited to, malachite green derivatives, specifically, there can be mentioned, for example, bis[dimethylamino)phenyl]phenylmethanol, bis[4-(diethylamino)phenyl]phenylmethanol, bis[4-(dibutylamino)phenyl]phenylmethanol and bis[4-(diethylamino)phenyl]phenylmethane.

Suitable 4,5-epoxy-2-cyclopentene derivatives include, for example, 2,3-diphenyl-1-indenone oxide and 2',3'-dimethyl-2,3-diphenyl-1-indenone oxide.

Suitable azobenzene compounds include, e.g., compounds having azobenzene residues crosslinked to a side chain, e.g., compounds in which 4-carboxyazobenzene is ester bonded to the hydroxyl group of polyvinyl alcohol or 4-carboxyazobenzene is amide bonded to the amino group of polyallylamine. Also suitable are azobenzene compounds having azobenzene residues in the main chain, for example, those formed by ester bonding bis(4-hydroxyphenyl)dimethylmethane (also referred to as bisphenol A) and 4,4'-dicarboxyazobenzene or by ester bonding ethylene glycol and 4,4'-dicarboxyazobenzene.

Suitable fulgide derivatives include, but are not limited to, isopropylidene fulgide and adamantylidene fulgide.

Suitable diallylethene derivatives include, for example, 1,2-dicyano-1,2-bis(2,3,5-trimethyl-4-thienyl)ethane; 2,3-bis(2,3,5-trimethyl-4-thiethyl) maleic anhydride; 1,2-dicyano-1,2-bis(2,3,5-trimethyl-4-selenyl)ethane; 2,3-bis(2,3,5-trimethyl-4-selenyl) maleic anhydride; and 1,2-dicyano-1,2-bis(2-methyl-3-N-methylindole)ethane.

Suitable diarylethene derivatives include but are not limited to, substituted perfluorocyclopentene-bis-3-thienyls and bis-3-thienylmaleimides.

Suitable overcrowded alkenes include, but are not limited to, cis-2-nitro-7-(dimethylamino)-9-(2',3'-dihydro-1'H-naphtho[2,1-b]thiopyran-1'-ylidene)-9H-thioxanthene and trans-dimethyl-[1-(2-nitro-thioxanthen-9-ylidene)-2,3-dihydro-1H-benzo[f]thiochromen-8-yl]amine. Overcrowded alkenes are described in the literature. See, e.g., terWiel et al. (2005) *Org. Biomol. Chem.* 3:28-30; and Geertsema et al. (1999) *Agnew CHem. Int. Ed. Engl.* 38:2738.

Other suitable photoisomerizable moieties include, e.g., reactive groups commonly used in affinity labeling, including diazoketones, aryl azides, diazerenes, and benzophenones.

Ligands

As used herein, the term "ligand" refers to a molecule (e.g., a small molecule, a peptide, or a protein) that binds to a polypeptide and effects a change in an activity of the polypeptide, and/or effects a change in conformation of the polypeptide, and/or affects binding of another polypeptide to the polypeptide. Ligands include agonists, partial agonists, inverse agonists, antagonists, allosteric modulators, and blockers.

In some embodiments, the ligand is a naturally-occurring ligand. In other embodiments, the ligand is a synthetic ligand. In other embodiments, the ligand is an endogenous ligand. In some embodiments, the ligand is an agonist. In other embodiments, the ligand is an inverse agonist. In other embodiments, the ligand is a partial agonist. In other embodiments, the ligand is an antagonist. In other embodiments, the ligand is an allosteric modulator. In other embodiments, the ligand is a blocker. The term "antagonist" generally refers to an agent that binds to a ligand-binding polypeptide and inhibits an activity of the ligand-binding polypeptide. An "antagonist" may be an agent that binds to an allosteric site but does not activate the ligand-binding polypeptide; instead, the antagonist generally excludes binding by an agonist and thus prevents or hinders activation. The term "blocker" refers to an agent that acts directly on the active site, pore, or allosteric site. Ligands suitable for use herein bind reversibly to a ligand-binding site of a ligand-binding polypeptide.

The ligand is selected based in part on the activity of the polypeptide to which the synthetic regulator will be attached. For example, a ligand for a hormone-binding transcription factor is a hormone, or a synthetic analog of the hormone. A ligand for a tetracycline transactivator is tetracycline or a synthetic analog thereof. A ligand for an enzyme will in some embodiments be a synthetic agonist or antagonist of the enzyme. In some embodiments, a ligand will block the ligand-binding site. A ligand for a ligand-gated ion channel will in some embodiments be a naturally-occurring ligand, or a synthetic version of the ligand, e.g., a synthetic analog of the ligand. In some embodiments, the ligand is other than an acetylcholine receptor ligand. In some embodiments, the ligand is other than trimethylammonium.

In some embodiments, a ligand is a small molecule ligand. Small molecule ligands generally have a molecular weight in a range of from about 50 daltons to about 3000 daltons, e.g., from about 50 daltons to about 75 daltons, from about 75 daltons to about 100 daltons, from about 100 daltons to about 250 daltons, from about 250 daltons to about 500 daltons, from about 500 daltons to about 750 daltons, from about 750 daltons to about 1000 daltons, from about 1000 daltons to about 1250 daltons, from about 1250 daltons to about 1500 daltons, from about 1500 daltons to about 2000 daltons, from about 2000 daltons to about 2500 daltons, or from about 2500 daltons to about 3000 daltons.

In other embodiments, a ligand is a peptide ligand. Peptide ligands can have a molecular weight in a range of from about 1 kDa to about 20 kDa, e.g., from about 1 kDa to about 2 kDa, from about 2 kDa to about 5 kDa, from about 5 kDa to about 7 kDa, from about 7 kDa to about 10 kDa, from about 10 kDa to about 12 kDa, from about 12 kDa to about 15 kDa, or from about 15 kDa to about 20 kDa.

Suitable ligands include, but are not limited to, ligands that block or activate the function of a ligand-binding protein, where ligand-binding proteins include channels; receptors (including, but not limited to, ionotropic receptors that bind transmitters; ionotropic receptors that bind hormones; metabotropic receptors; receptor tyrosine kinases; growth factor receptors; and other membrane receptors that signal by binding to soluble or membrane-bound or extracellular matrix-bound small molecules or proteins); transporters (including but not limited to ion transporters, organic molecule transporters, peptide transporters, and protein transporters); enzymes (including but not limited to kinases; phosphatases; ubiquitin ligases; acetylases; oxo-reductases; lipases; enzymes that add lipid moieties to proteins or remove them; proteases; and enzymes that modify nucleic acids, including but not limited to ligases, helicases, topoisomerases, and telomerases); motor proteins (including kinesins, dyenins and other microtubule-based motors, myosins and other actin-based motors, DNA and RNA polymerases and other motors that track along polynucleotides); scaffolding proteins; adaptor proteins; cytoskeletal proteins; and other proteins that localize or organize protein domains and superstructures within cells.

Suitable ligands include, but are not limited to, ligands that function as general anesthetics; ligands that function as local anesthetics; ligands that function as analgesics; synthetic and semi-synthetic opioid analgesics (e.g., phenanthrenes, phenylheptylamines, phenylpiperidines, morphinans, and benzomorphans) where exemplary opioid analgesics include morphine, oxycodone, fentanyl, pentazocine, hydromorphone, meperidine, methadone, levorphanol, oxymorphone, levallorphan, codeine, dihydrocodeine, hydrocodone, propoxyphene, nalmefene, nalorphine, naloxone, naltrexone, buprenorphine, butorphanol, nalbuphine, and pentazocine; ionotropic glutamate receptor agonists and antagonists, e.g., N-methyl-D-aspartate (NMDA) receptor agonists and antagonists, kainate (KA) receptor agonists and antagonists, and α-amino-3-hydroxy-5-methylisoxazole-4-propionic acid (AMPA) receptor agonists and antagonists; non-opioid analgesics, e.g., acetylsalicylic acid, choline magnesium trisalicylate, acetaminophen, ibuprofen, fenoprofen, diflusinal, and naproxen; muscarinic receptor agonists; muscarinic receptor antagonists; acetylcholine receptor agonists; acetylcholine receptor antagonists; serotonin receptor agonists; serotonin receptor antagonists; enzyme inhibitors; a benzodiazepine, e.g. chlordiazepoxide, clorazepate, diazepam, flurazepam, lorazepam, oxazepam, temazepam or triazolam; a barbiturate sedative, e.g. amobarbital, aprobarbital, butabarbital, butabital, mephobarbital, metharbital, methohexital, pentobarbital, phenobartital, secobarbital, talbutal, theamylal, or thiopental; an $H_1$ antagonist having a sedative action, e.g. diphenhydramine, pyrilamine, promethazine, chlorpheniramine, or chlorcyclizine; an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, topiramate, neramexane, or perzinfotel; an alpha-adrenergic, e.g. doxazosin, tamsulosin, clonidine, guanfacine, dexmetatomidine, modafinil, phentolamine, terazasin, prazasin or 4-amino-6,7-dimethoxy-2-(5-methane-sulfonamido-1,2,3,4-tetrahydroisoquinol-2-yl)-5-(2-pyridyl) quinazoline; a tricyclic antidepressant, e.g. desipramine, imipramine, amitriptyline, or nortriptyline; an anticonvulsant, e.g. carbamazepine, lamotrigine, topiratmate, or valproate; a tachykinin (NK) antagonist, particularly an NK-3, NK-2 or NK-1 antagonist, e.g. (α-R,9R)-7-[3,5-bis(trifluoromethyl) benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl) phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S); a muscarinic antagonist, e.g oxybutynin, tolterodine, propiverine, tropsium chloride, darifenacin, solifenacin, temiverine, or ipratropium; a cyclooxygenase-2 (COX-2) selective inhibitor, e.g. celecoxib, rofecoxib, parecoxib, valdecoxib, deracoxib, etoricoxib, or lumiracoxib; a vanilloid receptor agonist (e.g. resinferatoxin) or antagonist (e.g. capsazepine); a beta-adrenergic such as propranolol; a 5-HT receptor agonist or antagonist, e.g., a $5\text{-HT}_1B/_1D$ agonist such as eletriptan, sumatriptan, naratriptan, zolmitriptan or rizatriptan; a $5\text{-HT}_2A$ receptor antagonist such as R(+)-α-(2,3-dimethoxyphenyl)-1-[2-(4-fluorophenylethyl)]-4-piperidinemethanol (MDL-100907); and the like.

Suitable ligands for $Na^+$ channels include, but are not limited to, lidocaine, novocaine, xylocaine, lignocaine, novocaine, carbocaine, etidocaine, procaine, prontocaine, prilocalnc, bupivacaine, cinchocaine, mepivacaine, quinidine, flecamide, procaine, N-[[2'-(aminosulfonyl)biphenyl-4-yl]methyl]-N'-(2,2'-bithien-5-ylmethyl)succinamide (BPBTS), QX-314, saxitoxin, tetrodotoxin, and a type III conotoxin. Suitable ligands for $Na^+$ channels also include, but are not limited to, tetrodotoxin, saxitoxin, guanidinium, polyamines (e.g. spermine, cadaverine, putrescine, μ-conotoxin, and δ-conotoxin.

Suitable ligands for $K^+$ channels include, but are not limited to, quaternary ammonium (e.g., tetraethyl ammonium, tetrabutylammonium, tetrapentylammonium), 4-aminopyridine, sulfonylurea, Glibenclamide; Tolbutamide; Phentolamine, qiunine, qunidine, peptide toxins (e.g., charybdotoxin, agitoxin-2, apamin, dendrotoxin, VSTX1, hanatoxin-1, hanatoxin-2, and Tityus toxin K-α.

Suitable ligands for CNG and HCN channels include, but are not limited to, 1-cis diltiazem and ZD7288. Suitable ligands for glycine receptors include, but are not limited to, strychnine and picrotoxin.

Suitable ligands for nicotinic acetylcholine receptors include, but are not limited to, (+)tubocurarine, Methyllycaconitine, gallamine, Nicotine; Anatox in A, epibatidine, ABT-94, Lophotoxin, Cytisine, Hexamethonium, Mecamylamine, and Dihydro-β-erythroidine. Suitable ligands for muscarinic acetylcholine receptors include, but are not limited to, a muscarinic acetylcholine receptor antagonist as described in U.S.

Pat. No. 7,439,255; AF267B (see, e.g., U.S. Pat. No. 7,439,251); phenylpropargyloxy-1,2,5-thiadiazole-quinuclidine; carbachol; pirenzapine; migrastatin; a compound as described in U.S. Pat. No. 7,232,841; etc.

Suitable ligands for GABA receptors include, but are not limited to, Muscimol, THIP, Procabide, bicuculine, picrotoxin, gabazine, gabapentin, diazepam, clonazepam, flumazenil, a β-carboline carboxylate ethyl ester, baclofen, faclofen, and a barbiturate.

Many suitable ligands will be known to those skilled in the art; and the choice of ligand will depend, in part, on the target (e.g., receptor, ion channel, enzyme, etc.) to which the ligand binds.

Exemplary Synthetic Regulators

In some embodiments, a subject synthetic regulator is a compound having the formula: $(A)_n\text{-}X_1\text{—}(B)_m\text{—}X_2\text{—}(C)_p$, where:

A is a polypeptide association moiety that comprises a group selected from hydrogen, $C_1\text{-}C_{10}$ alkyl, substituted $C_1\text{-}C_{10}$ alkyl, $-NR^{10}R^{11}$, $-NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $-OR^{10}$, $-C(O)OR^{10}$, $-SR^{10}$, $-S(O)R^{10}$, $-S(O)_2R^{10}$; where $R^{10}$ and $R^{11}$ are independently selected from hydrogen and $C_{1-10}$ alkyl; $R^{12}$ is hydrogen or $C_{1-10}$ alkyl; $R^{13}$ is selected from hydrogen, $C_{1-10}$ alkyl, $C_{1-8}$ alkenyl, $C_{6-10}$ aryl, and substituted $C_{1-10}$ alkyl;

B is a photoisomerizable group;

C is a ligand;

each of n, m, and p is independently an integer from 1 to 10;

$X_1$, when present, is a spacer; and $X_2$, when present, is a spacer.

Suitable ligands include those described above. In some of these embodiments, the ligand is a sodium channel ligand, a synthetic ligand, a ligand that binds to a ligand binding site of an ionotropic receptor, a ligand that binds to a ligand binding site of a metabotropic receptor, a ligand that functions as an anesthetic, a potassium channel ligand, a gamma aminobutyric acid receptor ligand. In some of these embodiments, the ligand is a sodium channel ligand, a potassium channel ligand, or a gamma aminobutyric acid receptor ligand. In some of these embodiments, the ligand is an agonist, an antagonist, an allosteric modulator, or a blocker.

In some embodiments, a subject synthetic regulator is a compound having the formula: $(A)_n\text{-}X_1\text{—}(B)_m\text{—}X_2\text{—}(C)_p$, where:

A is a polypeptide association moiety that comprises a group selected from hydrogen, $C_1\text{-}C_{10}$ alkyl, substituted $C_1\text{-}C_{10}$ alkyl, $-NR^{10}R^{11}$, $-NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $-OR^{10}$, $-C(O)OR^{10}$, $SR^{10}$, $-S(O)R^{10}$, $-S(O)_2R^{10}$; where $R^{10}$ and $R^{11}$ are independently selected from hydrogen and $C_{1-10}$ alkyl; $R^{12}$ is hydrogen or $C_{1-10}$ alkyl; $R^{13}$ is selected from hydrogen, $C_{1-10}$ alkyl, $C_{1-8}$ alkenyl, $C_{6-10}$ aryl, and substituted $C_{1-10}$ alkyl;

B is a photoisomerizable group selected from an azobenzene, a fulgide, a spiropyran, a triphenyl methane, a thioindigo, a diarylethene, or an overcrowded alkene;

C is a ligand;

each of n, m, and p is independently an integer from 1 to 10;

$X_1$, when present, is a spacer; and $X_2$, when present, is a spacer.

Suitable ligands include those described above. In some of these embodiments, the ligand is a sodium channel ligand, a synthetic ligand, a ligand that binds to a ligand binding site of an ionotropic receptor, a ligand that binds to a ligand binding site of a metabotropic receptor, a ligand that functions as an anesthetic, a potassium channel ligand, a gamma aminobutyric acid receptor ligand. In some of these embodiments, the ligand is a sodium channel ligand, a potassium channel ligand, or a gamma aminobutyric acid receptor ligand. In some of these embodiments, the ligand is an agonist, an antagonist, an allosteric modulator, or a blocker.

In some embodiments, a subject synthetic regulator is a compound having the formula: $(A)_n\text{-}X_1\text{—}(B)_m\text{—}X_2\text{—}(C)_p$, where:

A is a polypeptide association moiety that comprises a group selected from hydrogen, $C_{1-10}$ alkyl, substituted $C_{1-10}$ alkyl, $-NR^{10}R^{11}$, $-NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, $-OR^{10}$, $-C(O)OR^{10}$, $-SR^{10}$, $-S(O)R^{10}$, $-S(O)_2R^{10}$; where $R^{10}$ and $R^{11}$ are independently selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl; $R^{12}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$cycloalkyl, $C_{4-10}$ cycloalkyl, substituted $C_{4-10}$ cycloalkyenyl, and substituted $C_{4-10}$ cycloalkenyl; and $R^{13}$ is selected from hydrogen, $C_{1-10}$ alkyl, substituted $C_{1-10}$ alkyl. $C_{2-10}$ alkenyl, substituted $C_{2-10}$ alkenyl, $C_{2-10}$ alkynyl, substituted $C_{2-10}$ alkynyl, $C_6\text{-}C_{10}$ aryl, substituted $C_{6-20}$ aryl, $C_{4-10}$ cycloalkyl, substituted $C_{4-10}$ cycloalkyl, $C_{4-10}$ cycloalkenyl, substituted $C_{4-10}$ cycloalkenyl, $CH_2-N(CH_2CH_3)_3^+$, and $-CH_2-SO_3^-$;

B is a photoisomerizable group;

C is a ligand;

each of n, m, and p is independently an integer from 1 to 10;

$X_1$, when present, is a spacer; and $X_2$, when present, is a spacer.

Suitable ligands include those described above. In some of these embodiments, the ligand is a sodium channel ligand, a synthetic ligand, a ligand that binds to a ligand binding site of an ionotropic receptor, a ligand that binds to a ligand binding site of a metabotropic receptor, a ligand that functions as an anesthetic, a potassium channel ligand, a gamma aminobutyric acid receptor ligand. In some of these embodiments, the ligand is a sodium channel ligand, a potassium channel ligand, or a gamma aminobutyric acid receptor ligand. In some of these embodiments, the ligand is an agonist, an antagonist, an allosteric modulator, or a blocker.

In some embodiments, a subject synthetic regulator is a compound having the formula: $(A)_n\text{-}X_1\text{—}(B)_m\text{—}X_2\text{—}(C)_p$, wherein:

A is a polypeptide association moiety that comprises a group selected from hydrogen, $C_{1-10}$ alkyl, substituted $C_{1-10}$ alkyl, $-NR^{10}R^{11}$, $-NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —OR$^{10}$, —C(O)OR$^{10}$, —SR$^{10}$, —S(O)R$^{10}$, —S(O)$_2$R$^{10}$; where R$^{10}$ and R$^{11}$ are independently selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl; R$^{12}$ is selected from hydrogen, $C_{1-10}$ alkyl, substituted $C_{1-14}$ alkyl, $C_{2-10}$ alkenyl, substituted $C_{2-10}$ alkenyl, $C_{2-10}$ alkynyl, substituted $C_{2-10}$ alkynyl, $C_{5-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl; and R$^{13}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_6$-$C_{10}$ aryl, substituted $C_{6-20}$ aryl, $C_{4-10}$ cycloalkyl, substituted $C_{4-10}$ cycloalkyl, $C_{4-10}$ cycloalkenyl, substituted $C_{4-10}$ cycloalkenyl, —CH$_2$—N(CH$_2$CH$_3$)$_3^+$, and —CH$_2$—SO$_3^-$;

B is a photoisomerizable group selected from an azobenzene, a fulgide, a spiropyran, a triphenyl methane, a thioindigo, a diarylethene, or an overcrowded alkene;

C is a ligand;

each of n, m, and p is independently an integer from 1 to 10;

X$_1$, when present, is a spacer; and

X$_2$, when present, is a spacer.

Suitable ligands include those described above. In some of these embodiments, the ligand is a sodium channel ligand, a synthetic ligand, a ligand that binds to a ligand binding site of an ionotropic receptor, a ligand that hinds to a ligand binding site of a metabotropic receptor, a ligand that functions as an anesthetic, a potassium channel ligand, a gamma aminobutyric acid receptor ligand. In some of these embodiments, the ligand is a sodium channel ligand, a potassium channel ligand, or a gamma aminobutyric acid receptor ligand. In some of these embodiments, the ligand is an agonist, an antagonist, an allosteric modulator, or a blocker.

In certain embodiments, a subject synthetic regulator functions as a blocker (e.g., a potassium channel blocker, and/or a sodium channel blocker and/or a calcium channel blocker) in the cis-isomeric form. In other embodiments, a subject synthetic regulator functions as a blocker (e.g., a potassium channel blocker, and/or a sodium channel blocker and/or a calcium channel blocker) in the trans-isomeric form.

In some embodiments, a subject synthetic regulator of polypeptide function is a compound of Formula XI:

wherein Q$^1$ is CH$_2$— or —C(=O)—;

Q$^2$ is

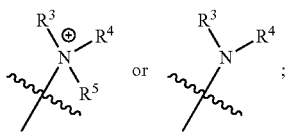

each of R$^1$ are independently selected from hydrogen, $C_{1-10}$ alkyl, substituted $C_{1-10}$ alkyl, —NR$^{10}$R$^{11}$, —NR$^{12}$C(O)R$^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{5-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —OR$^{10}$, —C(O)OR$^{10}$, —S(O)R$^{10}$, —S(O)$_2$R$^{10}$;

x is an integer from 1 to 5;

y is an integer from 1 to 4;

R$^2$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

R$^3$, R$^4$, and R$^5$ are independently selected from hydrogen, $C_2$-$C_1$ alkyl, substituted $C_2$-$C_{10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_6$-20 aryl, $C_{4-10}$ cycloalkyl, substituted $C_{4-10}$ cycloalkyl, $C_{4-10}$ cycloalkenyl, and substituted $C_{4-10}$ cycloalkenyl;

each of R$^6$ are independently selected from hydrogen, $C_{1-10}$ alkyl, substituted $C_{1-10}$ alkyl, —NR$^{10}$R$^{11}$, —NR$^{12}$C(O)R$^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —OR$^{10}$, —C(O)OR$^{10}$, SR$^{10}$, —S(O)R$^{10}$, —S(O)$_2$R$^{10}$;

R$^{10}$ and R$^{11}$ are independently selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ substituted $C_{6-20}$ alkynyl, $C_{6-20}$ aryl, aryl, $C_{4-10}$ cycloalkyl, substituted $C_{4-10}$ cycloalkyl, $C_{4-10}$ cycloalkenyl, and substituted $C_{4-10}$ cycloalkenyl;

R$^{12}$ is selected from hydrogen, $C_{1-10}$ alkyl, substituted $C_{1-10}$ alkyl, $C_{2-10}$ alkenyl, substituted $C_{2-40}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

R$^{13}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_6$-$C_{10}$ aryl, substituted $C_{6-20}$ aryl, $C_{4-10}$ cycloalkyl, substituted $C_{4-10}$ cycloalkyl, $C_{4-10}$ cycloalkenyl, substituted $C_{4-10}$ cycloalkenyl, —CH$_2$—N(CH$_2$CH$_3$)$_3^+$, and —CH$_2$—SO$_3^-$;

or a pharmaceutically acceptable salt thereof.

In some embodiments, a subject synthetic regulator of polypeptide function is a compound of Formula XII:

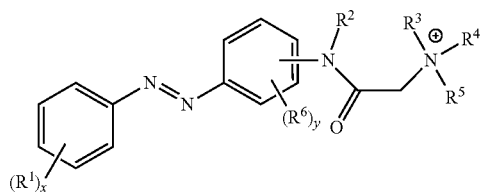

(Formula XII)

wherein each of R$^1$ are independently selected from hydrogen, $C_{1-10}$ alkyl, substituted $C_{1-10}$ alkyl, —NR$^{10}$R$^{11}$, NR$^{12}$C(O)R$^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —OR$^{10}$, —C(O)OR$^{10}$, SR$^{10}$, —S(O)R$^{10}$, —S(O)$_2$R$^{10}$;

x is an integer from 1 to 5;

y is an integer from 1 to 4;

R$^2$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

$R^3$, $R^4$, and $R^5$ are independently selected from hydrogen, $C_{2-8}$ alkyl, substituted $C_{2-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

each of $R^6$ are independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-2}$ aryl, substituted $C_{6-2}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{5-20}$ aryl, $C_{4-10}$ cycloalkyl, substituted $C_{4-10}$ cycloalkyl, $C_{4-10}$ cycloalkenyl, and substituted $C_{4-10}$ cycloalkenyl;

$R^{12}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-21}$) aryl, $C_{4-10}$ cycloalkyl, substituted $C_{4-10}$ cycloalkyl, $C_{4-10}$ cycloalkenyl, and substituted $C_{4-10}$ cycloalkenyl;

$R^{13}$ is selected from hydrogen, $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, $C_6-C_{10}$ aryl, substituted $C_{6-20}$ aryl, $C_{4-10}$ cycloalkyl, substituted $C_{4-10}$ cycloalkyl, $C_{4-10}$ cycloalkenyl, substituted $C_{4-10}$ cycloalkenyl, —$CH_2$—$N(CH_2CH_3)_3^+$, and —$CH_2$—$SO_3^-$;

or a pharmaceutically acceptable salt thereof.

In certain embodiments of Formula XL $Q^1$ is —$CH_2$—. In certain embodiments of Formula XI, $Q^1$ is —$C(=O)$—.

In certain embodiments of Formula XI, $Q^2$ is

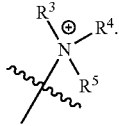

In certain embodiments of Formula XI, $Q^2$ is

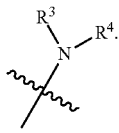

In certain embodiments of any one of the above Formulae XI and XII, $R^3$, $R^4$, and $R^5$ are $C_{2-10}$ alkyl. In certain embodiments of any one of the above Formulae XI and XII, $R^3$, $R^4$, and $R^5$ are $C_{2-5}$ alkyl. In certain embodiments of any one of the above Formulae XI and XII, $R^3$, $R^4$, and $R^5$ are $C_2$ alkyl. In certain embodiments of any one of the above Formulae XI and XII, $R^3$, $R^4$, and $R^5$ are $C_3$ alkyl. In certain embodiments of any one of the above Formulae XI and XII, $R^3$, $R^4$, and $R^5$ are $C_4$ alkyl. In certain embodiments of Formulae XI and XII, $R^3$, $R^4$, and $R^5$ are hydrogen.

In certain embodiments of any one of the above Formulae XI and XII, $R^3$, $R^4$, and $R^5$ are independently selected from $C_{2-8}$ alkyl or substituted $C_{2-8}$ alkyl. In certain embodiments of any one of the above Formulae XI and XII, $R^3$, $R^4$, and $R^5$ are independently selected from $C_{2-10}$ alkenyl, substituted $C_{2-10}$ alkenyl, $C_{2-10}$ alkynyl, substituted $C_{2-10}$ alkynyl. In certain embodiments of any one of the above Formulae XI and XII, $R^3$, $R^4$, and $R^5$ are independently selected from $C_{6-20}$ aryl or substituted $C_{6-20}$ aryl. In certain embodiments of any one of the above Formulae XI and XII, $R^3$, $R^4$, and $R^5$ are independently selected from $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae XI and XII, $R^2$ is hydrogen. In certain embodiments of any one of the above Formulae XI and XII, $R^2$ is $C_{1-10}$ alkyl. In certain embodiments of any one of the above Formulae XI and XII, $R^2$ is $C_{1-5}$ alkyl. In certain embodiments of any one of the above Formulae XI and XII, $R^2$ is hydrogen or $C_{1-5}$ alkyl.

In certain embodiments of any one of the above Formulae XI and XII, $R^2$ is $C_{1-10}$ alkyl or substituted $C_{1-10}$ alkyl. In certain embodiments of any one of the above Formulae XI and XII, $R^2$ is $C_{2-10}$ alkenyl, substituted $C_{2-10}$ alkenyl, $C_{2-10}$ alkynyl, substituted $C_{2-10}$ alkynyl. In certain embodiments of any one of the above Formulae XI and XII, $R^2$ is $C_{6-20}$ aryl or substituted $C_{6-20}$ aryl. In certain embodiments of any one of the above Formulae XI and XII, $R^2$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae XI and XII, at least one of $R^6$ is $C_{1-10}$ alkyl, substituted $C_{1-10}$ alkyl, or halo. In certain embodiments of any one of the above Formulae XI and XII, at least one of $R^6$ is $C_{1-4}$ alkyl. In certain embodiments of any one of the above Formulae XI and XII, at least one of $R^6$ is halo.

In certain embodiments of any one of the above Formulae XI and XII, at least one of $R^6$ is —$NR^{10}R^{11}$ or —$NR^{12}C(O)R^{13}$. In certain embodiments of any one of the above Formulae XI and XII, at least one of $R^6$ is $C_{2-10}$ alkenyl, substituted $C_{2-10}$ alkenyl, $C_{2-10}$ alkynyl, or substituted $C_{2-10}$ alkynyl. In certain embodiments of any one of the above Formulae XI and XII, at least one of $R^6$ is $C_{6-20}$ aryl, substituted $C_{6-20}$ aryl, heteroaryl, or heterocyclic. In certain embodiments of any one of the above Formulae XI and XII, at least one of $R^6$ is heterocyclooxy, heterocyclothio, heteroarylamino, or heterocycloamino. In certain embodiments of any one of the above Formulae XI and XII, at least one of $R^6$ is $C_{4-10}$ cycloalkyl, substituted $C_{4-10}$ cycloalkyl, $C_{4-10}$ cycloalkenyl, or substituted $C_{4-10}$ cycloalkenyl. In certain embodiments of any one of the above Formulae XI and XII, at least one of $R^6$ is cyano, halo, —$OR^{10}$, —$C(O)OR^{10}$, —$SR^{10}$, —$S(O)R^{10}$, or —$S(O)_2R^{10}$.

In certain embodiments of any one of the above Formulae XI and XII, at least one of $R^1$ is hydrogen.

In certain embodiments of any one of the above Formulae XI and XII, at least one of $R^1$ is $C_{1-8}$ alkyl, e.g., $C_{1-6}$ alkyl, $C_{1-5}$ alkyl or $C_{1-4}$ alkyl. In some embodiments of any one of the above Formulae XI and XII, at least one of $R^1$ is $C_{1-4}$ alkyl.

In certain embodiments of any one of the above Formulae XI and XII, at least one of $R^1$ is —$NR^{12}C(O)R^{13}$.

In certain embodiments of any one of the above Formulae XI and XII, at least one of $R^1$ is —$NR^{10}R^{11}$.

In certain embodiments of any one of the above Formulae XI and XII, at least one of $R^1$ is $C_{1-10}$ alkyl or substituted $C_{1-10}$ alkyl.

In certain embodiments of any one of the above Formulae XI and XII, at least one of $R^1$ is $C_{2-10}$ alkenyl, substituted $C_{2-10}$ alkenyl, $C_{2-10}$ alkynyl, or substituted $C_{2-10}$ alkynyl. In certain embodiments of any one of the above Formulae XI and XII, at least one of $R^1$ is $C_{6-20}$ aryl or substituted $C_{6-20}$ aryl. In certain embodiments of any one of the above Formulae XI and XII, at least one of $R^1$ is heteroaryl, heterocyclic, heterocyclooxy, heterocyclothio, heteroarylamino, or heterocycloamino. In certain embodiments of any one of the above Formulae XI and XII, at least one of $R^1$ is $C_{4-10}$ cycloalkyl, substituted $C_{4-10}$ cycloalkyl, $C_{4-10}$ cycloalkenyl, or substituted $C_{4-10}$ cycloalkenyl. In certain embodiments of any one of the above Formulae XI and XII, at least one of Fe is cyano, halo, —$OR^{10}$, —$C(O)OR^{10}$, —$S(O)R^{10}$, —$S(O)_2R^{10}$.

In certain embodiments of any one of the above Formulae XI and XII, $R^{12}$ is hydrogen. In certain embodiments of any one of the above Formulae XI and XII, $R^{12}$ is $C_{1-10}$ alkyl. In certain embodiments of any one of the above Formulae XI and XII, $R^{12}$ is $C_{1-10}$ alkyl. In certain embodiments of any one of the above Formulae XI and XII, $R^{12}$ is hydrogen or $C_{1-5}$ alkyl.

In certain embodiments of any one of the above Formulae XI and XII, $R^{12}$ is hydrogen. In certain embodiments of any one of the above Formulae XI and XII, $R^{12}$ is $C_{1-10}$ alkyl or substituted $C_{1-10}$ alkyl. In certain embodiments of any one of the above Formulae XI and XII, $R^{12}$ is $C_{2-10}$ alkenyl, substituted $C_{2-10}$ alkenyl, $C_{2-10}$ alkynyl, or substituted $C_{2-10}$ alkynyl. In certain embodiments of any one of the above Formulae XI and XII, $R^{12}$ is $C_{6-20}$ aryl or substituted $C_{6-20}$ aryl. In certain embodiments of any one of the above Formulae XI and XII, $R^{12}$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae XI and XII, $R^{13}$ is hydrogen or $C_{1-10}$ alkyl. In certain embodiments of any one of the above Formulae XI and XII, $R^{13}$ is $C_{1-10}$ alkyl. In certain embodiments of any one of the above Formulae XI and $X_{11}$, $R^{13}$ is $C_{1-5}$ alkyl. In certain embodiments of any one of the above Formulae XI and XII, $R^{13}$ is hydrogen or $C_{1-5}$ alkyl.

In certain embodiments of any one of the above Formulae XI and XII, $R^{13}$ is alkenyl or substituted alkenyl. In certain embodiments of any one of the above Formulae XI and XII, $R^{13}$ is $C_{1-10}$ alkenyl. In certain embodiments of any one of the above Formulae XI and XII, $R^{13}$ is $C_{1-5}$ alkenyl. In certain embodiments of any one of the above Formulae XI and XII, $R^{13}$ is hydrogen or $C_{1-5}$ alkenyl.

In certain embodiments of any one of the above Formulae XI and XII, $R^{13}$ is $C_6$ aryl or substituted $C_6$ aryl.

In certain embodiments of any one of the above Formulae XI and XII, $R^{13}$ is —$CH_2$—$N(CH_2CH_3)_3^+$ or —$CH_2$—$SO_3^-$. In certain embodiments of any one of the above Formulae XI and XII, $R^{13}$ is —$CH_2$—$N(CH_2CH_3)_3^+$. In certain embodiments of any one of the above Formulae XI and XII, $R^{13}$ is or —$CH_2$—$SO_3^-$.

In certain embodiments of any one of the above Formulae XI and XII, $R^{13}$ is hydrogen. In certain embodiments of any one of the above Formulae XI and XII, $R^{13}$ is $C_{1-10}$ alkyl or substituted $C_{1-10}$ alkyl. In certain embodiments of any one of the above Formulae XI and XII, $R^{13}$ is $C_{2-10}$ alkenyl or substituted $C_{2-10}$ alkenyl. In certain embodiments of any one of the above Formulae XI and XII, $R^{13}$ is $C_{2-10}$ alkynyl or substituted $C_{2-10}$ alkynyl. In certain embodiments of any one of the above Formulae XI and XII, $R^{13}$ is $C_{6-10}$ aryl or substituted $C_{6-20}$ aryl. In certain embodiments of any one of the above Formulae XI and XII, $R^{13}$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae XI and XII, at least one of $R^{10}$ and $R^{11}$ is hydrogen. In certain embodiments of any one of the above Formulae XI and XII, at least one of $R^{10}$ and $R^{11}$ is $C_{1-10}$ alkyl or substituted $C_{1-10}$ alkyl. In certain embodiments of any one of the above Formulae XI and XII, at least one of $R^{10}$ and $R^{11}$ is $C_{2-10}$ alkenyl, substituted $C_{2-10}$ alkenyl, $C_{2-10}$ alkynyl, or substituted $C_{2-10}$ alkynyl. In certain embodiments of any one of the above Formulae XI and XII, at least one of $R^{10}$ and $R^{11}$ is $C_{6-20}$ aryl or substituted $C_{6-20}$ aryl. In certain embodiments of any one of the above Formulae XI and XII, at least one of $R^{10}$ and $R^{11}$ is $C_{4-10}$ cycloalkyl, substituted $C_{4-10}$ cycloalkyl, $C_{4-10}$ cycloalkenyl, or substituted $C_{4-10}$ cycloalkenyl.

In certain embodiments of any one of the above Formulae XI and XII, at least one of $R^{10}$ and $R^{11}$ is $C_{1-10}$ alkyl. In certain embodiments of any one of the above Formulae XI and XII, at least one of $R^{10}$ and $R^{11}$ is $C_{2-5}$ alkyl. In certain embodiments of any one of the above Formulae XI and XII, at least one of $R^{10}$ and $R^{11}$ is $C_2$ alkyl. In certain embodiments of any one of the above Formulae XI and XII, at least one of $R^{10}$ and $R^{11}$ is $C_3$ alkyl. In certain embodiments of any one of the above Formulae XI and XII, at least one of $R^{10}$ and $R^{11}$ is $C_4$ alkyl.

In certain embodiments of any one of the above Formulae XI and XII, at least one of $R^{10}$ and $R^{11}$ is alkyl substituted with aryl, aryloxy, heteroaryl, heteroaryloxy, heterocyclic, or heterocyclooxy. In certain embodiments of any one of the above Formulae XI and XII, at least one of $R^{10}$ and $R^{11}$ is alkyl substituted with aryl, heteroaryl, or heterocyclic. In certain embodiments of any one of the above Formulae XI and XII, at least one of $R^{10}$ and $R^{11}$ is alkyl substituted with aryl. In certain embodiments of any one of the above Formulae XI and XII, at least one of $R^{10}$ and $R^{11}$ is alkyl substituted with heteroaryl. In certain embodiments of any one of the above Formulae XI and XII, at least one of $R^{10}$ and $R^{11}$ is alkyl substituted with heterocyclic.

In some embodiments, a subject synthetic regulator of polypeptide function is a compound of Formula I:

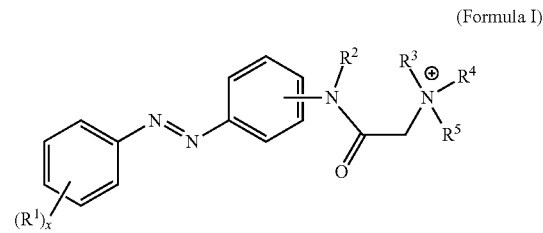

(Formula I)

wherein each of $R^1$ are independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, $SR^{10}$, —$S(O)R^{10}$, —$S(O)_2R^{10}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some embodiments, a subject synthetic regulator of polypeptide function is a compound of Formula II:

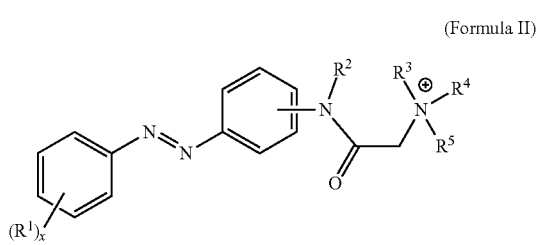
(Formula II)

wherein each of $R^1$ are independently selected from hydrogen, $C_{1-10}$ alkyl, $-NR^{10}R^{11}$, $-NR^{12}C(O)R^{13}$, $C_{2-10}$ alkenyl, $C_{2-10}$ alkynyl, cyano, halo, $-OR^{10}$, $-C(O)OR^{10}$, $-SR^{10}$, $-S(O)R^{10}$, $-S(O)_2R^{10}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some embodiments, a subject synthetic regulator of polypeptide function is a compound of Formula III:

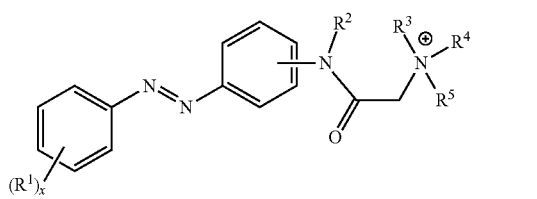
(Formula III)

wherein each of $R^1$ are independently selected from hydrogen, $C_{1-10}$ alkyl, $-NR^{10}R^{11}$, and $-NR^{12}C(O)R^{13}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some embodiments, a subject synthetic regulator of polypeptide function is a compound of Formula IV:

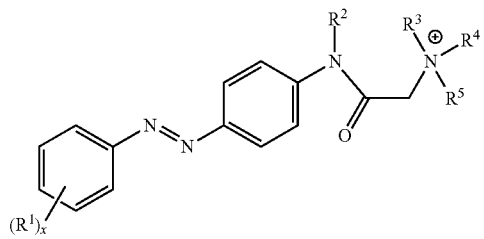
(Formula IV)

wherein each of $R^1$ are independently selected from hydrogen, $C_{1-10}$ alkyl, $-NR^{10}R^{11}$, and $-NR^{12}C(O)R^{13}$;

x is an integer from 1 to 5;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some embodiments, a subject synthetic regulator of polypeptide function is a compound of Formula V:

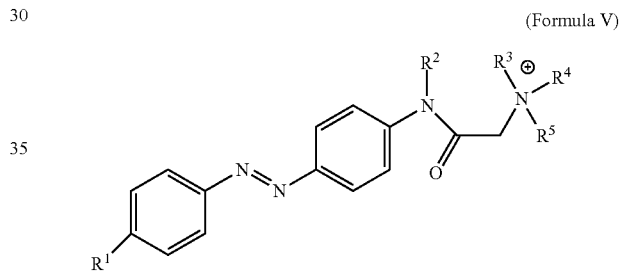
(Formula V)

wherein $R^1$ is selected from hydrogen, $C_{1-10}$ alkyl, $-NR^{10}R^{11}$, and $-NR^{12}C(O)R^{13}$;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some embodiments, a subject synthetic regulator of polypeptide function is a compound of Formula VI:

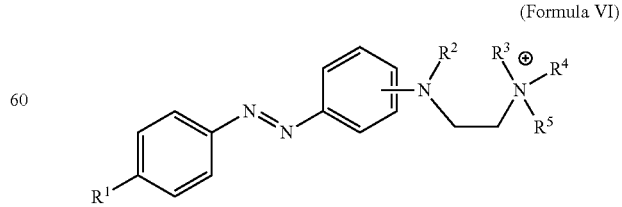
(Formula VI)

wherein $R^1$ is selected from hydrogen, $C_{1-10}$ alkyl, substituted $C_{1-10}$ alkyl, $-NR^{10}R^{11}$, $-NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^2$ is hydrogen or $C_{1-10}$ alkyl;

$R^3$, $R^4$, and $R^5$ are independently selected from hydrogen and $C_{2-8}$ alkyl;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof. In some embodiments, a compound of Formula VI has no carbonyl group.

In some embodiments, a subject synthetic regulator of polypeptide function is a compound of Formula VII:

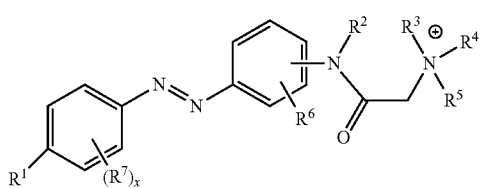

(Formula VII)

wherein $R^1$ is selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 4;

$R^2$ is hydrogen or $C_{1-10}$ alkyl;

$R^3$, $R^4$, and $R^5$ are independently selected from hydrogen and $C_{2-8}$ alkyl;

each of $R^6$ and $R^7$ are independently selected from hydrogen. $C_{1-10}$ alkyl, substituted $C_{1-10}$ alkyl, —$NR^{10}R^{11}$; —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some embodiments, a subject synthetic regulator of polypeptide function is a compound of Formula VIII:

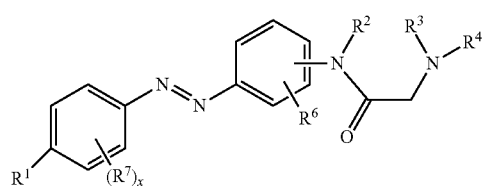

(Formula VIII)

wherein $R^1$ is selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 4;

$R^2$ is hydrogen or $C_{1-10}$ alkyl;

$R^3$ and $R^4$ are independently selected from hydrogen and $C_{2-8}$ alkyl;

each of $R^6$ and $R^7$ are independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof. In some embodiments, the nitrogen is not permanently charged.

In some embodiments, a subject synthetic regulator of polypeptide function is a compound of Formula IX:

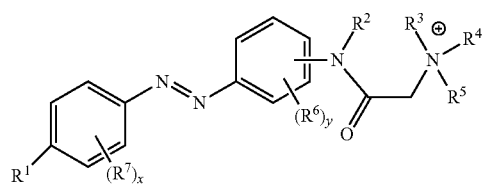

(Formula IX)

wherein $R^1$ is selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, cycloalkyl, substituted $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 4;

y is an integer from 1 to 4;

$R^2$ is hydrogen or $C_{1-10}$ alkyl;

$R^3$, $R^4$, and $R^5$ are independently selected from hydrogen and $C_{2-8}$ alkyl;

each of $R^6$ and $R^7$ are independently selected from hydrogen, $C_{1-10}$ alkyl, substituted $C_{1-10}$ alkyl, $NR^{10}R^{11}$, —$NR^{12}C(O)R^{13}$, $C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In some embodiments, a subject synthetic regulator of polypeptide function is a compound of Formula X:

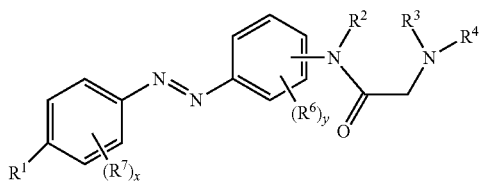

(Formula X)

wherein $R^1$ is selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

x is an integer from 1 to 4;

y is an integer from 1 to 4;

$R^2$ is hydrogen or $C_{1-10}$ alkyl;

$R^3$ and $R^4$ are independently selected from hydrogen and $C_{2-8}$ alkyl;

each of $R^6$ and $R^7$ are independently selected from hydrogen, $C_{1-10}$ alkyl, substituted $C_{1-10}$ alkyl, —$NR^{10}R^{11}$, —$NR^{12}C(O)R^{13}$, $C_{2-10}$ alkenyl, substituted $C_{2-10}$ alkenyl, $C_{2-10}$ alkynyl, substituted $C_{2-10}$ alkynyl, $C_{6-20}$ aryl, substituted $C_{6-20}$ aryl, heteroaryl, heterocyclic, heterocyclooxy, heterocyclothio, heteroarylamino, heterocycloamino, $C_{4-10}$ cycloalkyl, substituted $C_{4-10}$ cycloalkyl, $C_{4-10}$ cycloalkenyl, substituted $C_{4-10}$ cycloalkenyl, cyano, halo, —$OR^{10}$, —$C(O)OR^{10}$, —$SR^{10}$, —$S(O)R^{10}$, —$S(O)_2R^{10}$;

$R^{10}$ and $R^{11}$ are independently selected from hydrogen and $C_{1-10}$ alkyl;

$R^{12}$ is hydrogen or $C_{1-10}$ alkyl;

$R^{13}$ is selected from hydrogen, $C_{1-10}$ alkyl, $C_{1-8}$ alkenyl, $C_{6-10}$ aryl, and substituted $C_{1-10}$ alkyl, or a pharmaceutically acceptable salt thereof.

In certain embodiments of any one of the above Formulas I-X, $R^2$ is hydrogen. In certain embodiments of any one of the above Formulas I-X, $R^2$ is $C_{1-10}$ alkyl. In certain embodiments of any one of the above Formulas I-X, $R^2$ is $C_{1-5}$ alkyl. In certain embodiments of any one of the above Formulas I-X, $R^2$ is hydrogen or $C_{1-5}$ alkyl.

In certain embodiments of any one of the above Formulas I-X, $R^1$ is hydrogen.

In certain embodiments of any one of the above Formulas I-X, $R^1$ is $C_{1-8}$ alkyl, e.g., $C_{1-6}$ alkyl, $C_{1-5}$ alkyl or $C_{1-4}$ alkyl. In some embodiments of any one of the above Formulas I-X, $R^1$ is $C_{1-4}$ alkyl.

In certain embodiments of any one of the above Formulas I-X, $R^1$ is —$NR^{12}C(O)R^{13}$.

In certain embodiments of any one of the above Formulas I-X, $R^{12}$ is hydrogen. In certain embodiments of any one of the above Formulas I-X, $R^{12}$ is $C_{1-10}$ alkyl. In certain embodiments of any one of the above Formulas I-X, $R^{12}$ is $C_{1-5}$ alkyl. In certain embodiments of any one of the above Formulas I-X, $R^{12}$ is hydrogen or $C_{1-5}$ alkyl.

In certain embodiments of any one of the above Formulas I-X, $R^{13}$ is hydrogen or $C_{1-10}$ alkyl. In certain embodiments of any one of the above Formulas I-X, $R^{13}$ is $C_{1-10}$ alkyl. In certain embodiments of any one of the above Formulas I-X, $R^{13}$ is $C_{1-5}$ alkyl. In certain embodiments of any one of the above Formulas I-X, $R^{13}$ is hydrogen or $C_{1-5}$ alkyl.

In certain embodiments of any one of the above Formulas I-X, $R^{13}$ is alkenyl or substituted alkenyl. In certain embodiments of any one of the above Formulas I-X, $R^{13}$ is alkenyl. In certain embodiments of any one of the above Formulas I-X, $R^{13}$ is $C_{1-5}$ alkenyl. In certain embodiments of any one of the above Formulas I-X, $R^{13}$ is hydrogen or $C_{1-5}$ alkenyl.

In certain embodiments of any one of the above Formulas I-X, $R^{13}$ is $C_6$ aryl or substituted $C_6$ aryl.

In certain embodiments of any one of the above Formulas I-X, $R^{13}$ is alkyl substituted with $SO_3H$, —$SO_3^-$, —$NR_aR_b$, —$N^+R_aR_bR_c$, wherein $R_a$, $R_b$, and $R_c$ may be the same or different and are chosen from hydrogen, optionally substituted alkyl, cycloalkyl, alkenyl, cycloalkenyl, alkynyl, aryl, heteroaryl and heterocyclic. In certain embodiments of any one of the above Formulas I-X, $R^{13}$ is alkyl substituted with $SO_3H$ or —$SO_3^-$. In certain embodiments of any one of the above Formulas I-X, $R^{13}$ is alkyl substituted with —$NR_aR_b$ or —$N^+R_aR_bR_c$. In certain embodiments of any one of the above Formulas I-X, $R^{13}$ is alkyl substituted with —$NR_aR_b$ or —$N^+R_aR_bR_c$, and wherein $R_a$, $R_b$, and $R_c$ may be the same or different and are chosen from hydrogen and optionally substituted alkyl. In certain embodiments of any one of the above Formulas I-X, $R^{13}$ is alkyl substituted with —$NR_aR_b$ or —$N^+R_aR_bR_c$, and wherein $R_a$, $R_b$, and $R_c$ are alkyl.

In some embodiments, a subject synthetic regulator is a non-permanently charged compound. In some embodiments, a subject synthetic regulator comprises a substituted azobenzene group. In some embodiments, a subject synthetic regulator is a cis blocker, e.g., blocks a receptor (such as an ion channel) when in the cis isomeric form. In other embodiments, a subject synthetic regulator is a trans-blocker blocker, e.g., blocks a receptor (such as an ion channel) when in the trans isomeric form.

In some embodiments, a subject synthetic regulator acts on more than one polypeptide. For example, QAQ blocks voltage-gated potassium channels ($K_v$), voltage-gated sodium channels ($Na_v$), and voltage-gated calcium channels ($Ca_v$) channels. In other embodiments, a subject synthetic regulator exhibits selectivity, e.g., in some embodiments, a subject synthetic regular selectively blocks a voltage-gated potassium channel, but does not substantially block a voltage-gated sodium channel or a voltage-gated calcium channel.

In some embodiments, a subject synthetic regulator comprises a red-shifted photoisomerizable group, e.g., the photoisomerizable group of a synthetic regulator is in a first isomeric form when exposed to a first wavelength of light, and is in a second isomeric form when exposed to a second wavelength of light, where the second wavelength is shifted toward the red end of the spectrum compared to the first wavelength of light. As an example, DAAQ is in a first isomeric form at 472 nm and in a second isomeric form at 550 nm.

In some embodiments, a subject synthetic regulator is membrane permeant, e.g., will cross a eukaryotic cell membrane without the need for any additional physical, electrical, or chemical stimulus to be applied to the cell.

In some embodiments, a subject synthetic regulator is membrane impermeant; for example, in some embodiments, a subject synthetic regulator enters a eukaryotic cell only upon application of an additional physical, electrical, or chemical stimulus to the cell. For example, in some embodiments, a subject synthetic regulator enters a eukaryotic cell (e.g., a neuron) only upon application of a physical, electrical, or chemical stimulus that activates a nonselective ion channel. Nonselective ion channels include, e.g., ligand-gated nonselective cation channels. Nonselective cation channels include, e.g., TRPV$_1$, P2X$_7$R, and the like. P2X$_7$R (or P2X purinoceptor 7) is described in, e.g., Chessell et al. (2005) *Pain* 114:386; and Rassendren et al. (1997) *J. Biol. Chem.* 272:5482. P2X$_7$R can be activated by adenosine triphosphate (ATP), or an ATP analog. An example of a membrane-impermeant synthetic regulator is QAQ.

TRPV$_1$ (transient receptor potential cation channel, subfamily V, member 1; also known as vanilloid receptor type 1), is a ligand-gated nonselective cation channel that is activated by a variety of endogenous and exogenous physical and chemical stimuli, including, e.g., heat over 43° C., low pH, the endocannabinoid anandamide, N-arachidonoyl-dopamine, and capsaicin. For TRPV$_1$, see, e.g., Cui et al. (2006) *J. Neurosci.* 26:9385.

TRPV$_1$ agonists include, e.g., capsaicin; a capsaicinoid (where capsaicinoids include, e.g., capsiate (4-hydroxy-3-methoxybenzyl (E)-8-methyl-6-nonenoate); dihydrocapsiate (4-hydroxy-3-methoxybenzyl 8-methylnonanoate); nordihydrocapsiate (4-hydroxy-3-methoxybenzyl 7-methyl-octanoate); capsiate derivatives such as vanillyl decanoate, vanillyl nonanoate, vanillyl octanoate and the like; fatty acid esters of vanillyl alcohol; and various straight chain or branched chain fatty acids which have a fatty acid chain length similar to that of nordihydrocapsiate); resiniferatoxin; olvanil; tinyatoxin; a compound as described in U.S. Patent Publication No. 2006/0240097; a compound as described in U.S. Patent Publication No. 2009/0203774; a pentadienamide derivative as described in U.S. Patent Publication No. 2009/0203667; a compound as described in U.S. Patent Publication No. 2009/0170942; and the like.

Exemplary synthetic regulators include compounds of the following structures:

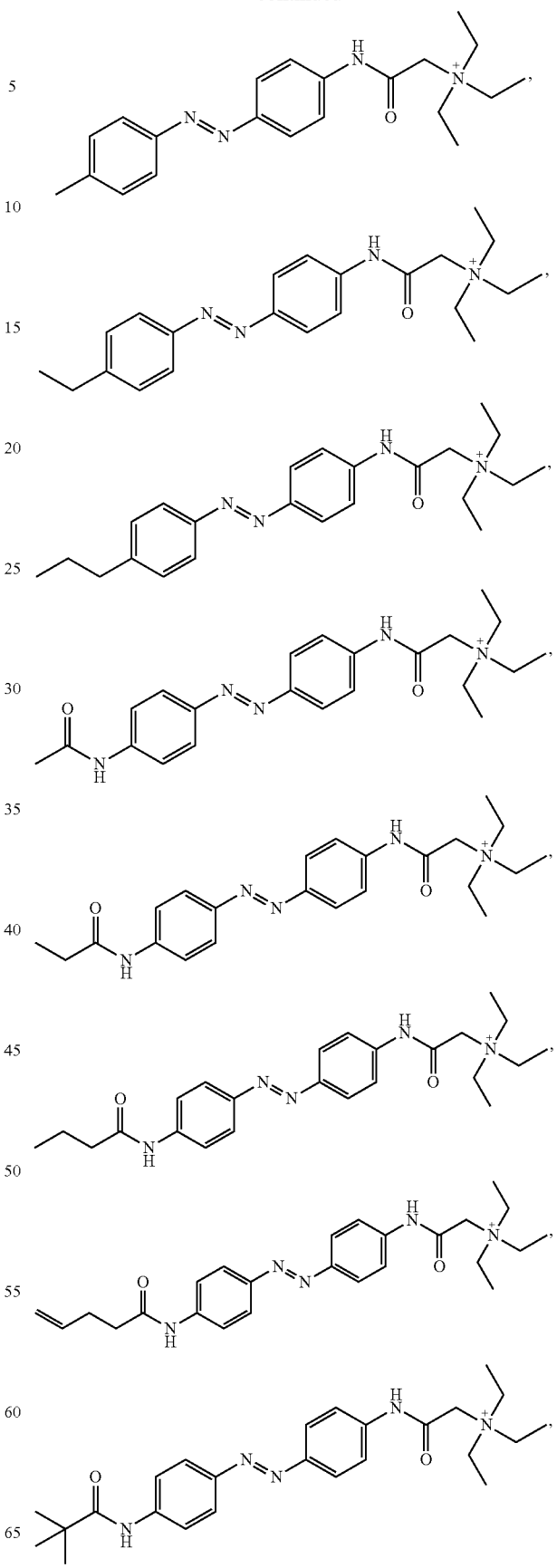

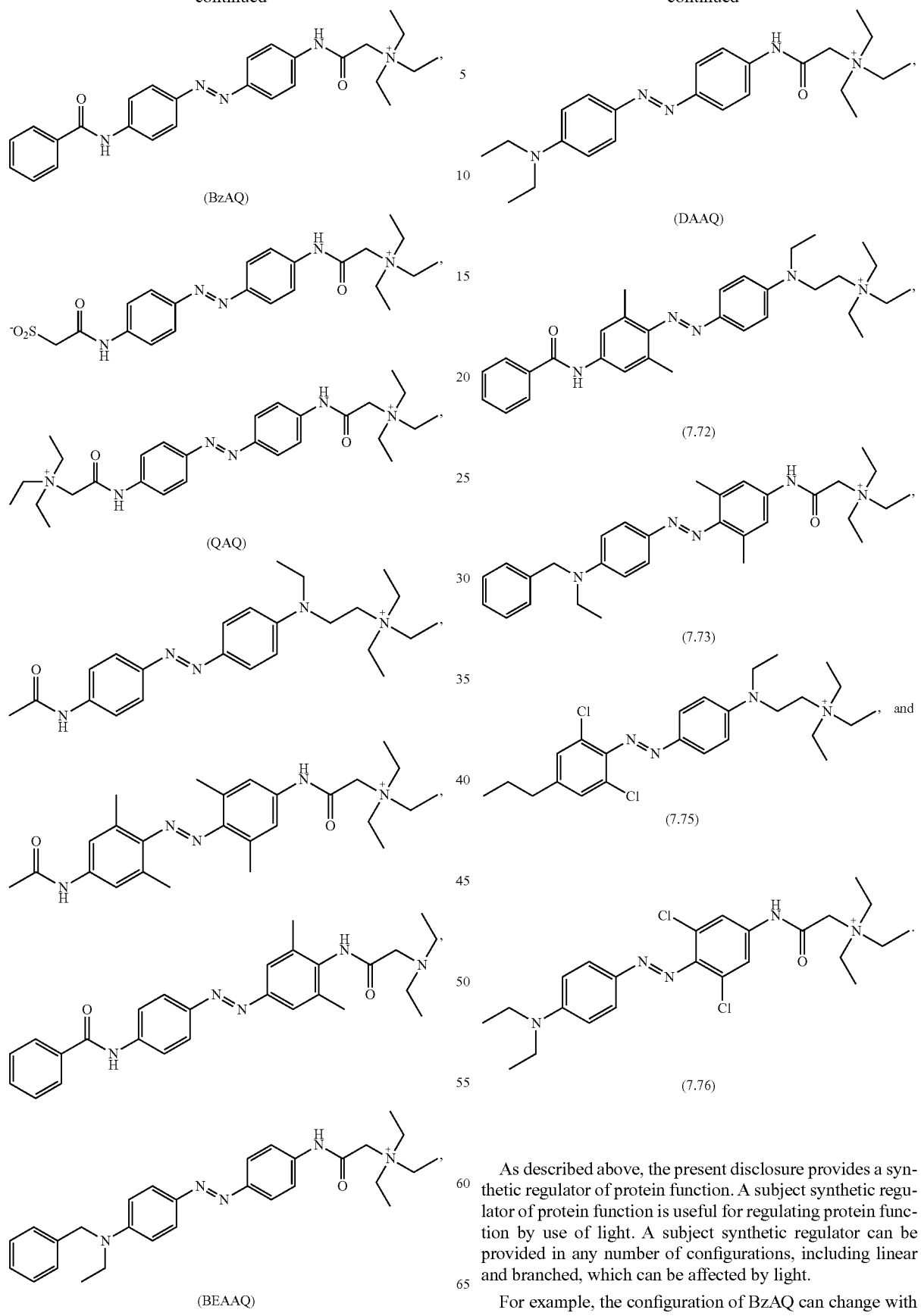

As described above, the present disclosure provides a synthetic regulator of protein function. A subject synthetic regulator of protein function is useful for regulating protein function by use of light. A subject synthetic regulator can be provided in any number of configurations, including linear and branched, which can be affected by light.

For example, the configuration of BzAQ can change with application of certain wavelengths of light.

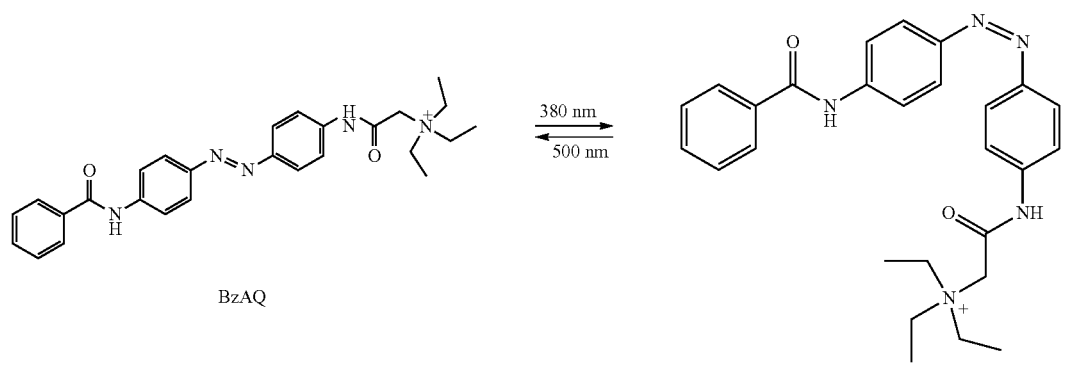

BzAQ

Other characteristics of BzAQ include being a trans-blocker, an external blocker, and selective for $K_v$ channels.

In another example, the configuration of BEAAQ can change with application of certain wavelengths of light.

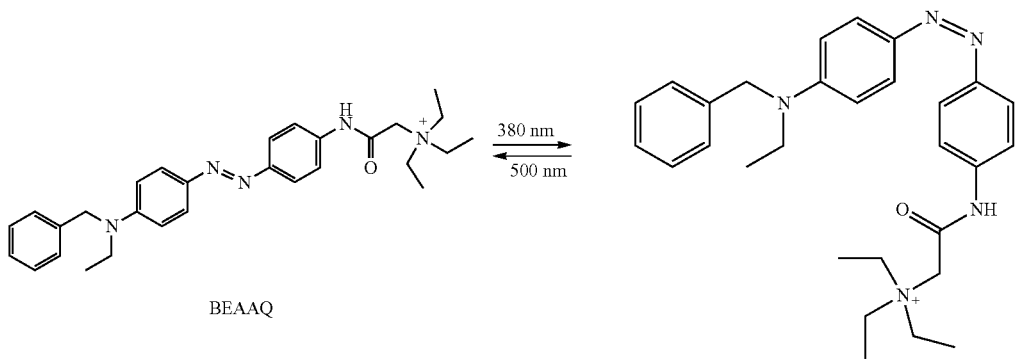

BEAAQ

Other characteristics of BEAAQ include being a cis-blocker and being able to block $K_v$ channels.

In another example, the configuration of DAAQ can change with application of certain wavelengths of light.

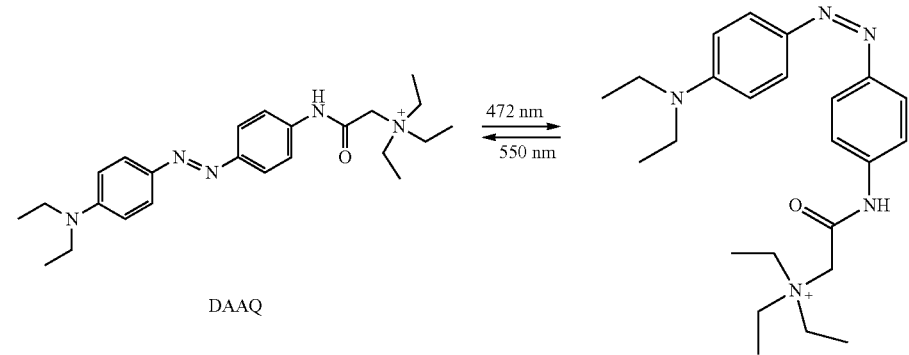

DAAQ

Other characteristics of DAAQ include being a trans-blocker, an external blocker, a red-shifted compound, and being able to block $K_v$ channels.

In another example, the configuration of QAQ can change with application of certain wavelengths of light.

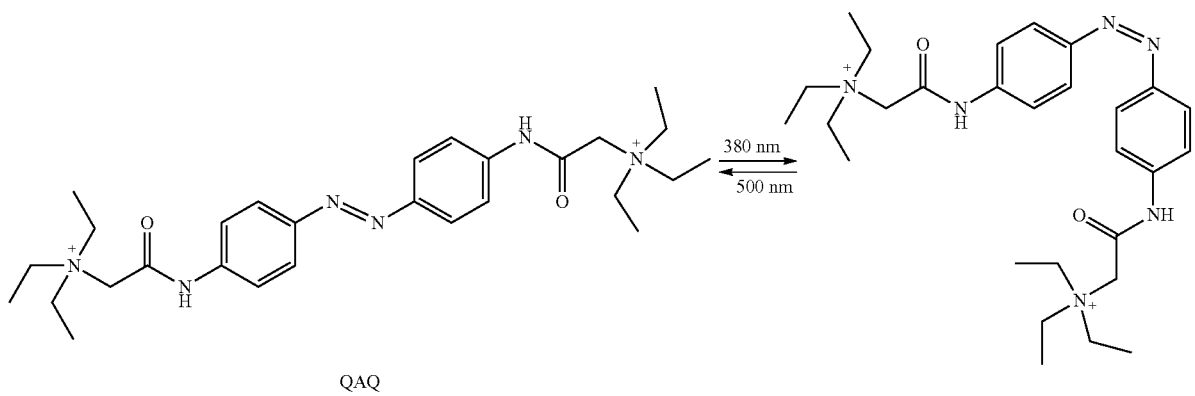

QAQ

Other characteristics of QAQ include being a trans-blocker, an internal blocker, and being able to block $K_v$, $Na_v$, and $Ca_v$ channels.

Compositions

The embodiments further provide compositions comprising a subject synthetic regulator. Compositions comprising a subject synthetic regulator can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-morpholino)ethanesulfonic acid (MES), 2-(N-morpholino)ethanesulfonic acid sodium salt (MES), 3-(N-Morpholino)propanesulfonic acid (MOPS), N-tris[hydroxymethyl]methyl-3-aminopropanesulfonic acid (TAPS), etc.; a solubilizing agent; a detergent, e.g., a non-ionic detergent such as Tween-20, Nonidet-P40, etc.: a protease inhibitor; and the like.

Pharmaceutical Compositions

The embodiments provide pharmaceutical compositions comprising a subject synthetic regulator. In some embodiments, the pharmaceutical composition is suitable for administering to an individual in need thereof.

A pharmaceutical composition comprising a subject synthetic regulator may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A pharmaceutical composition comprising a subject synthetic regulator can optionally include a pharmaceutically acceptable carrier(s) that facilitate processing of an active ingredient into pharmaceutically acceptable compositions. As used herein, the term "pharmacologically acceptable carrier" refers to any carrier that has substantially no long-term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, $7^{th}$ ed. 1999); "Remington: The Science and Practice of Pharmacy" (Alfonso R. Gennaro ed., Lippincott, Williams & Wilkins, $20^{th}$ 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, $4^{th}$ edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A subject synthetic regulator can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods (described below), a subject synthetic regulator may be administered to the host using any convenient means capable of resulting in the desired reduction in disease condition or symptom. Thus, a subject synthetic regulator can be incorporated into a variety of formulations for therapeutic administration. More particularly, a subject synthetic regulator can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

A subject synthetic regulator can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject synthetic regulator can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

A subject synthetic regulator can be utilized in aerosol formulation to be administered via inhalation. A subject synthetic regulator can be formulated into pressurized acceptable propellants such as dichlorodifluoromethane, propane, nitrogen and the like.

Furthermore, a subject synthetic regulator can be made into suppositories by mixing with a variety of bases such as emulsifying bases or water-soluble bases. A subject synthetic regulator can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise a subject synthetic regulator in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject synthetic regulator calculated in an amount sufficient to produce the desired effect in association with a pharmaceutically acceptable diluent, carrier or vehicle. The specifications for a subject synthetic regulator depend on the particular compound employed and the effect to be achieved, and the pharmacodynamics associated with each compound in the host.

A subject synthetic regulator can be administered as injectables. Injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a subject synthetic regulator is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Light-Regulated Polypeptides

The present disclosure further provides a light-regulated polypeptide, where a subject light-regulated polypeptide comprises a polypeptide and a subject synthetic regulator of receptor function in non-covalent association with the polypeptide. The synthetic regulator of polypeptide function can be non-covalently associated with the polypeptide at or near a ligand binding site of the polypeptide. In some embodiments, a subject light-regulated polypeptide is isolated, e.g., free of other polypeptides or other macromolecules. In other embodiments, a subject light-regulated polypeptide is membrane-associated and is present in vitro. In other embodiments, a subject light-regulated polypeptide is present in a living cell in vitro or in vivo. In other embodiments, a subject light-regulated polypeptide is present in a membrane of a living cell in vitro or in vivo. In other embodiments, a subject light-regulated polypeptide is present in a living cell in a tissue in vitro or in vivo. In other embodiments, a subject light-regulated polypeptide is present in a living cell in a multicellular organism. Polypeptides with which a subject synthetic regulator can be non-covalently associated include, e.g., receptors, ion channels, enzymes, and the like.

A change in the wavelength and/or intensity of light (Δλ) to which the light-regulated polypeptide is exposed results in a change in ligand binding to a ligand-binding site of the light-regulated polypeptide, e.g., results in a change in binding of the ligand portion of the synthetic polypeptide to the ligand-binding site of the light-regulated polypeptide. A "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. Repetitive changing from $\lambda_1$ to $\lambda_2$, then from $\lambda_2$ to $\lambda_1$, and back, e.g., switching from a first wavelength to a second wavelength, and back again repeatedly, is also contemplated. Repetitive changing from light to darkness, from darkness to light, etc., is also contemplated.

In some embodiments, the change in wavelength (from $\lambda_1$ to $\lambda_2$; from light to darkness; or from darkness to light) results in a change in binding of the ligand to a ligand-binding site. As used herein, a "change in binding of a ligand to a ligand-binding site" includes increased binding and decreased binding. As used herein, "increased binding" includes one or more of: an increased probability of binding of the ligand to the ligand-binding site; an increased binding affinity of the ligand for the ligand-binding site; an increased local concentration of the ligand at the ligand-binding site; and an increased occupancy of the ligand in the ligand-binding site. As used herein, "decreased binding" includes one or more of: a decreased probability of binding of the ligand to the ligand-binding site; a decreased binding affinity of the ligand for the ligand-binding site; a decreased local concentration of the ligand at the ligand-binding site; and a decreased occupancy of the ligand in the ligand-binding site. As used herein, the term "change in wavelength" to which a synthetic regulator is exposed, or to which a receptor/synthetic light regulator complex is exposed, refers to a change in wavelength from $\lambda_1$ to $\lambda_2$; a change from light to darkness; or a change from darkness to light. An increase in binding includes an increase of from about 10% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some embodiments, the ligand has a first probability of binding to the ligand site at a first wavelength of light; the ligand has a second probability of binding to the ligand binding site at a second wavelength of light; and the second probability is lower than the first probability. In other embodiments, the ligand has a first probability of binding to the ligand site at a first wavelength of light; the ligand has a second probability of binding to the ligand binding site at a second wavelength of light; and the second probability is higher than the first probability. In other embodiments, ligand has a first probability of binding to the ligand site when exposed to light; the ligand has a second probability of binding to the ligand binding site in the absence of light (e.g., in darkness); and the second probability is lower than the first probability. In other embodiments, the ligand has a first probability of binding to the ligand site when exposed to light; the ligand has a second probability of binding to the ligand binding site in the absence of light and the second probability is higher than the first probability.

The local concentration of the ligand portion of the synthetic regulator at the ligand binding site in a subject light-regulated polypeptide is high. For example, the local concentration of the ligand portion of the synthetic regulator at the ligand binding site in a subject light-regulated polypeptide ranges from about 500 nM to about 50 mM, e.g., from about 500 nM to about 750 nM, from about 750 nM to about 1 mM, from about 1 mM to about 5 mM, from about 5 mM to about 10 mM, from about 10 mM to about 20 mM, from about 20 mM to about 30 mM, or from about 30 mM to about 50 mM.

Change in Wavelength Resulting in Binding of the Ligand to the Ligand-Binding Site or Higher Affinity Ligand Binding to Ligand-Binding Site In some embodiments, a change in the wavelength of light to which the light-regulated polypeptide is exposed results in an increase in binding affinity of the ligand portion of a subject synthetic regulator for a ligand-binding site of the polypeptide portion of the light-regulated polypeptide. For example, in some embodiments, a change in wavelength of light to which the light-regulated polypeptide is exposed results in an at least about 10%, at least about 20%, at least about 30%, at least about 50%, at least about 75%, at least about 2-fold, at least about 5-fold, at least about 10-fold, at least about 25-fold, at least about 50-fold, at least about 100-fold, at least about 250-fold, at least about 500-fold, at least about $10^3$-fold, at least about $5\times10^3$-fold, at least about $10^4$-fold, at least about $5\times10^4$-fold, or greater, increase in binding affinity.

Where the ligand is an agonist, the change in wavelength will in some embodiments result in activation of the light-regulated polypeptide. Where the ligand is an agonist, the change in wavelength will in some embodiments result in desensitization of the light-regulated polypeptide. Conversely, where the ligand is an antagonist, the change in wavelength results in a block of activation of the light-regulated polypeptide, e.g., block of the ability to activate the light-regulated polypeptide with free agonist. Where the ligand is a blocker (e.g., a pore blocker of an ion channel, or an interaction domain that binds to other biological macromolecules such as polypeptides or nucleic acids), the change in wavelength results in block of polypeptide activity.

Expressed another way, where the ligand is an agonist, and where a change in the wavelength of light to which the light-regulated polypeptide is exposed results in a higher binding affinity of the ligand moiety of the synthetic regulator to the ligand-binding site of the light-regulated polypeptide, the change in wavelength results in transition from an inactive state to an active state, or to a desensitized state. Where the ligand is an antagonist, the change in wavelength results in transition from a responsive state to an unresponsive state. Where the ligand is a blocker, the change in wavelength results in transition from an active state to an inactive state.

Change in Wavelength Resulting in Removal of Ligand from Ligand-Binding Site, or Reduced Binding Affinity In some embodiments, a change in the wavelength of light to which the light-regulated polypeptide is exposed results in removal of the ligand portion of a subject synthetic regulator from a ligand-binding site of the light-regulated polypeptide, e.g., the ligand is not bound to the ligand-binding site. In some embodiments, a change in the wavelength of light to which the light-regulated polypeptide is exposed results in reduced binding affinity of the ligand portion of a subject synthetic regulator for a ligand-binding site of the light-regulated polypeptide, e.g., the ligand has reduced binding affinity for the ligand-binding site. For example, in some embodiments, a change in the wavelength of light to which the light-regulated polypeptide is exposed results in a reduction of binding affinity of at least about 10%, at least about 20%, at least about 25%, at least about 30%, at least about 40%, at least about 50%, at least about 60%, at least about 70%, at least about 80%, at least about 90%, at least about 95%, or more.

Where the ligand is an agonist, the change in wavelength will in some embodiments result in deactivation of the light-regulated polypeptide. Where the ligand is an agonist, the change in wavelength will in some embodiments result in recovery from desensitization of the light-regulated polypeptide. Conversely, where the ligand is an antagonist, the change in wavelength results in activation of the light-regulated polypeptide, or results in removal of a blocker from the light-regulated polypeptide. Where the ligand is a blocker (e.g., a pore blocker of an ion channel, or an interaction domain that binds to other biological macromolecules such as polypeptides or nucleic acids), the change in wavelength results in relief of a block in polypeptide activity and permits the receptor to function normally.

Expressed another way, where the ligand is an agonist, and where a change in the wavelength of light to which the light-regulated polypeptide is exposed results in removal (or non-binding) of the ligand moiety of the synthetic regulator from the ligand-binding site of the light-regulated polypeptide, the change in wavelength results in transition from an active state to an inactive state, or from a desensitized state to a responsive state. Where the ligand is an antagonist, the change in wavelength results in transition from an unresponsive state to a responsive state. Where the ligand is a blocker, the change in wavelength results in transition from an inactive state to an active state.

Ion Channels

In some embodiments, the polypeptide portion of a subject light-regulated polypeptide is an ion channel. A subject light-regulated ion channel comprises an ion channel and a subject synthetic regulator of receptor function in non-covalent association with the ion channel. The synthetic regulator of polypeptide function is non-covalently associated with the ion channel at or near a ligand binding site of the receptor on the ion channel. In some embodiments, the synthetic regulator can provide occlusion to the ion channel. Ion channels with which a subject synthetic regulator of polypeptide function can be non-covalently associated include, e.g., sodium channels, potassium channels, calcium channels, and chloride channels. The ion channel can be voltage regulated, cAMP regulated, or ligand gated.

Sodium Channels

A variety of different isoforms of mammalian voltage dependent sodium channels have been identified, and are summarized below in Table 1. These channels can be classified into three main groups (for review see Goldin, Annals N.Y. Academy of Sciences 868:38-50, 1999).

TABLE 1

Sodium Channel Sub-type Summary

| Channel Name & Gene Symbol | Sub-type/ Alternate Names | Tissue Distribution | Accession Number |
|---|---|---|---|
| SCN1A (Nav1.1) | | | |
| | Rat I (rat) | CNS/PNS | X03638 |
| | HBSCI (human) | CNS | X65362 |
| | GPB1 (guinea pig) | CNS | AF003372 |
| SCN2A (Nav1.2) | | | |
| | Rat (rat) | CNS | X03639 |
| | HBSCH (human) | CNS | X65361 |
| | HBA (human) | CNS | M94055 |
| Nav1.2A | Rat IIA | CNS | X61149 |
| SCN3A(Nav1.3) | | | |
| | Rat III (rat) | CNS | Y00766 |
| SCN4A (Nav1.4) | | | |
| | SkM1, μ1 (rat) | Skeletal muscle | M26643 |
| | SkM1, (human) | Skeletal muscle | N81758 |
| SCN5A (Nav1.5) | | | |
| | SkM2 (rat) | Skeletal muscle/ | M27902 |
| | RH1 (rat) | Heart | |
| | H1 (human) | heart | M77235 |
| SCN8A (Nav1.6) | | | |
| | NaCh6 (rat) | CNS/PNS | L39018 |
| | PN4a (rat) | CNS/PNS | AF049239A |
| | Scn8a (mouse) | CNS | U26707 |
| | ScnSa (human) | CNS | AF050736 |
| | CerIII (guinea pig) | CNS | AF003373 |
| SCN9A (Nav1.7) | | | |
| | PN1 (rat) | PNS | U79568 |
| | HNE-Na (human) | Thyroid | X82835 |
| | Nas (rabbit) | Schwann cells | U35238 |
| SCN9A (Nav1.7) | | | |
| | SNS (rat) | PNS | X92184 |
| | PN3 (rat) | PNS | U53833 |
| | SNS (mouse) | PNS | Y09108 |
| SCN6A Nav2.1 | | | |
| SCN7A Nav2.2 | Na2.1 (human) | Heart, uterus, muscle | M91556 |
| | Na-G (rat) | Astrocytes | M96578 |
| | SCL11 (rat) | PNS | Y09165 |
| nav2.3 Nav3.1 SCN1b Nβ1.1 | Na2.3 (mouse) | Heart, uterus, muscle | L36179 |
| | β1 (rat) | CNS | M91808 |
| | β1 (human) | CNS | L10338 |
| SCH2b Nβ2.1 | | | |
| | β2 (rat) | CNS | U37026 |
| | β2 (human) | CNS | AF007783 |

Potassium Channels

Voltage-dependent potassium channels repolarize nerve and muscle cells after action potential depolarization. They also play important regulatory roles in neural, muscular, secretory, and excretory systems.

A summary of the numerous potassium sub-types is presented in Table 2 below.

TABLE 2

Potassium Channel Sub-type Summary

| Channel Name | Sub-type/ Alternate Names | Accession Number | Reference |
|---|---|---|---|
| ATP-regulated | | | |
| | rKir.1 (ROMK1) (rat) | U12541 | US Pat. No. 5,356,775 |
| | hKir1.1 (ROMK1) (human) | | US Pat. No. 5,882,873 |
| | Kir1.1 | U73191 | |
| | Kir1.3 | U73193 | |
| II. | Bcell | | US Pat. No. 5,744,594 |
| III. | hβIR | | US Pat. No. 5,917,027 |
| IV. | IIuK$_{ATP}$-1 | | EP0 768 379A1 |
| Constitutively active | | | |
| | Kir2.1 (IRK1) | U12507 | US Pat. No. 5,492,825 US Pat. No. 5,670,335 |
| | Kir2.2 | X78461 | |
| | Kir2.3 | X78461 | |
| G-protein regulated | | | |
| | Kir3.1 (GIK1, KGA) | U0171 | US Pat. No. 5,728,535 |
| | Kir3.2 | U11859 | US Pat. No. 5,734,021 |
| | Kir3.3 | U11869 | US Pat. No. 5,744,324 |
| | Kir3.4 (CIR) | X83584 | US Pat. No. 5,747,278 |
| | Kir4.1(BIR10) | X83585 | |
| | Kir5.1(BIR9) | X83581 | |
| | Kir6.1 | D42145 | |
| | Kir6.2 | D5081 | |
| | Kir7.1 | | EP0 922 763A1 |
| Voltage regulated | | | |
| KCNA1 | hKv1.1 (RCK1, RBK1, MBK1, MK1, HuK1) | LO2750 | |
| KCNA2 | hKv1.2 (RBK2, RBK5, NGK1, IIuKIV) | | |
| KCNA3 | Kv1.3 (KV3, RGK5, HuKiIII, HPCN3) | | |
| KCNA4 | Kv1.4 (RCK4, RHK1, HuKII) | | |
| KCNA5 | Kv1.5 (KV1, HPCN1, HK2) | | |
| KCNA6 | Kv1.6 (KV2, RCK2, IIBK2) | | |
| KCNA7 | Kv1.7 (MK6, RK6, HaK6) | | US Pat. No. 5,559,009 |
| Kv2 (Shab) | | | |
| KCNB1 | Kv2.1 (DRK1, mShab) | M64228 | |
| KCNB2 | Kv2.2 (CDRK1) K channel 2 | | US Pat. No. 5,710,019 |
| Kv3 (Shaw) | | | |
| KCNB1 | Kv3.1 (NGK2) | | |
| KCNB2 | Kv3.2 (KshIIIA) | | |
| KCNB3 | Kv3.3 (KshIIID) | X607796 | |
| KCNB4 | Kv3.4 (Raw3) | | |
| Kv4 (Sh1) | | | |
| KCND1 | Kv4.1 (mShal, KShIVA) | M64226 | |
| KCND2 | Kv4.2 (RK5, Rat Shal1) | | |
| KCND3 | Kv4.3 (KShIVB) hKv5.1 (IK8) Kv6.1 (K13) Kv7 Kv8.1 Kv9 | | WO 99/41372 |
| Delayed Rectifier | | | |
| | KvLQT1 | AF000571 | US Pat. No. 5,599,673 |
| | HERG (crg) | U04270 | WO 99/20760 |
| Calcium regulated Calcium regulated Big | | | |
| | BKCa(hSLO) HBKb3 (β subunit) Maxi-K | U11717 | WO 99/42575 US Pat. No. 5,776,734 US Pat. No. 5,637,470 |
| Calcium regulated Calcium regulated Small | | | |
| KCNN1 | SKCa1 | U69883 | |
| KCNN2 | SKCa2 | U69882 | |
| KCNN3 | SKCa3 | U69884 | |
| KCNN4 | SKCa4 (IKCa1) | | Muscle Nerve 1999 22(6) 742-50 |
| | TWIK1 | U33632 | |

Calcium Channels

Calcium channels are generally found in many cells where, among other functions, they play important roles in signal transduction. In excitable cells, intracellular calcium supplies a maintained inward current for long depolarizing responses and serves as the link between depolarization and other intracellular signal transduction mechanisms. Like voltage-gated sodium channels, voltage-gated calcium channels have multiple resting, activated, and inactivated states.

Multiple types of calcium channels have been identified in mammalian cells from various tissues, including skeletal muscle, cardiac muscle, lung, smooth muscle and brain, [see, e.g., Bean, B. P. (1989) Ann. Rev. Physiol. 51:367-384 and Hess, P. (1990) Ann. Rev. Neurosci. 56:337]. The different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed (Swandulla, D. et al., Trends in Neuroscience 14:46, 1991).

Chloride Channels

Chloride channels are found in the plasma membranes of virtually every cell in the body. Chloride channels mediate a variety of cellular functions including regulation of transmembrane potentials and absorption and secretion of ions across epithelial membranes. When present in intracellular membranes of the Golgi apparatus and endocytic vesicles, chloride channels also regulate organelle pH. For a review, see Greger, R. (1988) Annu. Rev. Physiol. 50:111-122.

Three distinct classes of chloride channels are apparent based on their type of regulation and structural conformation, Table 3. The first class includes the GABA and Glycine receptor super families, the second class includes the CFTR (Cystic fibrosis Transmembrane Conductance Regulator) and the third class includes the voltage regulated chloride channels.

TABLE 3

Chloride Channel Sub-type Summary

| Channel Type | Sub-type | Tissue Distribution | Reference |
|---|---|---|---|
| Ligand gated | GABA$_A$ Receptor family | CNS & PNS | Synapse 21, 189-274 (1995) |
| | Glycine Receptor family | CNS & PNS | Trends Neurosci. 14 458-461 (1991) |
| cAMP regulated | CRTR | Epithelial cells | Science 245, 1066-1073 (1989) |
| Voltage regulated | ClC-1 | Skeletal muscle | Nature 354, 301-304 (1991) |
| | ClC-1 | Ubiquitous | Nature 356, 57-60 (1992) |
| | ClC-Ka | Kidney | J. Biol. Chem. 268, 3821-3824 (1993) |
| | ClC-Kb | Kidney | PNAS 91, 6943-6947 (1994) |
| | ClC-3 | Broad, e.g. kidney & brain | Neuron 12, 597-604 (1994) |
| | ClC-4 | Broad, e.g. kidney & brain | Hum. Nol. Genet. 3, 547-552 (1994) |
| | ClC-5 | Mainly kidney | J. Biol. Chem. 270, 31172-31177 91995) |
| | ClC-6 | Ubiquitous | FEBS Lett. 377, 15-20 (1995) |
| | ClC-7 | Ubiquitous | FEBS Lett. 377, 15-20 (1995) |

In some embodiments, the polypeptide portion of a subject light-regulated polypeptide is a glycine receptor.

In some embodiments, the polypeptide portion of a subject light-regulated polypeptide is an acetylcholine receptor. In some embodiments, the polypeptide portion of a subject light-regulated polypeptide is a nicotinic acetylcholine receptor. In some embodiments, the polypeptide portion of a subject light-regulated polypeptide is a muscarinic acetylcholine receptor. In some embodiments, the polypeptide portion of a subject light-regulated polypeptide is an M1, M2, M3, M4, or M5 muscarinic acetylcholine receptor subtype.

Cells

The embodiments further provide a cell comprising a subject light-regulated polypeptide. A subject cell finds use in a variety of applications, e.g., screening applications, such as identification of agents that modulate the activity of a receptor; and research applications such as examination of a physiological event. Where the cell is used in a screening assay, the cell can be referred to as a "test cell."

In some embodiments, the cell is a eukaryotic cell in in vitro cell culture, and is grown as an adherent monolayer, or in suspension. In other embodiments, the cell is a eukaryotic cell and is part of a tissue or organ, either in vivo or in vitro. In other embodiments, the cell is a eukaryotic cell and is part of a living multicellular organism, e.g., a protozoan, an amphibian, a reptile, a plant, an avian organism, a mammal, a fungus, an algae, a yeast, a marine microorganism, a marine invertebrate, an arthropod, an isopod, an insect, an arachnid, etc. In other embodiments, the cell is a prokaryotic cell.

In other embodiments, the cell is a member of archaea, e.g., an archaebacterium. Archaebacteria include a methanogen, an extreme halophile, an extreme thermophile, and the like. Suitable archaebacteria include, but are not limited to, any member of the groups Crenarchaeota (e.g., *Sulfolobus solfataricus, Defulfurococcus mobilis, Pyrodictium occultum, Thermofilum pendens, Thermoproteus tenax*), Euryarchacota (e.g., *Thermococcus celer, Methanococcus thermolithotrophicus, Methanococcus jannaschii, Methanobacterium thermoautotrophicum, Methanobacterium formicicum, Methanothennus fervidus, Archaeoglobus fulgidus, Thermoplasma acidophilum, Haloferax volcanni, Methanosarcina barkeri, Methanosaeta concilli. Methanospririllum hungatei, Methanomicrobium mobile*), and Korarchaeota.

In some embodiments, the cell is of a particular tissue or cell type. For example, where the organism is a plant, the cell is part of the xylem, the phloem, the cambium layer, leaves, roots, etc. Where the organism is an animal, the cell will in some embodiments be from a particular tissue (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

A subject cell is in many embodiments a unicellular organism, or is grown in culture as a single cell suspension, or as monolayer. In some embodiments, a subject cell is a eukaryotic cell. Suitable eukaryotic cells include, but are not limited to, yeast cells, insect cells, plant cells, fungal cells, mammalian cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineurn, Fusarium venenaturn, Neurospora crassa, Chlarnydomonas reinhardtii*, and the like.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Iluh-7 cells, BIIK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. In some embodiments, the neuronal cell is a primary cell isolated from an animal. In some embodiments, the neuronal cell or neuronal-liked cell is an immortalized cell line. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721). CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In other embodiments, the host cell is a plant cell. Plant cells include cells of monocotyledons ("monocots") and dicotyledons ("dicots"). Guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

Suitable prokaryotic cells include bacteria (e.g., Eubacteria) and archaebacteria. Suitable archaebacteria include a methanogen, an extreme halophile, an extreme thermophile, and the like. Suitable archaebacteria include, but are not limited to, any member of the groups Crenarchaeota (e.g., *Sulfolobus solfataricus, Defillfurococcus mobilis, Pyrodictium occultuin, Therinofilum pendens, Thermoproteus tenax*), Euryarchaeota (e.g., *Thermococcus celer, Methanococcus thermolithotrophicus, Methanococcus jannaschii, Methanobacterium thermoautotrophicum, Methanobacterium formicicum, Methanothennus fervidus, Archaeoglobus fidgidus, Thermoplasma acidophilum, Haloferax volcanni, Methanosarcina barkeri, Methanosaeta concilli, Methanospririllum hungatei, Methanotnicrobium mobile*), and Korarchaeota. Suitable eubacteria include, but are not limited to, any member of Hydrogenobacteria, Thermotogales, Green non-sulfphur bacteria, Denococcus Group, Cyanobacteria, Purple bacteria, Planctomyces, Spirochetes, Green Sulphur bacteria, Cytophagas, and Gram positive bacteria (e.g., *Mycobacterium* sp., *Micrococcus* sp., *Streptomyces* sp., *Lactobacillus* sp., *Helicobacterium* sp., *Clostridium* sp., *Mycoplasma* sp., *Bacillus* sp., etc.).

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of *Salmonella* strains which can be employed in the embodiments include, but are not limited to, *Salmonella typhi* and *S. typhimurium*. Suitable *Shigella* strains include, but are not limited to, *Shigella flexneri, Shigella sonnei*, and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas Rhodobacter sphaeroides, Rhodobacter capsulatus, Rhodospirillum rubrum, Rhodococcus* sp., and the like. In some embodiments, the cell is *Escherichia coli*.

Membranes

The embodiments further provide a membrane comprising a subject light-regulated polypeptide. In some embodiments, the membrane is a biological membrane (e.g., a lipid bilayer surrounding a biological compartment such as a cell, including artificial cells, or a membrane vesicle or sheet). In some embodiments, the membrane is part of a living cell, as described above. In other embodiments, the membrane is an artificial (synthetic) membrane, e.g., a planar membrane, a liposome, etc.

In some embodiments, the artificial membrane is a lipid bilayer. In other embodiments, the artificial membrane is a lipid monolayer. In some embodiments, the artificial membrane is part of a liposome. Liposomes include unilamellar vesicles composed of a single membrane or lipid bilayer, and multilamellar vesicles (MLVs) composed of many concentric membranes (or lipid bilayers).

Artificial membranes, and methods of making same, have been described in the art. See, e.g., U.S. Pat. No. 6,861,260; Kansy et al. (1998) *J. Med. Chem.* 41(7):1007-10; and Yang et al. (1996) *Advanced Drug Delivery Reviews* 23:229-256.

A subject artificial membrane will in some embodiments, include one or more phospholipids. In some embodiments, the artificial membrane comprises a mixture of phospholipids containing saturated or unsaturated mono or disubstituted fatty acids and a combination thereof. These phospholipids are in some embodiments selected from dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palm itoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, and palmiticlinoleoylphosphatidic acid. Suitable phospholipids also include the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in such lysophosphatidyl derivatives will in some embodiments be palimtoyl, oleoyl, palmitoleoyl, linoleoyl myristoyl or myristoleoyl.

Methods of Modulating Protein Activity

The embodiments provide methods of modulating protein activity. In certain aspects, the embodiments provide methods of modulating activity of a subject light-regulated polypeptide, where the method generally involves changing the wavelength of light to which the light-regulated polypeptide is exposed. In certain aspects, the embodiments provide methods of modulating activity of a polypeptide, where the method generally involves: a) contacting the polypeptide with a subject synthetic regulator, where the synthetic regulator binds to the polypeptide, thereby generating a light-regulated polypeptide; and b) changing the wavelength of light to which the light-regulated polypeptide is exposed. In certain aspects, the present disclosure provides methods of modulating activity of a ligand-binding polypeptide, where the method generally involves: a) contacting the ligand-binding polypeptide with a subject synthetic regulator, thereby generating a light-regulated polypeptide; and b) changing the wavelength of light to which the light-regulated polypeptide is exposed. In other embodiments, as described below, in other aspects, the present disclosure provides methods of modulating activity of a non-light-regulated polypeptide whose activity is modulated by modulating the activity of a light-regulated polypeptide. In some aspects, the present disclosure provides methods of modulating the activity of a non light-regulated polypeptide in a cell. The methods generally involve modulating an activity of a light-regulated polypeptide in the cell, where modulation of the activity of the light-regulated polypeptide in the cell modulates the activity of the non-light-regulated polypeptide. Modulating the activity of the light-regulated polypeptide results in modulation of the non-light-regulated polypeptide.

As noted above, a "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to 2. In certain aspects, the embodiments provides methods of modulating activity of a native (wild-type) polypeptide, where the method generally involves: a) contacting a polypeptide with a subject synthetic regulator, where the subject synthetic regulator hinds to the polypeptide, forming a synthetic regulator/polypeptide complex; and h) changing the wavelength of light to which the synthetic regulator/polypeptide complex is exposed. As noted above, a "change in the wavelength of light to which the light-regulated polypeptide is exposed" includes: 1) a change from $\lambda_1$ to $\lambda_2$; 2) a change from $\lambda_2$ to $\lambda_1$; 3) a change from $\lambda_1$ to darkness (no light); and 4) a change from darkness to $\lambda_1$. The synthetic regulator/polypeptide complex is also referred to as a "light-regulated polypeptide."

In some embodiments, the receptor or the light-regulated polypeptide is present in a cell-free in vitro system, e.g, the receptor or the light-regulated polypeptide is not associated with a cell. In other embodiments, the receptor or the light-regulated polypeptide is associated with a cell, e.g., the receptor or the light-regulated polypeptide is integrated into a cell membrane in a cell, the receptor or the light-regulated polypeptide is in the cytosol of a cell, the receptor or the light-regulated polypeptide is in an intracellular organelle, etc. In other embodiments, the receptor or the light-regulated polypeptide is in a synthetic membrane, e.g., in a planar synthetic membrane, in a liposome, in a membrane of an artificial cell, etc. In some embodiments, the cell-associated polypeptide or the cell-associated light-regulated polypeptide is in a cell in vitro, e.g., in a cell in a monolayer, in a cell in suspension, in an in vitro tissue, etc. In other embodiments, the cell-associated polypeptide or the cell-associated light-regulated polypeptide is in a cell in vivo, e.g., in a cell of an organism, e.g., a living organism.

In some embodiments, the change in wavelength (from $\lambda_1$ to $\lambda_2$; from light to darkness; or from darkness to light) results in a change in binding of the ligand to a ligand-binding site. As used herein, a "change in binding of a ligand to a ligand-binding site" includes increased binding and decreased binding. As used herein, "increased binding" includes one or more of: an increased probability of binding of the ligand to the ligand-binding site; an increased binding affinity of the ligand for the ligand-binding site; an increased local concentration of the ligand at the ligand-binding site; and an increased occupancy of the ligand in the ligand-binding site. As used herein, "decreased binding" includes one or more of: a decreased probability of binding of the ligand to the ligand-binding site; a decreased binding affinity of the ligand for the ligand-binding site; a decreased local concentration of the ligand at the ligand-binding site; and a decreased occupancy of the ligand in the ligand-binding site. As used herein, the term "change in wavelength" to which a synthetic regulator is exposed, or to which a polypeptide/synthetic light regulator complex is exposed, refers to a change in wavelength from $\lambda_1$ to $\lambda_2$; a change from light to darkness; or a change from darkness to light. An increase in binding includes an increase of from about 10% to about 50%, from about 50% to about 2-fold, from about 2-fold to about 5-fold, from about 5-fold to about 10-fold, from about 10-fold to about 50-fold, from about 50-fold to about $10^2$-fold, from about $10^2$-fold to about $10^4$-fold, from about $10^4$-fold to about $10^6$-fold, from about $10^6$-fold to about $10^8$-fold, or a greater than $10^8$-fold increase in binding. A decrease in binding includes a decrease of from about 5% to about 10% to about 20% to about 30%, from about 30% to about 40%, from about 40% to about 50%, from about 50% to about 60%, from about 60% to about 70%, from about 70% to about 80%, from about 80% to about 90%, or from about 90% to 100% decrease in binding.

For example, in some embodiments, the ligand has a first probability of binding to the ligand site at a first wavelength of light; the ligand has a second probability of binding to the ligand binding site at a second wavelength of light; and the second probability is lower than the first probability. In other embodiments, the ligand has a first probability of binding to the ligand site at a first wavelength of light; the ligand has a second probability of binding to the ligand binding site at a second wavelength of light; and the second probability is higher than the first probability. In other embodiments, ligand has a first probability of binding to the ligand site when exposed to light; the ligand has a second probability of binding to the ligand binding site in the absence of light (e.g., in darkness); and the second probability is lower than the first probability. In other embodiments, the ligand has a first probability of binding to the ligand site when exposed to light; the ligand has a second probability of binding to the ligand binding site in the absence of light and the second probability is higher than the first probability.

A change in wavelength can result in a change in activity of the light-regulated protein. "Activity" will depend, in part, on the polypeptide, and can include activity of an ion channel; activity of a receptor in transmitting a signal; etc.

In some embodiments, the change in wavelength results in binding of the ligand to the ligand-binding site of the polypeptide. In some embodiments, the change in wavelength results in increased binding affinity of the ligand to the ligand-binding site for the polypeptide. In these embodiments, where the ligand is an agonist, and the change results in activation of the polypeptide; and where the ligand is an antagonist, the change results in block of activation of the polypeptide; and where the ligand is an active site or pore blocker, the change results in inhibition of the polypeptide; and where the ligand is a blocker of a site of interaction with other macromolecules, the change interferes with that interaction. In some embodiments, prolonged binding of an agonist to the ligand-binding site results in desensitization or inactivation of the polypeptide. In other embodiments, binding of an antagonist blocks activation of the receptor.

In other embodiments, the change in wavelength results in lack of binding of the ligand to the ligand-binding site, e.g., removal of the ligand from the ligand-binding site of the polypeptide. In other embodiments, the change in wavelength results in reduced binding affinity of the ligand for the ligand-binding site, e.g., reduced binding affinity of ligand for the ligand-binding site of the polypeptide. In these embodiments, where the ligand is an antagonist, the change results in activation of said polypeptide; and where the ligand is an agonist, the change results in deactivation of light-regulated polypeptide, or recovery from desensitization or inactivation.

In some embodiments, the polypeptide/synthetic regulator complex is exposed to light of a first wavelength, where exposure to light of the first wavelength ($\lambda_1$) results in binding of the ligand to the ligand-binding site (or increased binding affinity of the ligand for the ligand-binding site); and the polypeptide/synthetic regulator complex is subsequently exposed to light of a second wavelength ($\lambda_2$), where exposure to light of the second wavelength results in removal of the ligand from the ligand-binding site (or reduced binding affinity of the ligand for the ligand-binding site). This change in wavelength from a first wavelength to a second wavelength ($\Delta\lambda$) can be repeated numerous times, such that the light is switched back and forth between $\lambda_1$ and $\lambda_2$. Switching between $\lambda_1$ and $\lambda_2$ results in switching or transition from a ligand-bound state to a ligand-unbound state.

In some embodiments, the polypeptide/synthetic regulator complex is exposed to light of a first wavelength, where exposure to light of the first wavelength ($\lambda_1$) results in binding of the ligand to the ligand-binding site (or increased binding affinity of the ligand for the ligand-binding site); and the light is subsequently turned off, e.g., the polypeptide/synthetic regulator complex is in darkness, where keeping the polypeptide/synthetic regulator complex in darkness results in removal of the ligand from the ligand-binding site (or reduced binding affinity of the ligand for the ligand-binding site). This change from $\lambda_1$ to darkness can be reversed, e.g., from darkness to $\lambda_1$; and repeated any number of times, as described above. In other embodiments, the polypeptide/synthetic regulator complex is exposed to light of a first wavelength, where exposure to light of the first wavelength ($\lambda_1$) results in lack of binding of the ligand to the ligand-binding site (or reduced binding affinity of the ligand for the ligand-binding site); and the light is subsequently turned off, e.g., the polypeptide/synthetic regulator complex is in darkness, where keeping the polypeptide/synthetic regulator complex in darkness results in binding of the ligand to the ligand-binding site (or increased binding affinity of the ligand for the ligand-binding site). This change from $\lambda_1$ to darkness can be reversed, e.g., from darkness to $\lambda_1$; and repeated any number of times, as described above.

As noted above, the change in wavelength can be repeated any number of times, e.g, from $\lambda_1$ to $\lambda_2$ and from $\lambda_2$ to $\lambda_1$; or from $\lambda_1$ to darkness and from darkness to $\lambda_1$. Thus, a subject method provides for inducing a transition or switch from a ligand-bound state of a protein to a ligand-unbound state of the protein, or from a high affinity state to a low affinity state. Depending on whether the ligand is an agonist or an antagonist, the light-regulated polypeptide will in some embodiments be switched from an active state to an inactive (or deactivated) state, or from an inactive (or deactivated) state to an active state.

The wavelength of light to which the light-regulated polypeptide is exposed ranges from $10^8$ m to about 1 in, e.g., from about $10^{-8}$ m to about $10^{-7}$ m, from about $10^{-7}$ in to about $10^{-6}$ m, from about $10^{-6}$ m to about $10^{-4}$ m, from about $10^{-4}$ m to about $10^{-2}$ m, or from about $10^{-2}$ m to about 1 m. "Light," as used herein, refers to electromagnetic radiation, including, but not limited to, ultraviolet light, visible light, infrared, and microwave.

The wavelength of light to which the light-regulated polypeptide is exposed ranges in some embodiments from about 200 nm to about 800 nm, e.g., from about 200 nm to about 250 nm, from about 250 nm to about 300 nm, from about 300 nm to about 350 nm, from about 350 nm to about 400 mil, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, or from about 750 nm to about 800 nm, or greater than 800 nm.

In other embodiments, the wavelength of light to which the light-regulated polypeptide is exposed ranges from about 800 nm to about 2500 nm, e.g., from about 800 nm to about 900 nm, from about 900 nm to about 1000 nm, from about 1000 nm to about 1200 nm, from about 1200 nm to about 1400 nm, from about 1400 nm to about 1600 nm, from about 1600 nm to about 1800 nm, from about 1800 nm to about 2000 nm, from about 2000 nm to about 2250 nm, or from about 2250 nm to about 2500 nm. In other embodiments, the wavelength of light to which the light-regulated polypeptide is exposed ranges from about 2 nm to about 200 nm, e.g., from about 2 nm to about 5 nm, from about 5 nm to about 10 nm, from about 10 nm to about 25 nm, from about 25 nm to about 50 nm, from about 50 nm to about 75 nm, from about 100 nm, from about 100 nm to about 150 nm, or from about 150 nm to about 200 nm.

The difference between the first wavelength and the second wavelength can range from about 10 nm to about 800 nm or more, e.g., from about 10 nm to about 25 nm, from about 25 nm to about 50 nm, from about 50 nm to about 100 nm, from about 100 nm to about 200 nm, from about 200 nm to about 250 nm, from about 250 nm to about 500 nm, or from about 500 nm to about 800 nm. Of course, where the light-regulated polypeptide is switched from darkness to light, the difference in wavelength is from essentially zero to a second wavelength.

The intensity of the light can vary from about 1 W/m$^2$ to about 50 W/m$^2$, e.g., from about 1 W/m$^2$ to about 5 W/m$^2$, from about 5 W/m$^2$ to about 10 W/m$^2$, from about 10 W/m$^2$, from about 10 W/m$^2$ to about 15 W/m$^2$, from about 15 W/m$^2$ to about 20 W/m$^2$, from about 20 W/m$^2$ to about 30 W/m$^2$, from about 30 W/m$^2$ to about 40 W/m$^2$, or from about 40 W/m$^2$ to about 50 W/m$^2$. The intensity of the light can vary from about 1 µW/cm$^2$ to about 100 µW/cm$^2$, e.g., from about 1 µW/cm$^2$ to about 5 µW/cm$^2$, from about 5 µW/cm$^2$ to about 10 µW/cm$^2$, from about 10 µW/cm$^2$ to about 20 µW/cm$^2$, from about 20 µW/cm$^2$ to about 25 µW/cm$^2$, from about 25 µW/cm$^2$ to about 50 µW/cm$^2$, from about 50 µW/cm$^2$ to about 75 µW/cm$^2$, or from about 75 µW/cm$^2$ to about 100 µW/cm$^2$. In some embodiments, the intensity of light varies from about 1 µW/mm$^2$ to about 1 W/mm$^2$, e.g., from about 1 µW/mm$^2$ to about 50 µW/mm$^2$, from about 50 µW/mm$^2$ to about 100 µW/mm$^2$, from about 100 µW/mm$^2$ to about 500 µW/mm$^2$, from about 500 µW/mm$^2$ to about 1 mW/mm$^2$, from about 1 mW/mm$^2$ to about 250 mW/mm$^2$, from about 250 mW/mm$^2$ to about 500 mW/mm$^2$, or from about 500 mW/mm$^2$ to about 1 W/mm$^2$.

In some embodiments, the light-regulated polypeptide is regulated using sound, instead of electromagnetic (EM) radiation (light). For example, in some embodiments, the light-regulated polypeptide is regulated using ultrasound to effect a change from a first isomeric form to a second isomeric form.

The duration of exposure of the light-regulated polypeptide to light can vary from about 1 µsecond (µs) to about 60 seconds (s) or more, e.g., from about 1 µs to about 5 µs, from about 5 µs to about 10 µs, from about 10 µs to about 25 µs, from about 25 µs to about 50 µs, from about 50 µs to about 100 µs, from about 100 µs to about 250 µs, from about 250 µs to about 500 µs, from about 500 µs to about 1 millisecond (ms), from about 1 ms to about 10 ms, from about 10 ms to about 50 ms, from about 50 ms to about 100 ms, from about 100 ms to about 500 ms, from about 500 ms to about 1 second, from about 1 second to about 5 seconds, from about 5 seconds to about 10 seconds, from about 10 seconds to about 15 seconds, from about 15 seconds to about 30 seconds, from about 30 seconds to about 45 seconds, or from about 45 seconds to about 60 seconds, or more than 60 seconds. In some embodiments, the duration of exposure of the light-regulated polypeptide to light varies from about 60 seconds to about 10 hours, e.g., from about 60 seconds to about 15 minutes, from about 15 minutes to about 30 minutes, from about 30 minutes to about 60 minutes, from about 60 minutes to about 1 hour, from about 1 hour to about 4 hours, from about 4 hours to about 6 hours, from about 6 hours to about 8 hours, or from about 8 hours to about 10 hours, or longer.

The duration of binding of the ligand portion of the synthetic regulator to the ligand-binding site can vary from less than one second to days. For example, in some embodiments, the duration of binding of the ligand portion of the synthetic regulator to the ligand-binding site varies from about 0.5 second to about 1 second, from about 1 second to about 5 seconds, from about 5 seconds to about 15 seconds, from about 15 seconds to about 30 seconds, from about 30 seconds to about 60 seconds, from about 1 minute to about 5 minutes, from about 5 minutes to about 15 minutes, from about 15 minutes to about 30 minutes, or from about 30 minutes to about 60 minutes. In other embodiments, the duration of binding of the ligand portion of the synthetic regulator to the ligand-binding site varies from about 60 minutes to about 2 hours, from about 2 hours to about 4 hours, from about 4 hours to about 8 hours, from about 8 hours to about 12 hours, from about 12 hours to about 18 hours, from about 18 hours to about 24 hours, from about 24 hours to about 36 hours, from about 36 hours to about 48 hours, from about 48 hours to about 60 hours, from about 60 hours to about 72 hours, from about 3 days to about 4 days, from about 4 days to about 5 days, or from about 5 days to about 7 days, or longer.

Figure 8:
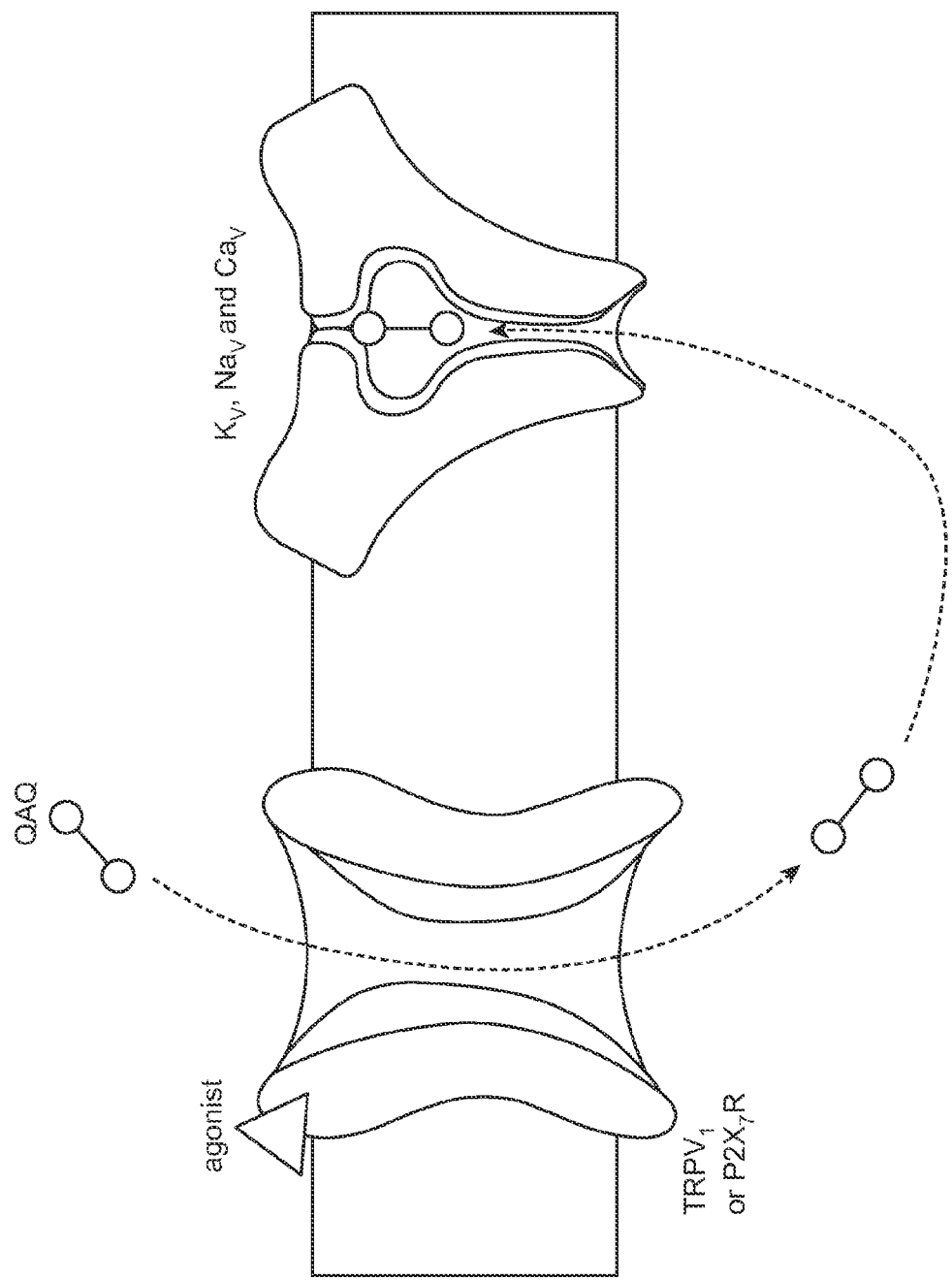
FIG. 8 schematically depicts use of an agonist of a ligand-gated non-selective cation channel to load membrane-impermeant QAQ into cells.

As noted above, in some embodiments, a synthetic regulator is membrane impermeant. In these embodiments, a physical, electrical, or chemical stimulus can be applied to a cell to facilitate entry of the synthetic regulator into the cell. An example of this is depicted schematically in FIG. 8. In some embodiments, a subject method of modulating protein activity involves contacting a cell comprising a polypeptide, whose activity is to be modulated, with a subject membrane-impermeant synthetic regulator and further applying a physical, chemical, or electrical stimulus to the cell, to facilitate entry of the membrane-impermeant synthetic regulator into the cell. For example, a subject method can involve contacting a cell comprising a polypeptide, whose activity is to be modulated, with a subject membrane-impermeant synthetic regulator and an agonist of a nonselective ion channel, where the agonist facilitates entry of the membrane-impermeant synthetic regulator into the cell via the nonselective ion channel. Nonselective ion channels include, e.g., ligand-gated nonselective cation channels. Nonselective cation channels include, e.g., $TRPV_1$, $P2X_7R$, and the like. $P2X_7R$ (or P2X purinoceptor 7) is described in, e.g., Chessell et al. (2005) *Pain* 114:386; and Rassendren et al. (1997) *J. Biol. Chem.* 272:5482. $P2X_7R$ can be activated by adenosine triphosphate (ATP), or an ATP analog. An example of a membrane-impermeant synthetic regulator is QAQ.

$TRPV_1$ (transient receptor potential cation channel, subfamily V, member 1; also known as vanilloid receptor type 1), is a ligand-gated nonselective cation channel that is activated by a variety of endogenous and exogenous physical and chemical stimuli, including, e.g., heat over 43° C., low pH, the endocannabinoid anandamide, N-arachidonoyl-dopamine, and capsaicin. For $TRPV_1$, see, e.g., Cui et al. (2006) *J. Neurosci.* 26:9385.

$TRPV_1$ agonists include, e.g., capsaicin; a capsaicinoid (where capsaicinoids include, e.g., capsiate (4-hydroxy-3-methoxybenzyl (E)-8-methyl-6-nonenoate); dihydrocapsiate (4-hydroxy-3-methoxybenzyl 8-methylnonanoate); nordihydrocapsiate (4-hydroxy-3-methoxybenzyl 7-methyl-octanoate); capsiate derivatives such as vanillyl decanoate, vanillyl nonanoate, vanillyl octanoate and the like; fatty acid esters of vanillyl alcohol; and various straight chain or branched chain fatty acids which have a fatty acid chain length similar to that of nordihydrocapsiate); resinifcratoxin; olvanil; tinyatoxin; a compound as described in U.S. Patent Publication No. 2006/0240097; a compound as described in U.S. Patent Publication No. 2009/0203774; a pentadienamide derivative as described in U.S. Patent Publication No. 2009/0203667; a compound as described in U.S. Patent Publication No. 2009/0170942; and the like.

Modulating Activity of a Second, Non-Light-Regulated Polypeptide

In some embodiments, modulating the activity of a light-regulated polypeptide results in modulating the activity of a polypeptide other than the light-regulated polypeptide. Thus, in other aspects, the present disclosure provides methods of modulating activity of a polypeptide whose activity is modulated by modulating the activity of a light-regulated polypeptide. In some aspects, the present disclosure provides methods of modulating the activity of a non light-regulated polypeptide in a cell. The methods generally involve modulating an activity of a light-regulated polypeptide in the cell, where modulation of the activity of the light-regulated polypeptide in the cell modulates the activity of the non-light-regulated polypeptide.

A non-light-regulated polypeptide whose activity is modulated by modulating the activity of a light-regulated polypeptide includes a polypeptide whose activity is modulated by a change in voltage of a biological membrane, a polypeptide whose activity is modulated by depolarization of a biological membrane; a polypeptide whose activity is modulated by a change in intracellular concentration of an ion (e.g., a monovalent or divalent ion, e.g., a monovalent or divalent cation); a polypeptide whose activity is modulated by phosphorylation; and the like. As one non-limiting example, a light-regulated polypeptide comprises a glutamate receptor (ligand-gated ion channel) as the ligand-binding polypeptide, where the light-regulated polypeptide is in the plasma membrane of a cell. Light activation of the light-regulated glutamate receptor in the cell opens the channel, resulting in influx of ion and depolarization of the plasma membrane. Depolarization of the plasma membrane activates a voltage-gated ion channel, such as a calcium channel Activation of the calcium channels is readily detected by standard methods, e.g., use of an indicator dye, etc.).

As another non-limiting example, the light-regulated polypeptide comprises a GPCR as the ligand-binding polypeptide. Activation of the light-regulated GPCR activates an ion channel or an enzyme. Activation of the ion channel or enzyme is readily detected using standard methods, e.g., use of an indicator dye for the permeating ion, or a colorimetric, fluorimetric, or luminescence assay for the product of the enzyme. As another non-limiting example, the light-regulated polypeptide comprises a receptor tyrosine kinase (RTK); and activation of the light-regulated RTK results in phosphorylation of a downstream protein, e.g., a transcription factor. Activation of the transcription factor is readily detected by, e.g., detecting a transcript. As another non-limiting example, the light-regulated polypeptide comprises an opioid receptor. Modulation of the opioid receptor by exposure to light (or removal of light) can modulate a potassium ion channel; and modulation of a potassium ion channel is readily detected using standard methods, e.g., use of a dye for potassium ions.

As another non-limiting example, the non-light-regulated polypeptide is a voltage-dependent ion channel, and the light-regulated polypeptide is an ion channel (e.g., a ligand-gated ion channel); modulation of the light-regulated ion channel by changing the wavelength of light to which the light-regulated ion channel is exposed leads to a change in the membrane potential of a cell harboring both the non-light-regulated, voltage-dependent ion channel and the light-regulated ion channel. A change in the membrane potential of the cell modulates the activity of the non-light-regulated ion channel. Voltage-dependent ("voltage-gated") ion channels include voltage-gated sodium channels, voltage-gated potassium channels, and voltage-gated calcium channels. Whether the activity of the non-light-regulated, voltage-dependent ion channel is modulated can be readily determined using any of a number of assays designed to measure the intracellular concentration of an ion (e.g., potassium, sodium, calcium), where such assays include use of dyes.

Utility

A subject synthetic regulator, a subject light-regulated polypeptide, a subject cell, and a subject method of modulating receptor function, are useful in a wide variety of research applications, pharmaceutical applications, screening assays, therapeutic applications, and the like.

Research Applications

In some embodiments, a subject synthetic regulator or a subject light-regulated polypeptide is useful in studies of cell function, in studies of physiology of whole organisms, and the like.

In physiological studies, changing light exposure of a tissue, organ, or whole organism (or a part of a whole organism) that includes a subject light-regulated protein provides a method of regulating a function in the tissue, organ, or whole organism. For example, where the light-regulated polypeptide is a light-regulated ligand-gated ion channel, and the synthetic regulator comprises the ligand for the ligand-gated ion channel, changing the wavelength of light to which the light-regulated polypeptide is exposed will result in opening or closing of the ion channel, thereby altering ion concentration in cells in a manner that alters their activity (e.g., hormone or neurotransmitter secretion) or state (e.g., transcriptional or translational or metabolic state) or electrical firing, etc.

Screening Methods

The embodiments provide methods of identifying an agent that modulates a function (e.g., an activity) of a polypeptide. The methods generally involve contacting a light-regulated polypeptide with a test agent; and determining the effect, if any, of the test agent on the activity of the light-regulated polypeptide (or on the activity of a polypeptide that is regulated by the light-regulated polypeptide). The effect, if any, of the test agent on the activity of the light-regulated polypeptide is determined by exposing the light-regulated polypeptide to light of a first wavelength. In the absence of the test agent, exposure of the light-regulated polypeptide to light of a first wavelength induces a transition from a ligand-unbound state to a ligand-bound state. In the presence of a test agent that affects binding of the ligand to the ligand-binding site, the transition from the ligand-unbound state to a ligand-bound state is inhibited.

In some embodiments, the light-regulated polypeptide is in vitro in solution (e.g., free of cells or membranes); and the assay is carried out in vitro. In other embodiments, the light-regulated polypeptide is in a membrane (e.g., a synthetic membrane) in the absence of a living cell (e.g., in a cell-free system); and the assay is carried out in vitro. In other embodiments, the light-regulated polypeptide is in a cell, e.g., a living cell in vitro or in vivo; and in some embodiments, the assay is carried out in vitro, and in other embodiments, the assay is carried out in vivo.

In some embodiments, the light-regulated polypeptide is in a cell (e.g., is integrated into the plasma membrane, is in the cytosol of the cell, is in a subcellular organelle, is in the nucleus of the cell, or is integrated into a membrane of a subcellular organelle). In these embodiments, the cell comprising the light-regulated polypeptide is a "test cell." The methods generally involve contacting the test cell with a test agent; and determining the effect, if any, of the test agent on the activity of the light-regulated polypeptide.

In some aspects, the present disclosure provides methods for identifying an agent that modulates a function (e.g., an activity) of a non-light-regulated polypeptide in the same solution, membrane, or cell, where the activity of the non-light-regulated polypeptide is modulated by modulating the activity of a light-regulated polypeptide. The methods generally involve contacting a non-light-regulated polypeptide and a light-regulated polypeptide (where the light-regulated polypeptide is in a solution, membrane, or cell) with a test agent; and determining the effect, if any, of the test agent on the activity of the non-light-regulated polypeptide (where the non-light regulated polypeptide is in the same solution, membrane, or cell as the light-regulated polypeptide), where the activity of the non-light-regulated polypeptide is modulated by changing the wavelength of light to which the cell is exposed. Whether the activity of the non-light regulated polypeptide is modulated is determined using an assay appropriate to the activity of the non-light-regulated polypeptide. For example, where the non-light-regulated polypeptide is a calcium channel, a calcium-sensitive dye, such as a Fura-2 dye, will in some embodiments be used to detect an effect of the test agent on the activity of the calcium channel. For example, where the non-light-regulated polypeptide is a sodium channel, a sodium-sensitive dye such as sodium-binding benzofuran isophthalate (SBFI) will in some embodiments be used to detect an effect of the test agent on the activity of the sodium channel. Such an assay can be used, e.g., to identify agents that modulate the activity of a voltage-dependent ion channel where, e.g., the non-light regulated polypeptide is a voltage-dependent ion channel, and the light-regulated polypeptide is a ligand-gated ion channel.

In some embodiments, the test agent is one that inhibits induction of a transition from a first, ligand-bound state to a second, ligand-unbound state. For example, in some embodiments, a test agent of interest is one that inhibits induction of a transition from a first, ligand-unbound state to a second, ligand-bound state by at least about 5%, at least about 10%, at least about 15%, at least about 20%, at least about 25%, at least about 30%, at least about 40%, at least about 50%, at least about 60%, at least about 70%, or at least about 80%, or more, compared to the induction in the absence of the test agent.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the embodiments include controls, where suitable controls include a sample (e.g., a sample comprising a subject polypeptide (a subject light-regulated polypeptide, e.g., a polypeptide in a complex with a subject synthetic regulator) in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, e.g., between 4° C. and 40° C. Incubation periods are selected for optimum activity, but may also be optimized to facilitate rapid high-throughput screening. Typically between 0.1 hour and 1 hour will be sufficient.

The screening methods may be designed a number of different ways, where a variety of assay configurations and protocols may be employed, as are known in the art. The above components of the method may be combined at substantially the same time or at different times. In some embodiments, a subject method will include one or more washing steps.

In some embodiments, the light regulated polypeptide is assayed in a membrane-free, cell free assay. In other embodiments, the light regulated polypeptide is integrated into an artificial membrane. In other embodiments, light regulated polypeptide is integrated into a biological membrane. In other embodiments, the light regulated polypeptide is in a living cell, e.g., in the cytosol, in the nucleus, in an intracellular organelle, in the plasma membrane, or in an intracellular membrane of the cell.

Biological cells which are suitable for use in a subject screening assay include, but are not limited to, primary cultures of mammalian cells, transgenic (non-human) organisms and mammalian tissue. Cells in screening assays may be dissociated either immediately or after primary culture. Cell types include, but are not limited to white blood cells (e.g. leukocytes), hepatocytes, pancreatic beta-cells, neurons, smooth muscle cells, intestinal epithelial cells, cardiac myocytes, glial cells, and the like.

Biological cells which are suitable for use in a subject screening assay include cultured cell lines (e.g., immortalized cell lines). Representative suitable cultured cell lines derived from humans and other mammals include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651). RAT1 cells, mouse L cells (ATCC No. CCLI.3), human embryonic kidney (HEK) cells (ATCC No. CRL1573), HLHepG2 cells, and the like.

In some embodiments, the cell is a neuronal cell or a neuronal-like cell. The cells can be of human, non-human primate, mouse, or rat origin, or derived from a mammal other than a human, non-human primate, rat, or mouse. Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

In some embodiments, the readout for an effect on the activity of the light regulated polypeptide is a direct measure of the activity of the light regulated polypeptide. A direct effect on the light regulated polypeptide is detected using an assay appropriate to the particular polypeptide. For example, where the light regulated receptor is an ion channel, the effect, if any, of the test agent on the activity of the ion channel is in some embodiments detected by detecting a change in the intracellular concentration of an ion. A change in the intracellular concentration of an ion can be detected using an indicator appropriate to the ion whose influx is controlled by the channel. For example, where the ion channel is a potassium ion channel, a potassium-detecting dye is used; where the ion channel is a calcium ion channel, a calcium-detecting dye is used; etc.

Suitable voltage-sensitive dyes include, but are not limited to, merocyanine-oxazolone dyes (e.g., NK2367); merocyanine-rhodanine dyes (e.g., NK2495, NK2761, NK2776, NK3224, and NK3225); oxonol dyes (e.g., RH155, RH479, RH482, RH1691, RH1692, and RH1838); styryl dyes (e.g., RH237, RH414, RH421, RH437, RH461, RH795, JPW1063, JPW3028, di-4-ANEPPS, di-9-ANEPPS, di-2-ANEPEQ, di-12-ANEPEQ, di-8-ANEPPQ, and di-12-ANEPPQ); and the like.

Suitable intracellular $K^+$ ion-detecting dyes include, but are not limited to, $K^+$-binding benzofuran isophthalate and the like.

Suitable intracellular $Ca^{2+}$ ion-detecting dyes include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C18, Calcium Green-C18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo-5F, Fluo-4FF, Mag-Fluo-4, Aequorin, dextran conjugates or any other derivatives of any of these dyes, and others (see, e.g., the catalog or Internet site for Molecular Probes, Eugene, see, also, Nuccitelli, ed., *Methods in Cell Biology, Volume* 40: *A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999); *Calcium Signaling Protocols* (Methods in Molecular Biology), 2005, D. G. Lamber, ed., Humana Press.).

In particular embodiments of interest, a subject screening method is useful for identifying agents that alter the sense of taste. In other embodiments, a subject screening method is useful for identifying agents that affect one or more neurological functions of a mammalian subject. In other embodiments, a subject screening method is useful for identifying agents that are selective for a particular receptor type or subtype, where the screening method involves determining the effect of the agent on a first subtype and a second subtype, where an effect on the first subtype, and a reduced effect (or substantially no effect) on the second subtype indicates selectivity of the test agent for the first subtype. In other embodiments, as noted above, a subject screening method is useful for identifying agents that modulate the activity of a voltage-gated ion channel.

Therapeutic Applications

A subject synthetic regulator of protein function is suitable for use in a variety of therapeutic applications, which are also provided. In some embodiments, a subject synthetic regulator of protein function is useful in restoring light sensitivity to a retina that has reduced light sensitivity. In other embodiments, a subject synthetic regulator of protein function is useful as a local anesthetic. In other embodiments, a subject synthetic regulator is useful as an anti-convulsant, e.g., in the treatment of epilepsy.

Restoring Light Sensitivity to a Retina

The embodiments provide a method for restoring light sensitivity to a retina, or conferring light sensitivity to a cell in the eye, the method generally involving administering to an individual in need thereof an effective amount of a subject synthetic regulator of protein function locally, e.g., in or around the eye.

A subject synthetic regulator that is suitable for this application comprises a ligand that confers light sensitivity on one or more cells in the eye, e.g., retinal pigment epithelial cells; and cells disposed in the neurosensory retina, for example, photoreceptor cells and Mueller cells. A pharmaceutical composition comprising a subject synthetic regulator is administered in or around the eye; the synthetic regulator attaches to a protein in a cell in the eye, and confers light sensitivity to the cell. Suitable pharmaceutical compositions are described in detail below. For example, the synthetic regulator can confer light sensitivity on a retinal ganglion.

A pharmaceutical composition comprising a subject synthetic regulator that confers light sensitivity on a cell can be delivered to the eye through a variety of routes. A subject pharmaceutical composition may be delivered intraocularly, by topical application to the eye or by intraocular injection into, for example the vitreous or subretinal (interphotoreceptor) space. Alternatively, a subject pharmaceutical composition may be delivered locally by insertion or injection into the tissue surrounding the eye. A subject pharmaceutical composition may be delivered systemically through an oral route or by subcutaneous, intravenous or intramuscular injection. Alternatively, a subject pharmaceutical composition may be delivered by means of a catheter or by means of an implant, wherein such an implant is made of a porous, non-porous or gelatinous material, including membranes such as silastic membranes or fibers, biodegradable polymers, or proteinaceous material. A subject pharmaceutical composition can be administered prior to the onset of the condition, to prevent its occurrence, for example, during surgery on the eye, or immediately after the onset of the pathological condition or during the occurrence of an acute or protracted condition.

The effects of therapy for an ocular disorder as described herein can be assessed in a variety of ways, using methods known in the art. For example, the subject's vision can be tested according to conventional methods. Such conventional methods include, but are not necessarily limited to, electroretinogram (ERG), focal ERG, tests for visual fields, tests for visual acuity, ocular coherence tomography (OCT), Fundus photography, Visual Evoked Potentials (VEP) and Pupillometry. In general, the embodiments provide for maintenance of a subject's vision (e.g., prevention or inhibition of vision loss of further vision loss due to photoreceptor degeneration), slowing progression of vision loss, or in some embodiments, providing for improved vision relative to the subject's vision prior to therapy.

Exemplary conditions of particular interest which are amenable to treatment according to the methods of the embodiments include, but are not necessarily limited to, diabetic retinopathy, age-related macular degeneration (AMD or ARMD) (wet form); dry AMD; retinopathy of prematurity; retinitis pigmentosa (RP); diabetic retinopathy; and glaucoma, including open-angle glaucoma (e.g., primary open-angle glaucoma), angle-closure glaucoma, and secondary glaucomas (e.g., pigmentary glaucoma, pseudoexfoliative glaucoma, and glaucomas resulting from trauma and inflammatory diseases).

Further exemplary conditions amenable to treatment according to the embodiments include, but are not necessarily limited to, retinal detachment, age-related or other maculopathies, photic retinopathies, surgery-induced retinopathies, toxic retinopathies, retinopathy of prematurity, retinopathies due to trauma or penetrating lesions of the eye, inherited retinal degenerations, surgery-induced retinopathies, toxic retinopathies, retinopathies due to trauma or penetrating lesions of the eye.

Specific exemplary inherited conditions of interest for treatment according to the embodiments include, but are not necessarily limited to, Bardet-Biedl syndrome (autosomal recessive); Congenital amaurosis (autosomal recessive); Cone or cone-rod dystrophy (autosomal dominant and X-linked forms); Congenital stationary night blindness (autosomal dominant, autosomal recessive and X-linked forms); Macular degeneration (autosomal dominant and autosomal recessive forms); Optic atrophy, autosomal dominant and X-linked forms); Retinitis pigmentosa (autosomal dominant, autosomal recessive and X-linked forms); Syndromic or systemic retinopathy (autosomal dominant, autosomal recessive and X-linked forms); and Usher syndrome (autosomal recessive).

Local Anesthetic

The embodiments provide a method of reducing or preventing pain in an individual, the method generally involving: a) administering to an individual in need thereof an effective amount of a subject synthetic regulator of protein function, where the synthetic regulator of protein function comprises a ligand that blocks a pain response or a pain signal, where the synthetic regulator binds to receptor or a channel, forming complex between the synthetic regulator and the receptor or channel; and b) exposing the receptor/regulator complex or channel/regulatory complex to a wavelength of light that provides for binding of the ligand to the receptor or channel. For example, in some embodiments, the protein is a cation channel, and the synthetic regulator binds to the cation channel, forming a cation channel/regulator complex, where the channel/regulator complex is exposed to a wavelength of light that provides for blocking of the channel, e.g., a $Na^+$ channel, an N-type $Ca^{2+}$ channel, etc.

An "effective amount" of a subject synthetic regulator is an amount that is effective to reduce pain by at least 30%, 40%, 60%, 70%, 80%, 90% or 100% for a period of time of from about 15 minutes to 5 days, e.g., from about 15 minutes to about 30 minutes, from about 30 minutes to about 60 minutes, from about 1 hour to about 4 hours, from about 4 hours to about 8 hours, from about 8 hours to about 16 hours, from about 16 hours to about 24 hours, from about 24 hours to about 36 hours, from about 36 hours to about 48 hours, from about 48 hours to about 3 days, or from about 3 days to about 5 days. The effectiveness of a subject synthetic regulator in treating nociceptive pain can be determined by observing one or more clinical symptoms or physiological indicators associated with nociceptive pain.

In these embodiments, a suitable synthetic regulator includes one that comprises, as a ligand, an opioid analgesic. Suitable ligands include, but are not limited to, morphine, oxycodone, fentanyl, pentazocine, hydromorphone, meperidine, methadone, levorphanol, oxymorphone, levallorphan, codeine, dihydrocodeine, hydrocodone, propoxyphene, nalmefene, nalorphine, naloxone, naltrexone, buprenorphine, butorphanol, nalbuphine, and pentazocine. In other embodiments, a suitable synthetic regulator comprises a ligand moiety selected from lidocaine, novocaine, xylocalne, lignocaine, novocaine, carbocaine, etidocaine, tetracaine, procaine, prontocaine, prilocalne, bupivacaine, cinchocaine, mcpivacaine, quinidine, flecainide, procaine, N-[[2'-(aminosulfonyl)biphenyl-4-yl]methyl]-N'-(2,2'-bithien-5-ylmethyl)succinamide (BPBTS), QX-314, saxitoxin, tetrodotoxin, and a type III conotoxin.

As noted above, in some embodiments, a subject synthetic regulator is membrane impermeant. Where a subject method involves administration of a membrane-impermeant synthetic regulator, a subject method can involve administering a subject membrane-impermeant synthetic regulator to an individual, and further applying a physical, chemical, or electrical stimulus to the individual, to facilitate entry of the membrane-impermeant synthetic regulator into a cell in the individual. For example, a subject method can involve administering a subject membrane-impermeant synthetic regulator and an agonist of a nonselective ion channel, where the agonist facilitates entry of the membrane-impermeant synthetic regulator into a cell via the nonselective ion channel. Nonselective ion channels include, e.g., ligand-gated nonselective cation channels. Suitable agonists of nonselective ion channels include those described hereinabove. For example, $TRPV_1$ agonists include, e.g., capsaicin; a capsaicinoid (where capsaicinoids include, e.g., capsiate (4-hydroxy-3-methoxybenzyl (E)-8-methyl-6-nonenoate); dihydrocapsiate (4-hydroxy-3-methoxybenzyl 8-methylnonanoate); nordihydrocapsiate (4-hydroxy-3-methoxybenzyl 7-methyl-octanoate); capsiate derivatives such as vanillyl decanoate, vanillyl nonanoate, vanillyl octanoate and the like; fatty acid esters of vanillyl alcohol; and various straight chain or branched chain fatty acids which have a fatty acid chain length similar to that of nordihydrocapsiate); resiniferatoxin; olvanil; tinyatoxin; a compound as described in U.S. Patent Publication No. 2006/0240097; a compound as described in U.S. Patent Publication No. 2009/0203774; a pentadienamide derivative as described in U.S. Patent Publication No. 2009/0203667; a compound as described in U.S. Patent Publication No. 2009/0170942; and the like. Suitable $P2X_7R$ agonists include ATP and ATP analogs that function as $P2X_7R$ agonists.

The present disclosure provides pharmaceutical compositions comprising a subject synthetic regulator. In some embodiments, a subject pharmaceutical composition is suitable for administering to an individual in need of a local anesthetic. Individuals in need of a local anesthetic include an individual who is about to undergo a surgical procedure, and an individual who has undergone a surgical procedure within the last 5 minutes to within the last 72 hours. Individuals in need of a local anesthetic further include individuals having a wound, e.g., a superficial wound.

A pharmaceutical composition comprising a subject synthetic regulator may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A pharmaceutical composition comprising a subject synthetic regulator can optionally include a pharmaceutically acceptable carrier(s) that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, 7th ed. 1999); "Remington: The Science and Practice of Pharmacy" (Alfonso R. Gennaro ed., Lippincott, Williams & Wilkins, 20th 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, 4th edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Routes of administration suitable for the methods of the embodiments include both systemic and local administration. In some embodiments, a subject pharmaceutical composition comprising a subject synthetic regulator is administered locally. As non-limiting examples, a pharmaceutical composition useful for treating nociceptive pain can be administered orally; by subcutaneous pump; by dermal patch; by intravenous, subcutaneous or intramuscular injection; by topical drops, creams, gels, sprays, or ointments; as an implanted or injected extended release formulation; as a bioerodable or non-bioerodable delivery system; by subcutaneous minipump or other implanted device; by intrathecal pump or injection; or by epidural injection. In some embodiments, a subject pharmaceutical composition comprising a subject synthetic regulator is administered sublingually. In some embodiments, a subject pharmaceutical composition comprising a subject synthetic regulator is administered topically to gum tissue. In some embodiments, a subject pharmaceutical composition comprising a subject synthetic regulator is injected into gum tissue. In some embodiments, a subject pharmaceutical composition comprising a subject synthetic regulator is administered topically to the skin. In some embodiments, a subject pharmaceutical composition comprising a subject synthetic regulator is administered at or near a site of a surgical incision. In some embodiments, a subject pharmaceutical composition comprising a subject synthetic regulator is administered intramuscularly at the site of a surgical incision. For example, in some embodiments, a subject pharmaceutical composition comprising a subject synthetic regulator is administered at a surgical site, and before the surgical wound is closed, the synthetic regulator/target protein complex is exposed to light of a wavelength that induces binding of the ligand to the protein. In some embodiments, a subject pharmaceutical composition is administered (e.g., injected) at or near a nerve. Thus, in some embodiments, a subject pharmaceutical composition is formulated for injection at or near a nerve. For example, for oral surgery, a subject pharmaceutical composition is injected at or near a nerve in gum tissue.

In some embodiments, a subject pharmaceutical composition comprising a subject synthetic regulator is administered just before surgery, e.g., from about 1 minute to about 2 hours before surgery, e.g., from about 1 minute to about 5 minutes, from about 5 minutes to about 15 minutes from about 15 minutes to about 30 minutes, from about 30

A subject synthetic regulator comprising a ligand that provides for pain prevention is suitable for preventing or reducing pain in an individual in need thereof. Individuals in need of treatment with a subject synthetic regulator comprising a ligand that provides for pain prevention include individuals who are about to undergo surgery, e.g., individuals who are scheduled to undergo a surgical procedure in the next 5 minutes to 72 hours; individuals who are undergoing a surgical procedure; and individuals who have undergone a surgical procedure within the previous 5 minutes to 1 hour. Thus, individuals suffering from post-operative pain are suitable for treatment. A subject synthetic regulator comprising a ligand that provides for pain prevention is also suitable for preventing or reducing pain in an individual having a wound, e.g., a superficial wound.

Anti-Convulsant Applications

In some embodiments, a subject synthetic regulator comprises, as a ligand, a ligand for a sodium channel, a potassium channel, or a GABA receptor, where the ligand functions as an anti-convulsant. In some embodiments, the synthetic regulator is administered in a pharmaceutical composition, as described supra and infra.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Photochromic, Internal Blockers of Voltage-Gated Potassium Channels

Materials and Methods

Cell Culture, Plasmids and Transfection.

HEK293 cells were grown in DMEM containing 5% FBS. For HEK293T cells, 500 mg/ml G-418 was also included. For electrophysiology studies, cells were plated at $12\times10^3$ cells/$cm^2$ on poly(L-lysine) coated coverslips and transfected the cells using the calcium phosphate method. K+ channel currents were recorded 24-48 h after transfection. Hippocampal neurons were prepared from neonatal rats according to standard procedures, plated at $50\times10^3$ cells/$cm^2$ on poly(L-lysine) coated coverslips, and grown in minimum essential medium containing 5% FBS, 20 mM glucose, B27 (Invitrogen), glutamine and Mito+ Serum Extender (BD Biosciences). Currents were recorded 14-25 days (d) after plating. Animal care and experimental protocols were approved by the University of California Berkeley Animal Care and Use Committee.

Electrophysiology Recordings from Cultured Cells.

Currents were recorded in the whole-cell patch clamp configuration using pipettes with 3-5 MSS resistance. To elicit voltage-gated $K^+$ currents from neurons and HEK293 cells, holding potential was set to −70 mV and stepped to +30 or +40 mV for 200, 250 or 300 ins. The bath solution for whole cell recordings contained in mM: 138 NaCl, 1.5 KCl, 1.2 $MgCl_2$, 2.5 $CaCl_2$, 5 HEPES, 10 glucose, pH 7.4 and during recordings from neurons, 20 bicuculline, 25 µM 6,7-dinitroquinoxaline-2,3-[1H,4H]-dione (DNQX) and 1 µM tetradotoxm (TTX). The intracellular solution contained in mM: 10 NaCl, 135 K-gluconate, 10 HEPES, 2 $MgCl_2$, 2 MgATP, EGTA, pH 7.4. The bath solution for inside-out patch recordings contained in mM: 160 KCl, 0.5 $MgCl_2$, 1 EGTA, 10 HEPES, pH 7.4. The pipette solution for inside-out patch recordings contained in mM: 150 NaCl, 10 KCl, 10 HEPES, 1 $MgCl_2$, 3 $CaCl_2$, pH 7.4. Solutions were adjusted to 300-310 mOsm.

AzoQA Treatment.

Cells were rinsed with whole cell bath solution and then incubated at 37° C. in the dark for 15 minutes at the indicated concentrations of AzoQA diluted from 200 mM DMSO stocks into bath solution and then rinsed with bath solution prior to recording. During some experiments, AAQ was locally perfused onto cells or patches at the indicated concentrations in either whole cell or inside-out patch solution after recording had begun.

Illumination Conditions.

To achieve photoswitching in living cells, a xenon lamp (175 W) with narrow band-pass filters (380BP10 and 500BP5) was used. Light output was measured using a handheld Newport meter (840-C model). At the back of the objective, light output was 0.3 $mW/cm^2$ for 380-nm light and 2.5 $mW/cm^2$ for 500-nm light. When measured through a 40× objective and normalized to the focal area at the specimen plane, light output was 0.5 $mW/mm^2$ and 3.5 $mW/mm^2$ for 380-nm and 500-nm light, respectively. For some experiments, we used a monochromator (Polychrome V; TILL Photonics) for illumination.

All data reported are averages±s.d.

Results

AAQ and EtAcAQ Effect

Figure 2A:
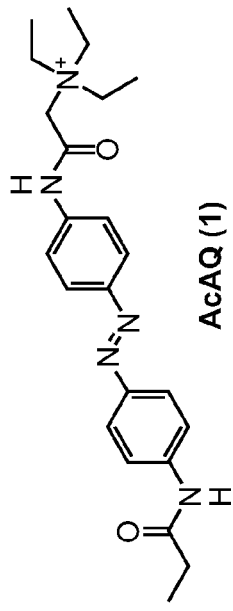
FIGS. 2A-C depict: (a) chemical structures of AAQ and EtAcAQ and (b, c) voltage-gated steady-state currents from Shaker IR channels after blocker treatment.

Acrylamide Azobenzene Quaternary ammonium (AAQ) 1, named for the acrylamide, azobenzene and quaternary ammonium components (FIG. 2a), can be a useful tool due to its persistent effects and lack of toxicity. If ligand-binding were to direct the covalent reaction of AAQ with surface residues near the external TEA-binding site of potassium channels, it can be possible to alter the rate of labeling by altering the TEA-binding site affinity with site-directed mutagenesis or by labeling with AAQ in the presence of a ligand that competes for the same site. Additionally, it can be possible to prevent covalent modification altogether by genetically removing the nucleophilic residue(s). These possibilities were tested using whole-cell recordings from HEK 293 cells expressing Shaker IR, which lacks fast inactivation but retains slow or P/C-type inactivation.

Figure 1B:
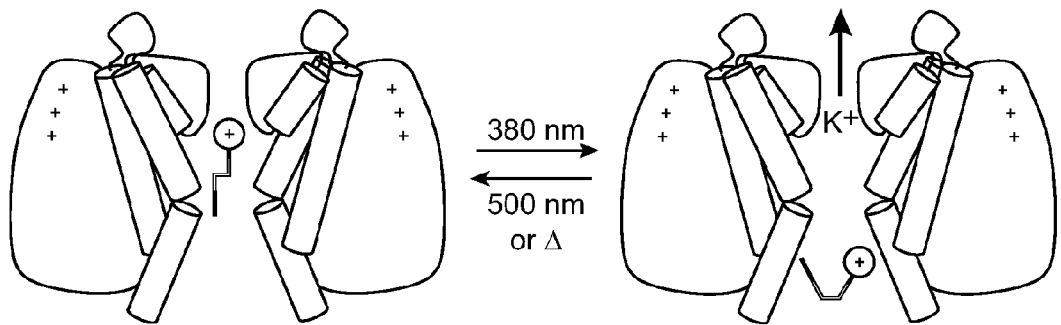
Figure 1C:
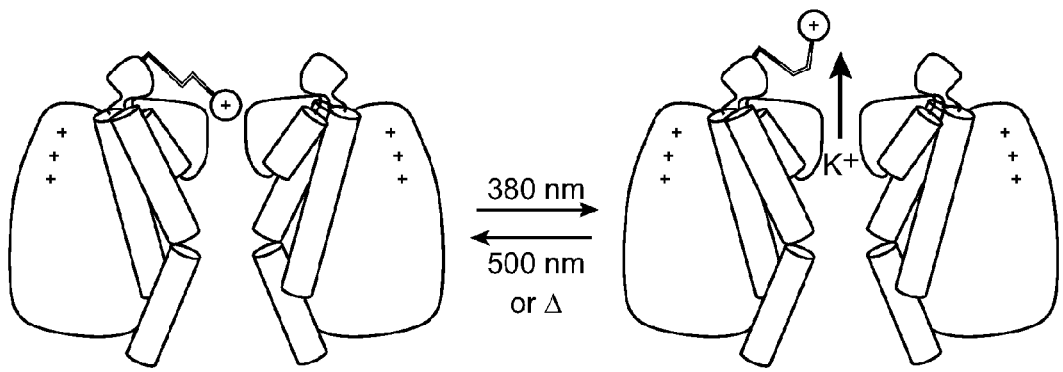

Three Shaker mutants with external TEA affinities spanning 3 orders of magnitude all appeared to react at similar rates with extracellularly applied AAQ and all three were substantially blocked and unblocked in 500-nm and 380-nm light respectively (FIG. 1a). FIG. 1b shows the PAL approach, designed to employ a photoswitchable pore blocker tethered to endogenous amino acids on the external channel surface. After affinity labeling the extended trans isomer presents the ammonium ion to block the pore while the cis isomer is too short to reach, allowing ion conduction. FIG. 1c shows photochromic blockers of the internal QA binding site. The elongated trans isomer can fit into the inner vestibule for the ammonium ion to block open channels while the bent cis isomer is not sterically accommodated and is unable to block.

Similarly, there was substantially no correlation between external TEA affinity and AAQ effectiveness observed in a screen of different mammalian $K^+$ channels that are present in neurons. Furthermore, inclusion of TEA at concentrations that result in about 80% pore occupancy did not produce significant changes in the apparent rate of labeling by AAQ.

Figure 2C:
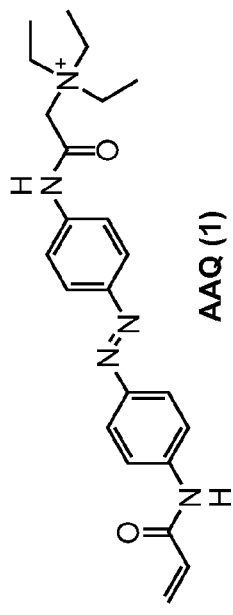
Figure 2C:
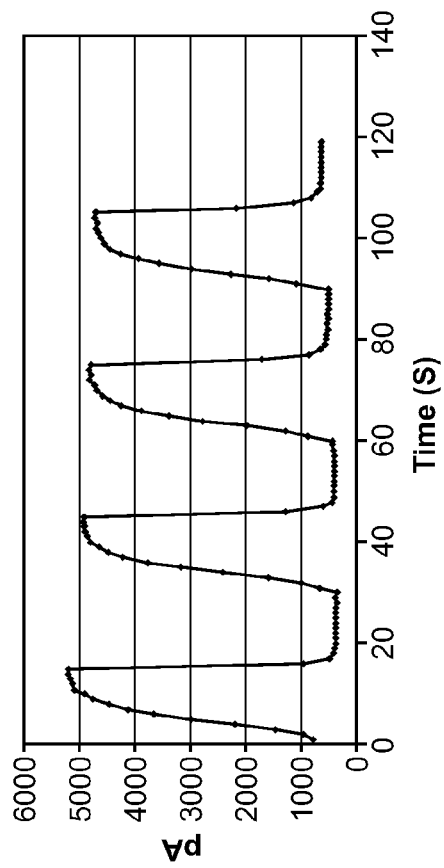
Figure 2B:
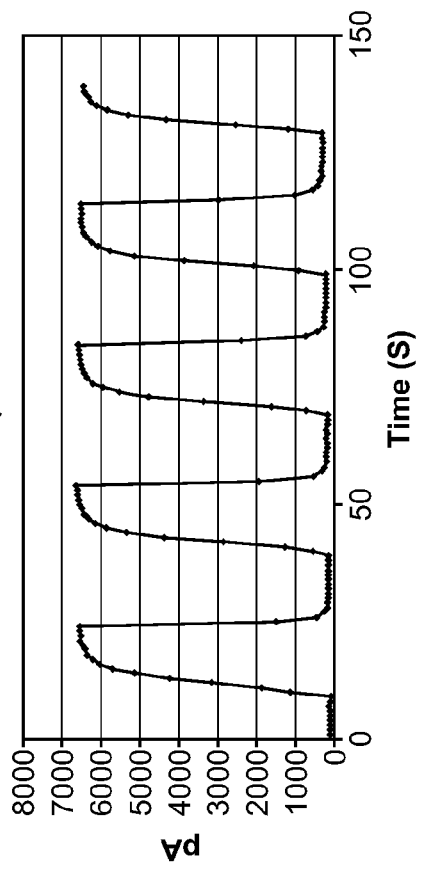

To determine whether the electrophile is a necessary component of AAQ, EtAcAQ was prepared (FIG. 2a), which is sterically similar to AAQ but lacks the electrophilic double bond. Under the same pre-treatment conditions, AcAQ produced considerable sustained photoswitching that is qualitatively indistinct from that obtained with AAQ (FIGS. 2b and 2c). FIGS. 2b and 2c show voltage-gated steady-state currents from Shaker IR channels after blocker treatment. Cells treated with either 400 uM AAQ (FIG. 2b) or 400 uM EtAcAQ (FIG. 2c) were exposed to 500-nm and 380-nm light as indicated. Voltage-gated K+ currents were elicited by pulsing from −70 to +40 mV for 200 ms at is intervals in whole cell voltage clamp.

Like AAQ, EtAcAQ persistently blocked the entire steady-state current in a light-dependent fashion. This result provides further evidence that AAQ does not substantially covalently attach to Shaker. Instead, it suggests that molecules of this type represent a new class of photochromic ligands that can stably associate with the channel or the surrounding environment to afford persistent block, effectively mimicking covalent modification.

AAQ Blocks the Internal TEA Binding Site

Potassium channels are not only blocked by alkyl ammonium ions like TEA at the external entrance to the selectivity filter, but also within the inner vestibule at the internal entrance to the selectivity filter, where they bind with 1 to 2 orders of magnitude greater affinity. The N-terminal peptide of many K+ channels also binds and blocks at this site in a process known as fast-inactivation. Genetic deletion of the N-terminus from Shaker K+ channels produces channels that do not rapidly inactivate and are therefore called Sh-IR (Shaker-Inactivation Removed). Many intracellular pore blockers, including long-chain alkyl ammonium ions, mimic fast-inactivation when applied to Sh-IR and other non-fast-inactivating channels. This is observed in the current response to a prolonged step depolarization, which opens the voltage gates to allow K+ conductance. After the rapid rising phase of channel opening, current quickly decays or "fast-inactivates" over tens of milliseconds. Because block does not occur until the inner gates have begun to open, which provides access to the inner vestibule, this phenomenon is referred to as "open channel block."

To explore the mechanism of AAQ action on voltage-gated K+ channels, studies were undertaken in HEK293 cells expressing Sh-IR. FIG. 3A shows the current response of an AAQ-treated cell to depolarizing voltage steps. Under 380 nm irradiation, channels are not blocked by AAQ and channel opening is followed only by slow C-type inactivation (purple trace). However, when channels are blocked by AAQ with 500 nm light, substantial peak current remains ($I_{pk}$), which rapidly decays so that nearly all of the steady-state current ($I_{ss}$) is blocked (green trace). This observed fast inactivation is consistent with open channel block at the internal TEA binding site by AAQ. In contrast, fast-inactivation is not observed during blockade of SPARK channels (FIG. 3B), consistent with action at the external TEA binding site.

Positively charged intracellular K+ channel blockers typically exhibit voltage-dependent block, such that $I_{ss}$ is blocked more effectively at depolarized membrane potentials. Because the internal TEA binding site is within the membrane electric field, just as increased depolarization increases the driving force for positively charged K+ ions to flow in the outward direction, alkyl ammonium ions, which cannot permeate, are driven more tightly into the pore and therefore block more effectively. Consistent with this, block by AAQ is distinctly voltage-dependent, such that a higher degree of steady-state current block is observed at more depolarized membrane potentials (FIG. 3C). When Sh-1R channels are completely blocked at 500 nm, the lack of current at all membrane potentials obscures any trend (FIG. 3C, green line; solid squares). However, illumination at 420 nm, which produces 50% cis isomer and therefore ~50% block, reveals voltage-dependent block (FIG. 3C, blue line; solid circles), as indicated by the decline in $I_{ss}$ at more depolarized potentials. However, under 380 nm illumination, channels are completely unblocked and the current increases with voltage in a linear fashion (FIG. 3C, purple line; solid triangles).

A more direct assay for open channel block is to apply the blocking agent while keeping the channels closed at a negative membrane potential. If the channels must be open before the molecules can bind to the pore, there should be little effect on $I_{pk}$ at the onset of the first opening in the presence of blocker. However, once the channels are opened by depolarization, blockade can rapidly accumulate as the inner vestibule of an increasing number of channels is invaded by the blocker. To test for this mode of action, current was monitored before and after application of AAQ to closed channels (FIG. 3D). After measuring the initial current, cells were clamped at −70 mV to ensure a very low probability of opening and then exposed to 300 μM AAQ in the dark for 3 to 4 minutes, which typically produces >70% block of the Iss while channels are opened at 1 Hz. After washout for 1 minute, the $I_{pk}$ measured during the first opening was not reduced, although $I_{ss}$ (observed 200 ms later) was slightly reduced (FIG. 3D inset). During subsequent openings block rapidly accumulated and was completely reversed upon exposure to 380 nm light. Similar results were obtained in 4 other cells.

As implied by the open channel block mechanism, inhibition of voltage gated ion channels by internal blockers occurs in an activity-dependent, accumulative fashion. Functionally, this is observed as a greater degree of block of both $I_{pk}$ and $I_{ss}$ when channels are opened at higher frequencies, which decreases the recovery time between openings. To test for activity-dependent block, cells were given depolarizing pulses at frequencies ranging from 0.125 Hz to 2 Hz with and without exposure to AAQ. Normalized $I_{pk}$ from two different cells is shown in FIG. 3E. Compared to 0.125 Hz, increasing the frequency of channel opening to 2 Hz reduced Ipk in AAQ-treated cells by 55+/−22% (n=5) (black squares). In contrast, the $I_{pk}$ in untreated cells was only reduced by 4.5+/−0.8% (n=3) (open squares), which is likely due to accumulation of C-type inactivation. Further confirmation of activity-dependent block was obtained in a related experiment, which demonstrated that recovery from block correlates with the lime channels are held closed between openings.

Permeant ions are known to enhance the exit rate of charged blockers, which is thought to result from electrostatic repulsion between the ion and the blocking particle. The effect of changing external K+ concentration ($[K+]_o$) on the degree of block afforded by AAQ was examined during whole cell recordings under 500 nm illumination (FIG. 3F). After establishing voltage clamp in standard external buffer ($[K+]_o$=1.5 mM), cells were locally perfused with solutions containing 0.3 mM and 20 mM $[K+]_o$ (ionic strength and Cl⁻ concentration were held constant by adjusting [NaCl]). To normalize for the effects of changing $[K+]_o$ on K+ driving force, currents were also measured at 380 nm, which completely unblocks the channels. Analysis of the currents obtained at +40 mV (normalized to 380 nm) reveals that AAQ block is inversely correlated with $[K+]_o$, strongly supporting that the quaternary ammonium ion of AAQ blocks at the internal TEA binding site.

FIGS. 3A-F. AAQ is an open-channel blocker of the Sh-IR internal TEA-binding site. (a,b) Whole-cell current responses to 200 ms depolarizing current steps from −70 to +40 mV in the presence of 380 nm (purple) or 500 nm (green) light. (a) AAQ imparts fast-inactivation on Sh-IR. (b) Fast-inactivation is absent in MAQ-treated SPARK channels. (c) Steady-state conductance vs. voltage curves under 380 nm (purple; solid triangles), 420 nm (blue; solid circles) and 500 nm (green; solid squares) illumination, constructed from IN curves and normalized to the current measured at 380 nm and +60 mV. (d) AAQ does not block Sh-IR until channels are opened by depolarization. $I_{ss}$ measured over time under the indicated conditions. Channels were opened at 1 Hz. Inset shows the whole-cell current records at the indicated time points. Black bar: −70 mV holding potential; orange bar: 300 μM AAQ; purple bar: 380 nm; green bar: 500 nm. (e) Frequency-dependence of AAQ block. Normalized $I_{pk}$ at the indicated frequencies in a control cell (white squares) and an AAQ-treated cell (black squares). (f) Dependence of AAQ block on external [K+]. Summary of steady-state current responses of a cell to depolarizing current steps from −70 to +40 mV in the presence of 380 nm (purple) or 500 nm (green) light, normalized to the 380 nm response at each $[K+]_o$.

Covalent Modification is not Required

Based on these data, it was reasoned that direct application of AAQ to the cystosol during whole cell recordings should also photosensitize channels, possibly in a covalent fashion. When 1 mM AAQ was added to the recording pipette solution, it was found to photoregulate K+ channels. Again, blockade exhibited the fast-inactivation associated with open channel block at the internal TEA binding site.

To further explore the interaction between AAQ and the internal TEA binding site, inside-out patches were pulled from HEK293 cells expressing Sh-IR, allowing one to apply AAQ directly to the internal TEA binding site and then wash it out. Surprisingly, current block by AAQ was relieved within several seconds of washout with control solution, indicating that covalent reaction did not occur and that AAQ may behave as a photochromic ligand (PCL) rather than a photoswitchable tethered ligang (PTL) under these conditions. A dose-response curve was therefore generated for both trans and cis isomers by illuminating patches with 380 and 500 nm light in the presence of different concentrations of AAQ. These experiments confirmed that AAQ can indeed block as a PCL at the internal TEA binding site (trans-AAQ $IC_{50}$=2.0+/−0.21.1M, cis-AAQ $IC_{50}$=64+/−2.1 µM, n=3-5).

These results not only establish AAQ as an internal blocker, but also demonstrate that it does not need to form a covalent association with the channel to impart photosensitivity. Consistent with this notion, it is difficult to account for the observed fast inactivation and activity-dependent block if AAQ were to attach at a site within the channel lumen, in which case access to the internal TEA binding site should not depend on opening of the intracellular gates.

To determine whether covalent modification is necessary to persistently photosensitize cells under conditions of external application, AAQ was modified. To this end, the AAQ analogue AcAQ (4) was prepared, which is sterically similar to AAQ but lacks the electrophilic double bond and cannot bind covalently. Under extracellular pre-treatment conditions, AcAQ produced considerable sustained photoswitching that is qualitatively indistinct from that obtained with AAQ. Current responses to step depolarization recorded from AcAQ-treated cells are very similar to the AAQ trace in FIG. 3A. Like AAQ, AcAQ persistently blocked the steady-state current in a light-dependent fashion although it cannot covalently modify channels.

Structure-Activity Relationships

These results support an intracellular mode of action for AAQ, implying that it at least partially crosses the cellular membrane in order to block potassium channels. Although this seems counter-intuitive when considering the permanently charged ammonium ion, a substantial number of quaternary local anesthetics have been observed to cross cellular membranes to reach an internal binding site on sodium and calcium channels. Similarly, amphipathic tetraalkyl ammonium ions such as C9-TEA and C12-TEA have been observed to block voltage-gated potassium channels internally when applied externally at sufficiently high concentrations. AAQ and EtAcAQ are both amphipathic molecules that contain a positively charged hydrophilic tetraalkyl ammonium head group and a relatively hydrophobic para-substituted azobenzene tail.

To explore the contribution of hydrophobicity to the potency of molecules like AAQ and AcAQ, a series of Azo-QAs was prepared (FIG. 4). The triethylammonium head group bridged to a 4-aminoazobenzene was conserved while the 4'-substituents were replaced with aliphatic "tails" of increasing hydrophobicity (4-8). The symmetric analogue 9 was also prepared, as this compound would be expected to exhibit poor membrane penetration due to the presence of two positive charges. Finally the amide "tail" was either removed completely (10) or replaced with a propyl group (11) to mimic the length of AcAQ, the shortest analogue previously examined. Prior to screening, U V/V is spectroscopy was used to confirm efficient photoisomerization of each AzoQA. In all cases, exposure to 380 nm and 500 nm light produced photostationary states consisting of at least 80% cis and trans isomers respectively.

These AzoQA's were applied in dark, which favors the trans configuration, at various concentrations to HEK293T cells expressing Sh-IR, followed by washout and whole-cell voltage clamp recording. Because these conditions did not permit measurement of the initial current, we looked for the fast-inactivation associated with open channel block to determine whether or not a molecule was able to block the channel. To quantify the relative potency of each new analogue, we identified the minimal dose that was able to block >95% of $I_{ss}$ measured under 380 nm illumination, which typically resulted in complete unblock as judged by a lack of fast inactivation.

The data obtained for the new analogues, including AcAQ (4), are summarized in FIG. 4. Strikingly, each of the compounds containing a neutral hydrophobic tail (4-8, 10, 11) was able to persistently block the channels for at least several minutes of recording when applied at sufficiently high concentrations. Only compound 9 was not observed to block at all after extracellular treatment, even at 2 mM, although direct cytosolic application did afford block. A general trend was observed in which potency is correlated with tail length and hydrophobicity. Strikingly, compound 8, named BzAQ (Benzoyl-Azo-QA) was found to block >95% of $I_{ss}$ at only 25 µM. In contrast, the truncated analogue 10, which lacks an extended hydrophobic tail, exhibited essentially equal block in both cis and trans forms. This indicates that interactions between the "tail" and channel protein account for the differences in affinity between each isomer. Further supporting this idea, we observed that compound II, named PrAQ (Propyl-Azo-QA) preferentially blocks in the cis form, which stands in contrast to all of the amide-derivatives. Although at higher concentrations, some block by the trans isomer was also apparent as judged by the residual fast inactivation at 500 nm, 40 nM 11 provided 50% block of $I_{ss}$ in the cis form without producing obvious block by the trans isomer.

Intracellular Application Affords Photocontrol in Individual Cells

Figures 5A, 5B:
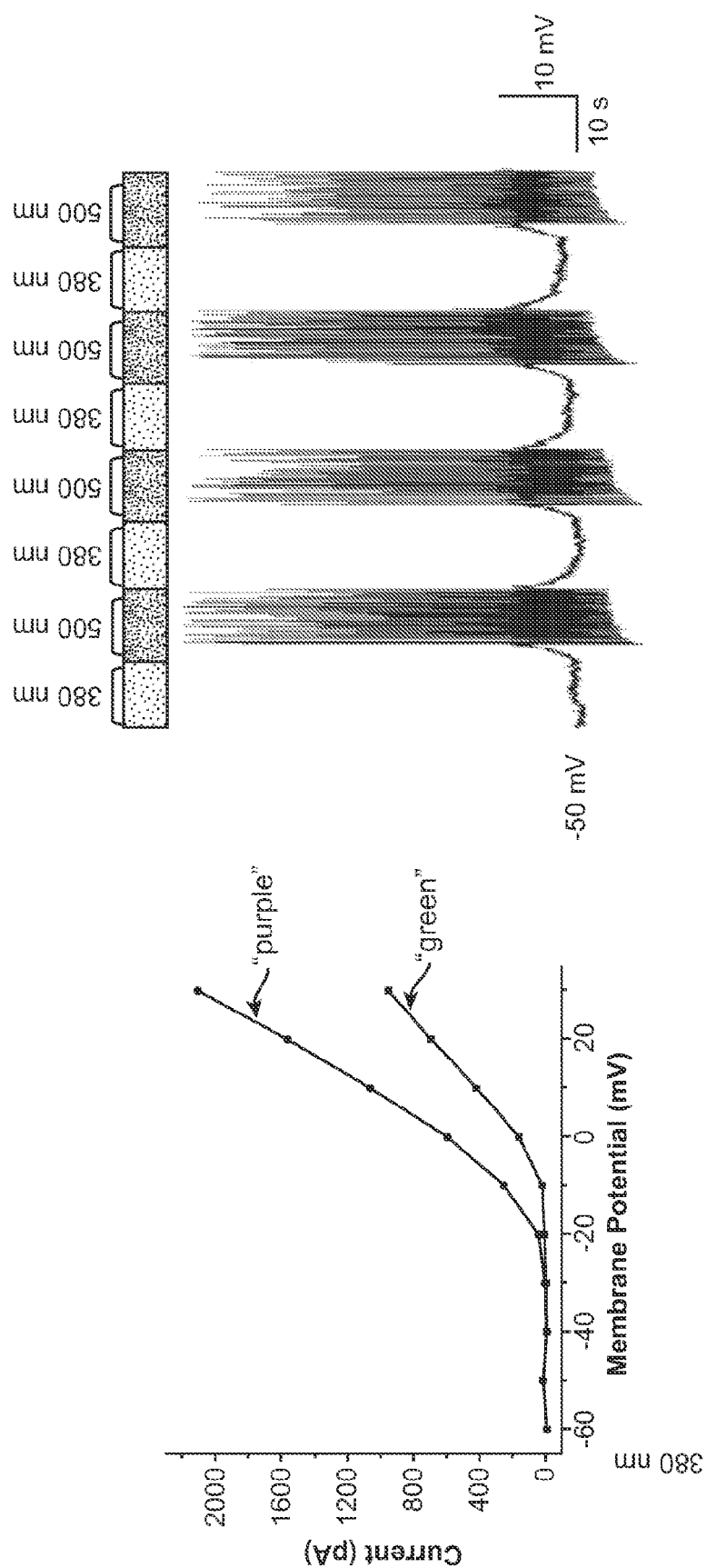
FIGS. 5A and 5B depict BzAQ photoregulation of endogenous $K^+$ channels in dissociated hippocampal neurons to modulate neural activity.

BzAQ was applied to dissociated hippocampal cultures, a preparation in which AAQ was previously found to strongly photosensitize endogenous K+ after preincubation at 300 nM. IV curves from neurons recorded in whole-cell voltage clamp showed that steady state current is modulated significantly after extracellular treatment with 20 µM BzAQ (FIG. 5A). From this data, $I_{ss}$ at +30 mV was compared at 380 and 500 nm, revealing that on average 57+/−6.6% of $I_{ss}$ is blocked by BzAQ under these conditions. In current clamp mode, which allows observation of action potentials, BzAQ was observed to significantly depolarize the cellular membrane potential when switched from cis to trans, which was sufficient to induce action potential firing when the cell was near threshold (FIG. 5B). Together, these data indicate that BzAQ can adequately substitute for AAQ, but with the advantage of increased potency.

FIGS. 5A and 5B. BzAQ photoregulates endogenous K+ channels in dissociated hippocampal neurons to modulate neural activity. (a) Steady-state current vs. voltage curves under 380 nm (purple; solid circles) and 500 nm (green; solid squares) illumination recorded from neurons treated with 20 nM BzAQ. Recordings from individual cells were normalized to the current measured at 380 nm and +30 mV. (b) Current clamp recording from a neuron showing the induction of action potential firing in response to 500 nm light.

Example 2

Synthesis of Synthetic Regulators

General Synthetic Methods.

Reactions were carried out under $N_2$ atmosphere in flame dried glassware. Tetrahydrofuran (THF) was distilled from Na/benzophenone immediately prior to use. Acetonitrile (MeCN), and diisopropylethylamine (DIPEA) were distilled from $CaH_2$ immediately prior to use. All other reagents and solvents were used without further purification from commercial sources. Flash column chromatography was carried out with EcoChrom ICN SiliTech 32-63 D 60 Å silica gel. Reverse-phase chromatography was carried out with Waters Preperative C18 Silica Gel WAT010001 125 Å and Waters Sep-Pak Vac 20 cc C18 Cartridges WAT036925. Reactions and chromatography fractions were monitored with either Merck silica gel 60F254 plates or Analtech C18 silca gel RPS-F 52011 plates, and visualized with UV light and 0.1N HCl. NMR spectra were measured specified solvents and calibrated from residual solvent signal on a Bruker DRX spectrometer at 500 MHz for $^1H$ spectra and 125 MHz for $^{13}C$ spectra and either a Bruker AVB or Bruker AVQ spectrometer at 400 MHz for $^1H$ spectra and 100 MHz for $^{13}C$ spectra. UV/VIS spectra were measured in water at a concentration of 10 nM on an Agilent 8453 UV/VIS spectrometer. Photoisomerization in solution was achieved by irradiation with the un-collimated quartz fiber optic output from a Polychrome V monochromator (Till Photonics).

AAQ (6) was synthesized as previously described (Fortin et al. (2008) *Nature Methods* 5:331) and compounds 7-14 were prepared according to the same general procedures (Scheme 1, below), which are described briefly below. 4,4'-diaminoazobenzene and 4-aminoazobenzene were purchased from commercial sources while compound S6 was prepared from following the general procedure of Priewisch and Ruck-Braun (2005) *J. Org. Chem.* 70:2350, as described below.

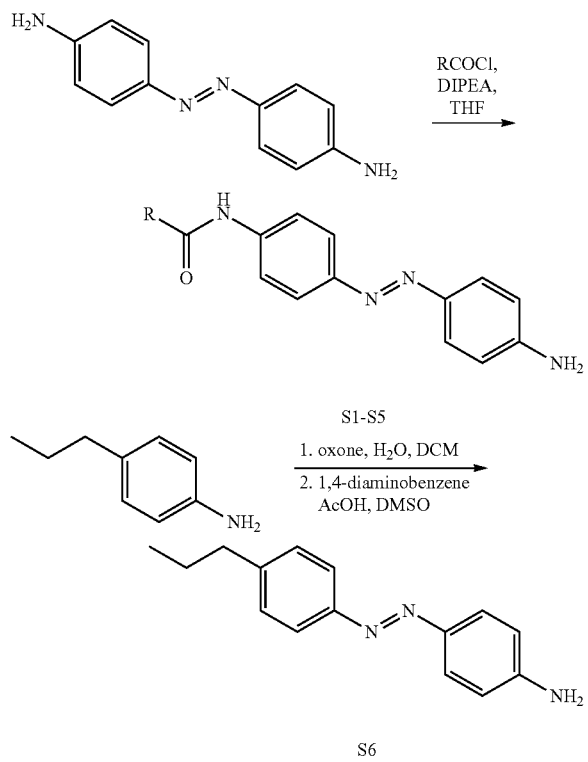

Scheme 1

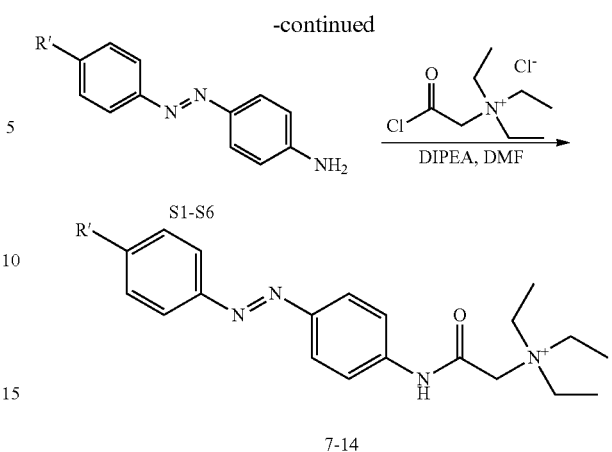

General Procedure for Mono-Acylation of 4,4'-Diaminoazobenzene.

To a solution of 4,4'-diaminoazobenzene (1 eq) and DIPEA (1.2 eq) in THF at 0° C. was added the acid chloride (1.0 eq) in THF over 1 h. The reaction was stirred for 15 min, warmed to room temperature and stirred for 1 h, at which time the crude mixture was removed of solvent in vacuo and immediately dry loaded onto silca gel (2 g) for chromatography.

4-acetamido-4'-aminoazobenzene (S1)

Following the general monoacylation procedure, 4,4'-azodianiline (25 mg, 120 μmol) was treated with acetyl choloride (8.5 μl, 120 μmol). Silica gel chromatography through a wide column (20% ethyl acetate in dichloromethane, gradient to 66%) provided S1 as an orange solid (22 mg, 90 μmol, 73% yield): $^1H$ ($CD_3CN$, 500 MHz): 1.98 (s, 3H); 4.77 (s, 21-1); 6.74 (d, 2H, J=8.5); 7.70 (d, 4H. J=8.5); 7.77 (d, 21-1, J=8.5); 8.53 (s, 1H). $^{13}C$($CD_3CN$, 125 MHz): 23.4, 113.9, 119.3, 122.7, 124.7, 140.6, 144.3, 148.6, 151.5, 168.7. HRMS (FAB+): calc'd for $C_{14}H_{14}N_4O$—254.1168. found—254.1171 (M+).

4-propionamido-4'-aminoazobenzene (S2)

Following the general monoacylation procedure, 4,4'-azodianiline (50 mg, 240 μmol) was treated with propionyl choloride (21 μl, 240 μmol). Silica gel chromatography through a wide column (50% ethyl acetate in hexanes, gradient to 66%) provided S2 as an orange solid (43 mg, 162 μmol, 68% yield): $^1H$ (MeOD, 500 MHz): 1.23 (t, 31-1, J=7.5); 2.41 (q, 21-1, J=7.5); 6.73 (d, 2H, J=8.5); 7.69 (d, 4H, J=8.5); 7.75 (d, 2H, J=8.5). $^{13}C$ (MeOD, 125 MHz): 8.73, 29.64, 113.8, 199.7, 122.3, 124.5, 134.0, 144.3, 149.0, 151.8, 174.0. HRMS (ESI+): calc'd for $C_{15}H_{17}N_4O^+$-269.1397. found 269.1400 (MH+).

4-butyramido-4'-aminoazobenzene (S3)

Following the general monoacylation procedure, 4,4'-azodianiline (50 mg, 240 μmol) was treated with butyryl choloride (25 μl, 240 μmol). Silica gel chromatography through a wide column (50% ethyl acetate in hexanes, gradient to 66%) provided S3 as an orange solid (44 mg, 157 μmol, 65% yield): $^1H$ (MeOD, 400 MHz): 1.01 (t, 3H, J=7.6); 1.74 (q, 21-1, J=7.6); 2.38 (t, 2H, J=7.6); 6.73 (d, 2H, J=8.8); 7.69 (d, 4H, J=8.8); 7.77 (d, 2H, J=8.8). $^{13}C$ (MeOD, 100 MHz): 14.2, 20.4, 40.1, 115.4, 121.2, 121.3, 123.9, 124.7, 126.1, 141.5, 142.8, 145.9, 150.7, 153.4, 174.8. HRMS (FAB+): calc'd for $C_{16}H_{19}N_4O^+$-283.1559. found-283.1556 (MH+).

4-(pent-4-en)amido-4'-aminoazobenzene (S4)

Following the general monoacylation procedure, 4,4'-azodianiline (50 mg, 240 μmol) was treated with 4-pentenoyl choloride (27 μl, 240 μmol). Silica gel chromatography through a wide column (5% ethyl acetate in dichloromethane, gradient to 75%) provided S4 as an orange solid (48 mg, 163 μmol, 68% yield): $^1$H (MeOD, 500 MHz): 2.34-2.42 (m, 4H); 4.89-5.03 (m, 21-1); 5.72-5.86 (m, 1H); 6.63 (d, 2H, J=8.6); 7.58 (d, 4H, J=8.6); 7.65 (d, 2H, J=8.6). $^{13}$C (MeOD, 125 MHz): 29.3, 35.9, 113.8, 114.5, 119.7, 122.3, 124.5, 136.7, 139.8, 144.3, 149.1, 151.8, 172.4. HRMS (FAB+): calc'd for $C_{17}H_{18}N_4O$—294.1481. found—294.1487 (M+).

4-benzamido-4'-aminoazobenzene (S5)

Following the general monoacylation procedure, 4,4'-azodianiline (50 mg, 240 μmol) was treated with benzoyl choloride (26 μl, 240 μmol). Silica gel chromatography through a wide column (10% ethyl acetate in dichloromethane) provided S5 as an orange solid (44 mg, 130 μmol, 54% yield): $^1$H (DMSO, 400 MHz): 6.04 (s, 2H); 6.66 (d, 2H, J=8.4); 7.52-7.65 (m, 5H); 7.76 (d, 2H, J=8.8); 7.88-7.98 (m, 4H); 10.46 (s, 1H). $^{13}$C (DMSO, 100 MHz): 113.4, 120.5, 122.3, 124.9, 127.7, 128.4, 131.7, 134.8, 140.4, 142.9, 148.4, 152.5, 165.7. HRMS (ESI+): calc'd for $C_{19}H_{17}N_4O^+$—317.1397. found—317.1403 (MH+).

4-amino-4'-propylazobenzene (S6)

To a solution of 4-propylaniline (541 μl, 3.7 mmol) in dichloromethane (12.5 ml) was added a solution of oxone (4.55 g, 7.4 mmol) in $H_2O$ (50 ml). The biphasic mixture was stirred vigorously under nitrogen for 1 h, at which time the color had become deep aqua green and the reaction was judged as complete by TLC (1:1 hexanes:ethyl acetate; Rf=0.83). The mixture was transferred to a separatory funnel and the organic layer was removed. The aqueous layer was extracted twice with dichloromethane (20 ml). The combined organics were subsequently washed with 20 ml each of 1M HCl, sat. $NaHCO_3$, $H_2O$, and brine and then dried over $Na_2SO_4$, filtered and removed of solvent in vacuo to provide nitrosyl-4-propylbenzene as a green oil. The crude product was immediately dissolved in glacial acetic acid (30 ml) and stirred under nitrogen, followed by the addition of 1,4-diaminobenzene (400 mg, 3.7 mmol) in dry DMSO (10 ml). The reaction was allowed to stir for 48 hrs, during which time the color turned orange-brown. The mixture was transferred to a separatory funnel containing 100 ml brine and extracted five times with ethyl acetate (50 ml). The combined organics were then washed with dilute NaCl (50 ml) six times to remove the DMSO and then dried of $Na_2SO_4$, filtered removed of solvent in vacuo. Silica gel chromatography through a wide column (40% ethyl acetate in hexanes) provided S6 as an orange solid (432 mg, 1.8 mmol, 49% yield): $^1$H (MeOD, 500 MHz): 0.95 (t, 3H, J=7.5); 1.66 (q, 2H, J=7.5); 2.62 (t, 2H, J=7.5); 6.74 (d, 2H, J=8.5); 7.26 (d, 2H, J=8) 7.70 (d, 4H, J=8.5). $^{13}$C (MeOD, 125 MHz): 12.7, 24.2, 37.4, 113.8, 121.7, 124.6, 128.7, 144.3, 144.4, 151.2, 151.8. HRMS (FAB+): calc'd for $C_{15}H_{18}N_3^+$—240.1495. found—240.1500 (MH+).

General Procedure for Acylation of Aminoazohenzenes with 2-Triethylammonium Acetic Acid Chloride Chloride To a solution of the aminoazobenzene (1 eq) and DIPEA (2 eq) in 1:1 MeCN:DMF at 0° C. was added 2-triethylammonium acetic acid chloride chloride[8] (1.5 eq) in 1:1 MeCN:DMF and stirred for 15 min, then warmed to ambient temperature and stirred for 1-12 h at which time the solvent was removed in vacuo for purification by reverse phase silica gel chromatography (0.1% formic acid in $H_2O$, gradient up to 50% MeCN: 0.1% formic acid in $H_2O$).

4-acetamido-4'-(2)-triethylammoniumacetamidoazobenzene formate; AcAQ (7)

Following the general acylation procedure, 4-acetamido-4'-aminoazobenzene (S1) (10 mg, 39 μmol) provided 7 as an orange solid (15.9 mg, 36 μmol, 93% yield): $^1$H (MeOD, 500 MHz): 1.39 (bs, 9H); 2.17 (s, 3H); 3.68 (bs, 6H); 4.23 (s, 2H); 7.74-7.91 (m, 8H); 8.54 (bs, 1H). $^{13}$C (MeOD, 125 MHz): 6.5, 22.6, 54.4, 56.1, 119.6, 120.0, 123.2, 139.8, 141.4, 148.6, 149.3, 161.8, 170.4, 181.6. HRMS (ESI+): calc'd for $C_{22}H_{30}N_5O_2^+$—396.2394. found—396.2393 (M+).

4-propionamido-4'-(2)-triethylammoniumacetamidoazobenzene formate (8)

Following the general acylation procedure, 4-propionamido-4'-aminoazobenzene (S2) (10 mg, 37 μmol) provided 8 as an orange solid (9.2 mg, 20 μmol, 55% yield): $^1$H (MeOD, 500 MHz): 1.22 (t, 3H, J=7.5); 1.39 (t, 911, J=7.5); 2.43 (q, 2H, J=7.5); 168 (q, 6H, J=7.5); 4.20 (s, 2H); 7.75-7.80 (m, 4H); 7.86-7.91 (m, 4H); 8.44 (bs, 1H). $^{13}$C (MeOD, 125 MHz): 6.5, 8.7, 29.7, 54.3, 54.4, 56.1, 119.6, 120.0, 123.2, 139.7, 141.6, 148.5, 149.4, 161.7, 174.1, 181.5. HRMS (ESI+): calc'd for $C_{23}H_{32}N_5O_2^+$—410.2551. found—410.2548 (M+).

4-butyramido-4'-(2)-triethylammoniumacetamidoazobenzene formate (9)

Following the general acylation procedure, 4-butyramido-4'-aminoazobenzene (S3) (10 mg, 35 μmol) provided 9 as an orange solid (8.7 mg, 18.5 μmol, 53% yield): $^1$H (MeOD, 500 MHz): 1.01 (t, 3H, J=7.5); 1.39 (t, 911, J=7.5); 1.74 (q, 2H, J=7.5); 2.39 (t, 2H, J=7.5); 3.68 (q, 6H, J=7.5); 4.18 (s, 2H); 7.75-7.80 (m, 4H); 7.87-7.92 (m, 4H); 8.55 (bs, 1H). $^{13}$C (MeOD, 125 MHz): 6.5, 12.5, 18.8, 38.5, 54.3, 119.6, 120.0, 123.2, 139.7, 141.5, 148.6, 149.4, 161.7, 173.3, 181.6. HRMS (ESI+): calc'd for $C_{24}H_{34}N_5O_2^+$—424.2707. found—424.2704 (M+).

4-(pent-4-en)amido-4'-(2)-triethylammoniumacetamidoazobenzene formate (10)

Following the general acylation procedure, 4-(pent-4-en)amido-4'-aminoazobenzene (S4) (10 mg, 34 μmol) provided 10 as an orange solid (13 mg, 27 μmol, 79% yield): $^1$H (MeOD, 500 MHz): 1.38 (t, 9H, J=7.5); 2.44-2.51 (m, 4H); 3.67 (q, 6H, J=7.5); 4.22 (s, 2H); 5.01 (d, 2H, J=10); 5.10 (d, 2H, J=17); 5.85-5.93 (m, 1H); (7.74-7.80 (m, 4H); 7.86-7.90 (m, 4H); 8.33 (bs, 1H). $^{13}$C (MeOD, 125 MHz): 6.5, 29.2, 35.9, 54.4, 56.1, 114.5, 119.6, 120.0, 123.2, 136.7, 139.8, 141.4, 148.6, 149.3, 161.8, 172.5. HRMS (ESI+): calc'd for $C_{25}H_{34}N_5O_2^+$—436.2707. found—436.2702 (M+).

4-benzamido-4'-(2)-triethylammoniumacetamidoazobenzene formate; BzAQ (11)

Following the general acylation procedure, 4-benzamido-4'-aminoazobenzene (S5) (10 mg, 32 μmol) provided 11 as an orange solid (6 mg, 12 μmol, 38% yield): $^1$H (MeOD, 400

MHz): 1.41 (t, 9H, J=7.5); 3.69 (q, 6H, J=7.5); 4.21 (s, 2H); 7.52-7.63 (m, 3H); 7.81 (d, 2H, J=8.8); 7.93-7.98 (m, 8H); 8.47 (bs, 1H). $^{13}$C (MeOD, 100 MHz): 6.5, 54.3, 120.0, 120.6, 123.1, 123.2, 127.3, 128.2, 131.7, 134.7, 139.8, 141.5, 148.9, 149.4, 167.5. HRMS (ESI+): calc'd for $C_{27}H_{32}N_5O_2^+$—458.2551. found—448.2550 (M+).

4-4'-bis[(2)-triethylammoniumacetamido]azobenzene bis-formate (12)

Following the general acylation procedure, 4,4'-diaminoazobenzene (10 mg, 47 μmol) was treated with 141 μmol 2-triethylammonium acetic acid chloride chloride to provide 12 as an orange solid (20 mg, 34 μmol, 73% yield): $^1$H (MeOD, 500 MHz): 1.39 (t, 18H, J=7.5); 3.68 (q, 12H, J=7.5); 4.24 (s, 4H): 7.81 (d, 4H. J=8.5); 7.92 (d, 4H, J=8.5); 8.41 (bs, 3H). $^{13}$C (MeOD, 125 MHz): 6.5, 54.4, 56.1, 120.1, 123.3, 140.1, 149.3, 161.9, 181.5. HRMS (ESI+): calc'd for $C_{28}H_{44}N_6O_2^{z2+}$—248.1757. found—248.1756 (M2+/2).

4-(2)-triethylammoniumacetamidoazobenzene formate (13)

Following the general acylation procedure, 4-aminoazobenzene (10 mg, 51 μmol) provided 13 as an orange solid (13.4 mg, 35 μmol, 69% yield): $^1$H (MeOD, 500 MHz): 1.39 (t, 9H, J=7.5); 3.68 (q, 6H, J=7.5); 4.22 (s, 2H); 7.48-7.55 (m, 3H); 7.81 (d, 2H, J=8.5); 7.89 (d, 2H, J=7.5); 7.93 (d, 2H, J=8.5); 8.42 (bs, 1H). $^{13}$C (MeOD, 125 MHz): 6.5, 54.3, 56.1, 120.0, 122.3, 123.4, 128.8, 130.7, 140.1, 149.2, 152.5, 161.9. HRMS (ESI+): calc'd for $C_{20}H_{27}N_4O^+$—339.2179. found—339.2178 (M+).

4-propyl-4'-(2)-triethylammoniumacetamidoazobenzene formate; PrAQ (14)

Following the general acylation procedure, 4-amino-4'-propylazohenzene (S6) (10 mg, 42 μmol) provided 14 as an orange solid (10.3 mg, 24 μmmol, 57% yield): $^1$H (MeOD, 500 MHz): 0.98 (t, 3H, J=7.5); 1.40 (t, 9H, J=7.5); 1.70 (q, 2H, J=7.5); 2.68 (t, 2H, J=7.5); 3.68 (q, 6H, J=7.5); 4.21 (s, 2H); 7.36 (d, 2H, J=8.5); 7.81 (t, 4H, J=8.5); 7.92 (d, 4H, J=8.5); 8.51 (bs, 1H). $^{13}$C (MeOD, 125 MHz): 6.5, 8.7, 29.7, 54.3, 54.4, 56.1, 119.6, 120.0, 123.2, 139.7, 141.6, 148.5, 149.4, 161.7, 174.1, 181.5. HRMS (ESI+): calc'd for $C_{23}H_{33}N_4O$—381.2649. found—381.2650 (M+).

Example 3

Characterization of QAQ

Experiments were conducted to test the effect of QAQ on various channels. It was found that QAQ is able, like local anesthetic, to block voltage gated K, Na and Ca channels, to a similar extent. QAQ was shown to photoregulate Shaker K channel and also other K channel subtypes such as Kv2, Kv3 Kv4 and native K channels in hippocampal cells. QAQ was also shown to photosensitizes native Na channels expressed in NG108-15 cells. QAQ was further shown to photosensitize L type and N type Ca channels.

Figure 6:
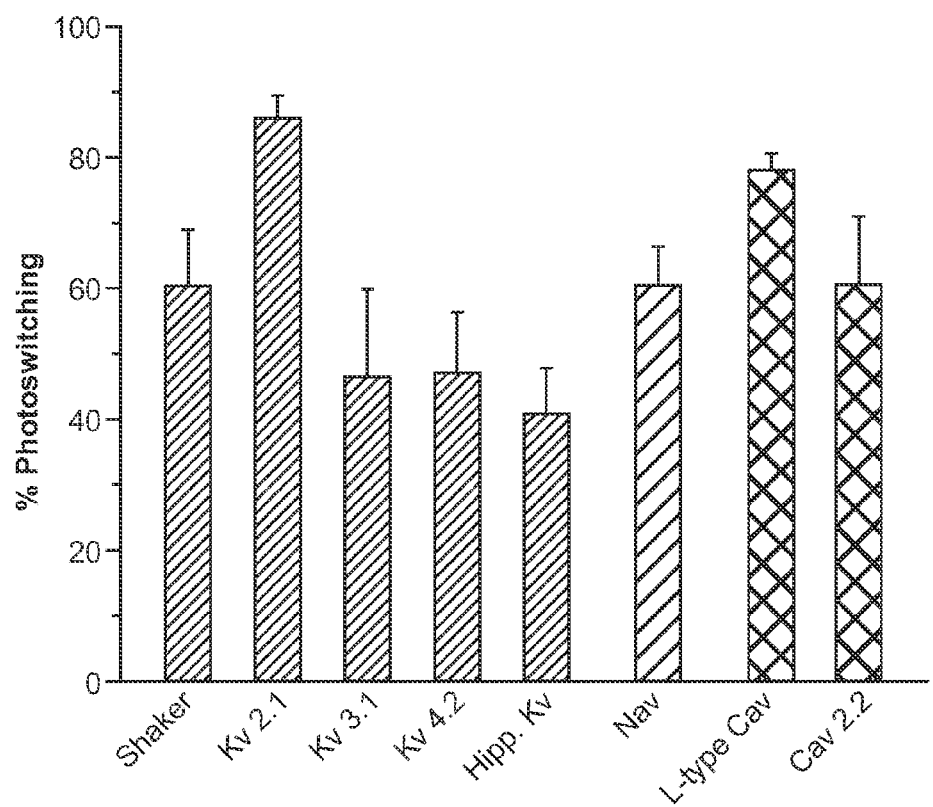
FIG. 6 depicts the activity of QAQ as a photochromic blocker for voltage-gated cation channels.

For all those channels (Kv2.1, Kv3.1, Kv4.2, hippocampal Kv, Nav, L-type Cav, and Cav2.2) the block occurred in the dark, or under 500 nm light. Purple light was used in all cases to relieve the block. FIG. 6 depicts a bar graph showing the quantification of photoswitching on individual channels when having 100 μM QAQ in the pipette.

Figure 7:
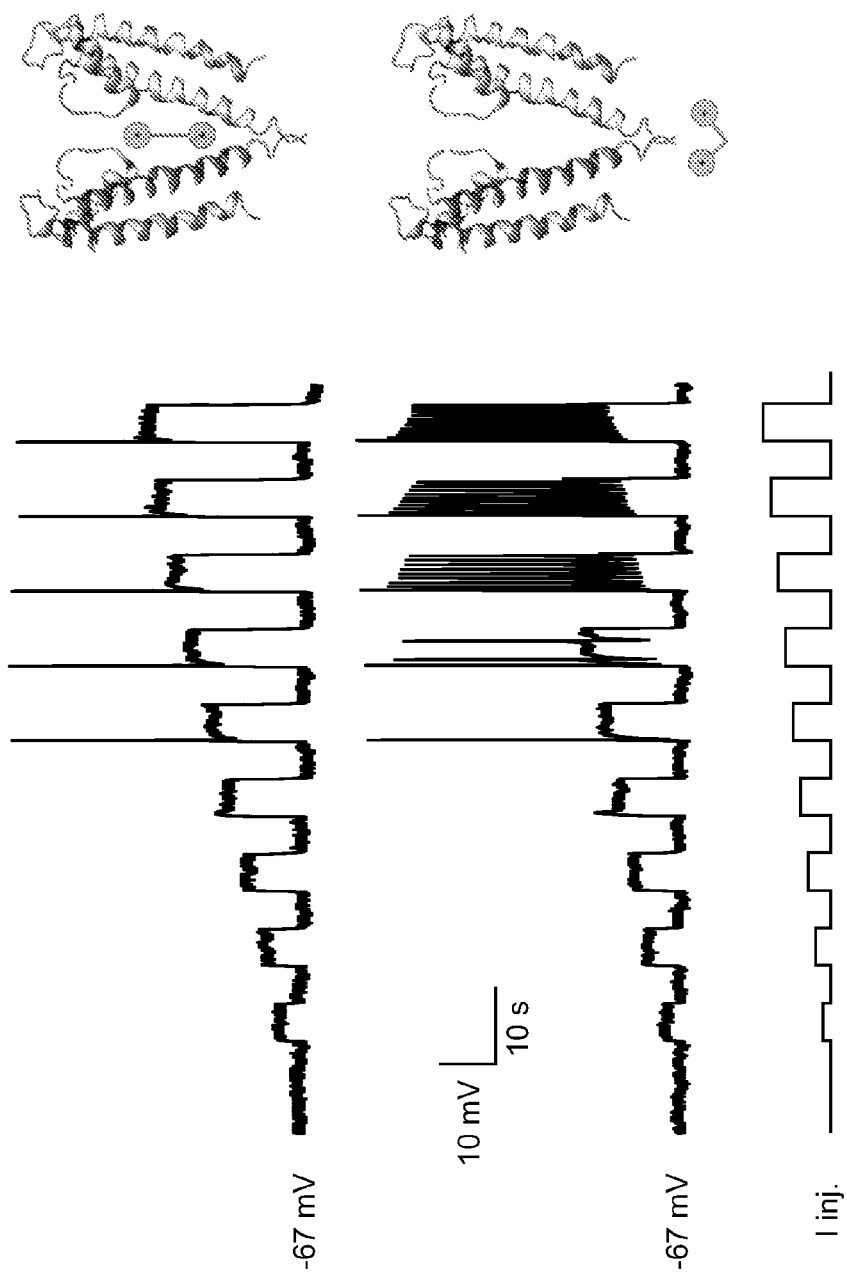
FIG. 7 depicts the activity of QAQ as a silencer of neuronal activity.

The effect of QAQ on neurons was investigated. Neuron firing was examined under current clamp, by injecting progressively greater current into the cell, under 2 different wavelengths of light. As shown in FIG. 7, under green light, the cell does at best one action potential (AP), but remains silent, regardless of the current injected. In contrast, under purple light, the cell fires normally. This is because block of Na channels dominates: when Na channels are blocked, the initial phase of the AP is blocked and neurons are silent. Again, QAQ acts like lidocaine in neurons, silencing cells under green light or in the dark.

QAQ was found to be membrane impermeant. When 100 μM QAQ was applied through the patch pipette to HEK cells expressing Shaker channel, photoregulation of the K channel current was observed. The K current was observed upon a depolarization to +40 mV under purple 380 nm light. Applying green light resulted in a dramatic decrease in K current. In contrast, no photoregulation of K current was seen when QAQ was externally applied, showing that QAQ does not cross the cell membrane.

Advantage was taken of the biophysical properties of certain ion channels. TRPV1 channel and the ATP gated P2X7 receptor can open a wide pore upon prolonged agonist exposure. This pore becomes then permeable to large organic cations like the local anesthetic QX314. It was investigated whether QAQ could be loaded into cells expressing either one of these two channels (P2X$_7$R or TRPV$_1$). If so, specific cells could be targeted with QAQ, and then excitability could be controlled with light. This concept is depicted schematically in FIG. 8.

Figure 9:
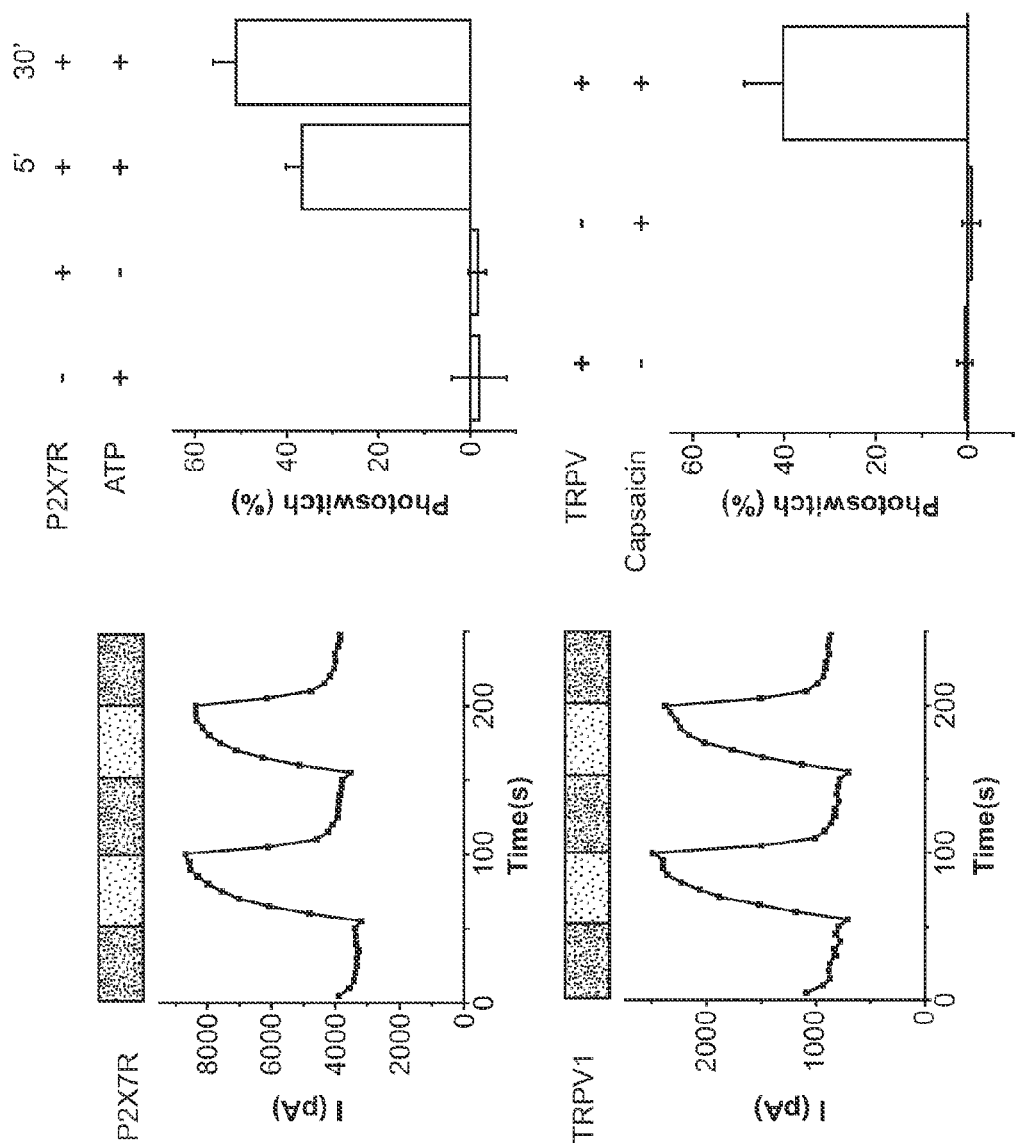
FIG. 9 depicts loading of QAQ into cells through non-selective ion channels.

It was first determined whether P2X$_7$R expressed in HEK cells could be an entry route for QAQ. P2X$_7$R was co-expressed together with Shaker channel. As shown in FIG. 9, QAQ could be loaded in the HEK cell only if P2X7 channels were expressed and ATP, the agonist for the P2X$_7$ channels, was coapplied together with QAQ. As shown in FIG. 9, photoswitching occurred in cells coexpressing P2X$_7$R and Shaker when QAQ was loaded into the cells in the presence of ATP. Even a short application of 5 min was enough to get very good photoswitching (light-controlled activation) of Shaker channels current. Also as shown in FIG. 9, QAQ could be loaded into cells co-expressing TRPV$_1$ and Shaker channel in the presence of the TRPV$_1$ agonist capsaicin. Furthermore, when cells co-expressing TRPV$_1$ and Shaker channel were loaded with QAQ (in the presence of capsaicin), photoswitching could be effected.

Figure 10:
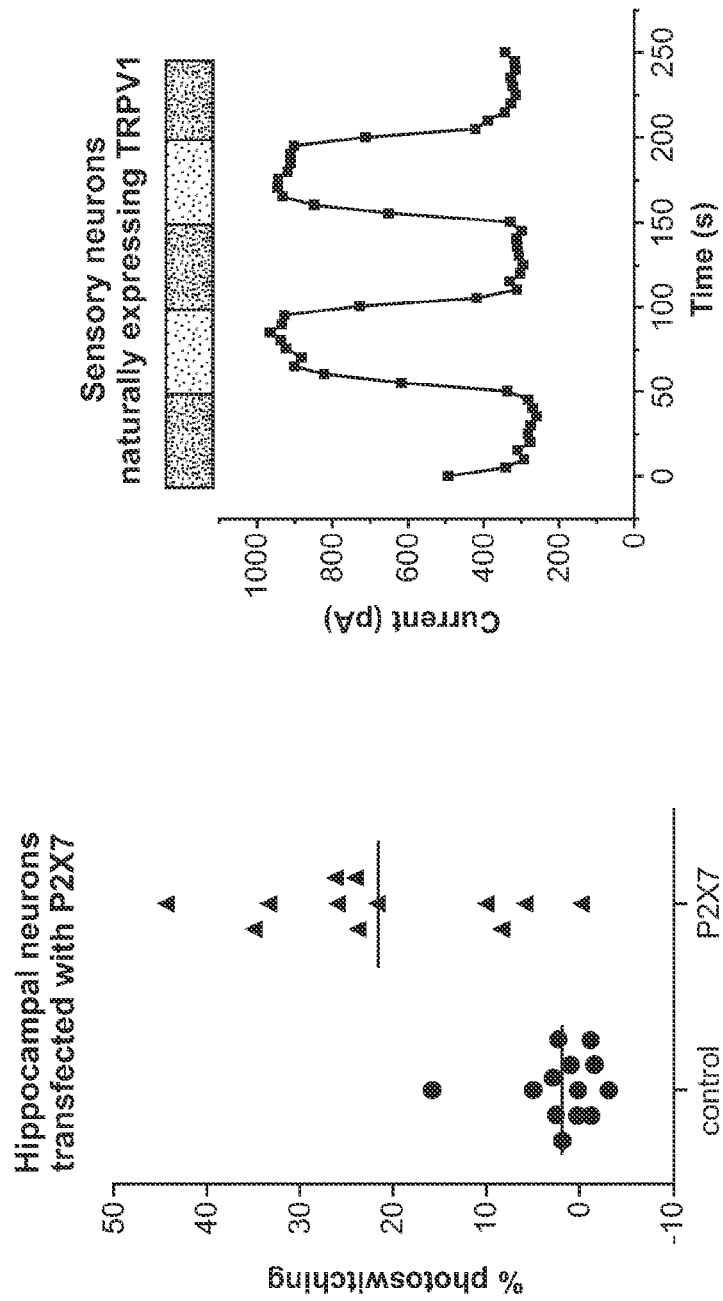
FIG. 10 depicts loading of QAQ into hippocampal neurons transfected with the non-selective cation channel $P2X_7R$, using ATP (left panel); and loading of QAQ into sensory neurons that naturally express the non-selective cation channel TRPV1.

Hippocampal neurons were transfected with P2X$_7$R. As shown in FIG. 10 (left panel) QAQ could be loaded into cells only when P2X7 receptors were expressed. In 1 of 13 cells tested, QAQ entered a cell which was not heterologously expressing P2X$_7$R, possibly because this cell was expressing endogenous P2X$_7$ receptors. It was then asked whether QAQ could enter cells naturally expressing either of these channels and looked at sensory neurons. Sensory neurons are activated by sensory input and project towards the central nervous system. Sensory neurons of the trigeminal ganglia naturally express TRPV1 channels. QAQ was applied together with capsaicin on these sensory neurons in in vitro culture. Again, it very robust photoswitching of native K channels was seen (FIG. 10, right panel).

Example 4

Photoregulationg Nociception In Vivo

It was shown (Example 3) that QAQ blocks capsaicin-evoked sensory neuron activation in vitro, in a light-dependent manner. It was then tested whether QAQ can block nocifensive responses in vivo, and whether this action can be regulated by light. This experiment consisted of 2 parts: (1) it was tested whether QAQ acts as an analgesic, in the absence of light. In vitro studies suggested that in ambient light, QAQ is in an active form and thus should block nocifensive behaviors by blocking activity of C-fibers; (2) based on the results of part (1), the same experiment was performed in the presence of 380 nm light.

Figure 11:
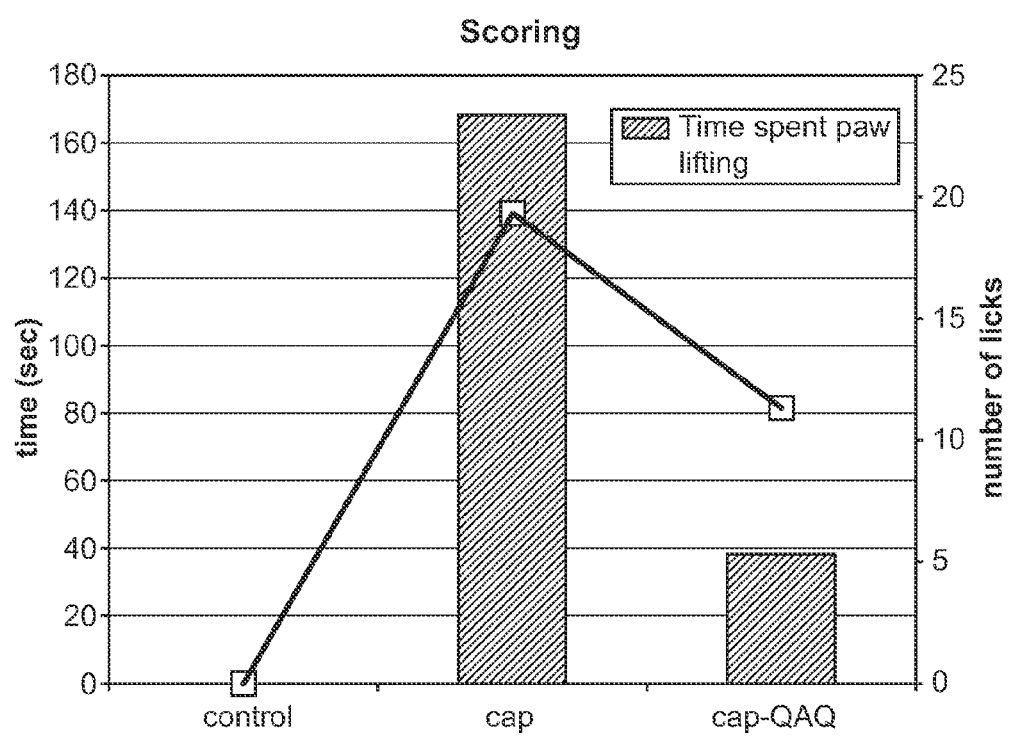
FIG. 11 depicts in vivo blocking of capsaicin-activated sensory neurons.

Injection of capsaicin into the mouse hindpaw elicits a 5-10 min bout of licking and flinching; such responses are blocked by co-application of lidocaine, morphine, and other analgesics (Binshtock et al., 2007 Nature 449:607-10). Because analgesics are molecules that alleviate pain, evaluating the analgesic properties of a new molecule requires induction of discomfort in animals. The ability of QAQ to inhibit capsaicin-evoked nocifensive behaviors was tested. Fourteen mice were used for this experiment: to one set of 7 mice, capsaicin alone was applied by injection; to a second set of 7 mice, capsaicin and QAQ were co-injected. The mice were then placed in a transparent Plexiglas chamber and behavior was video recorded for 10 min. After 10 min, mice were euthanized. As shown in FIG. 11, co-injection of QAQ along with capsaicin reduced the number of licks and the time spent paw lifting.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the formula:

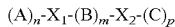

(A)$_n$-X$_1$-(B)$_m$-X$_2$-(C)$_p$ wherein

A is a polypeptide association moiety selected from hydrogen, C$_1$-C$_{10}$ alkyl, substituted C$_1$-C$_{10}$ alkyl, —NR$^{10}$R$^{11}$, —NR$^{12}$C(O)R$^{13}$, C$_{2-10}$ alkenyl, substituted C$_{2-10}$ alkenyl, C$_{2-10}$ alkynyl, substituted C$_{2-10}$ alkynyl, C$_{6-20}$ aryl, substituted C$_{6-20}$ aryl, heteroaryl, heterocyclic, heterocyclooxy, heterocyclothio, heteroarylamino, heterocycloamino, C$_{4-10}$ cycloalkyl, substituted C$_{4-10}$ cycloalkyl, C$_{4-10}$ cycloalkenyl, substituted C$_{4-10}$ cycloalkenyl, cyano, halo, —OR$^{10}$, —C(O)OR$^{10}$, —SR$^{10}$, —S(O)R$^{10}$, —S(O)$_2$R$^{10}$;

wherein

R$^{10}$ and R$^{11}$ are independently selected from hydrogen and C$_{1-10}$ alkyl;

R$^{12}$ is hydrogen or C$_{1-10}$ alkyl; and

R$^{13}$ is selected from hydrogen, C$_{1-10}$ alkyl, C$_{1-8}$ alkenyl, C$_{6-10}$ aryl, and substituted C$_{1-10}$ alkyl;

B is a photoisomerizable group comprising an azobenzene;

C is a ligand selected from an agonist, an antagonist, an allosteric modulator, and a blocker;

n is 1;

each of m and p is independently an integer from 1 to 10; and

X$_1$ and X$_2$ are each an optional spacer independently selected from alkyl, substituted alkyl, alkenyl, substituted alkenyl, alkynyl, substituted alkynyl, acyl, acylamino, and aminoacyl.

2. The compound of claim 1, wherein the polypeptide association moiety comprises a group selected from C$_1$-C$_{10}$ alkyl, substituted C$_1$-C$_{10}$ alkyl, and —NR$^{10}$R$^{11}$, wherein R$^{10}$ and R$^{11}$ are independently selected from hydrogen and C$_{1-10}$ alkyl.

3. The compound of claim 1, wherein the polypeptide association moiety comprises —NR$^{10}$R$^{11}$, wherein each of R$^{10}$ and R$^{11}$ are hydrogen.

4. The compound of claim 1, wherein the polypeptide association moiety comprises —NR$^{10}$R$^{11}$, wherein each of R$^{10}$ and R$^{11}$ are C$_{1-10}$ alkyl.

5. The compound of claim 1, wherein the polypeptide association moiety comprises —NR$^{10}$R$^{11}$, wherein each of R$^{10}$ and R$^{11}$ are methyl.

6. The compound of claim 1, wherein the polypeptide association moiety comprises a substituted C$_1$-C$_{10}$ alkyl.

7. The compound of claim 1, wherein the polypeptide association moiety comprises a C$_1$-C$_{10}$ alkyl with one or more halogen substituents.

8. The compound of claim 1, wherein the polypeptide association moiety comprises a C$_1$-C$_{10}$ alkyl with one or more fluoro substituents.

9. The compound of claim 1, wherein the polypeptide association moiety comprises a methyl with one or more halogen substituents.

10. The compound of claim 1, wherein the polypeptide association moiety comprises a methyl with one or more fluoro substituents.

11. The compound of claim 1, wherein each of n, m, and p is one.

12. The compound of claim 1, wherein the ligand is a ligand for an ion channel.

13. The compound of claim 12, wherein the ion channel is a sodium channel, a potassium channel, a calcium channel, or a chloride channel.

14. The compound of claim 1, wherein the ligand is selected from an α-amino-3-hydroxy-5-methylisoxazole-4-propionic acid (AMPA) receptor agonist, a GABA$_A$ receptor ligand, and a transient receptor potential cation channel, subfamily V, member 1 (TRPV$_1$) ligand.

15. The compound of claim 1, wherein the compound is a compound of Formula XII:

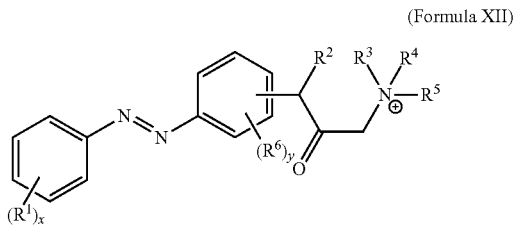

(Formula XII)

wherein x is 1;

y is 1;

R$^1$ is —NR$^{10}$R$^{11}$;

R$^2$ is hydrogen;

R$^3$, R$^4$, and R$^5$ are each independently C$_{2-8}$ alkyl;

R$^6$ is hydrogen;

R$^{10}$ is C$_{1-10}$ alkyl;

R$^{11}$ is substituted C$_{1-10}$ alkyl; and or a pharmaceutically acceptable salt thereof.

16. The compound of claim 15, wherein:

R$^3$, R$^4$, and R$^5$ are each C$_3$alkyl;

R$^{10}$ is C$_2$alkyl; and $R^{11}$ is methyl substituted with an aryl.

17. The compound of claim 16, wherein $R^{11}$ is methyl substituted with phenyl.

18. The compound of claim 15, wherein:
$R^3$, $R^4$, and $R^5$ are each $C_4$alkyl;
$R^{10}$ is $C_2$alkyl; and
$R^{11}$ is methyl substituted with an aryl.

19. The compound of claim 18, wherein $R^{11}$ is methyl substituted with phenyl.

20. The compound of claim 15, wherein:
$R^3$, $R^4$, and $R^5$ are each $C_2$alkyl;
$R^{10}$ is $C_2$alkyl; and
$R^{11}$ is methyl substituted with substituted aryl.

21. The compound of claim 20, wherein $R^{11}$ is methyl substituted with substituted phenyl.

22. The compound of claim 1, wherein the compound is a compound of Formula XI:

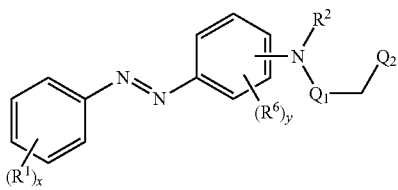

(Formula XI)

wherein
$Q^1$ is —C(=O)—;
$Q^2$ is $NR^3R^4$;
$R^3$ and $R^4$ are each $C_2$alkyl;
$R^1$ is —$NR^{10}R^{11}$;
x is 1;
y is 1;
$R^2$ is hydrogen;
$R^6$ is hydrogen;
$R^{10}$ is $C_2$alkyl; and
$R^{11}$ is methyl substituted with aryl;
or a pharmaceutically acceptable salt thereof.

23. The compound of claim 1, wherein:
A is an —$NR^{10}R^{11}$ group;
$R^{10}$ is $C_{1-10}$ alkyl;
$R^{11}$ is substituted $C_{1-10}$ alkyl;
B is a photoisomerizable group comprising an azobenzene;
C is a ligand selected from an agonist, an antagonist, an allosteric modulator, and a blocker;
each of n, m, and p is 1; and
$X_1$ and $X_2$ are each an optional spacer independently selected from alkyl, substituted alkyl, alkenyl, substituted alkenyl, alkynyl, substituted alkynyl, acyl, acylamino, and aminoacyl.

24. The compound of claim 23, wherein $R^{11}$ is methyl substituted with aryl.

25. The compound of claim 24, wherein $R^{11}$ is methyl substituted with phenyl.

26. The compound of claim 23, wherein $R^{10}$ is $C_2$alkyl.

27. The compound of claim 23, wherein the ligand is a ligand for an ion channel.

28. The compound of claim 27, wherein the ion channel is a sodium channel, a potassium channel, a calcium channel, or a chloride channel.

* * * * *